(12) United States Patent
Voronenko et al.

(10) Patent No.: US 11,033,757 B2
(45) Date of Patent: Jun. 15, 2021

(54) METHODS FOR REAL-TIME IMAGE GUIDED RADIATION THERAPY

(71) Applicant: Reflexion Medical, Inc., Hayward, CA (US)

(72) Inventors: Yevgen Voronenko, Sunnyvale, CA (US); Peter Demetri Olcott, Los Gatos, CA (US); Debashish Pal, Sunnyvale, CA (US); Rostem Bassalow, Hayward, CA (US)

(73) Assignee: RefleXion Medical, Inc., Hayward, CA (US)

( * ) Notice: Subject to any disclaimer, the term of this patent is extended or adjusted under 35 U.S.C. 154(b) by 21 days.

(21) Appl. No.: 16/554,258

(22) Filed: Aug. 28, 2019

(65) Prior Publication Data

US 2019/0381338 A1 Dec. 19, 2019

Related U.S. Application Data

(63) Continuation of application No. 15/993,325, filed on May 30, 2018, now Pat. No. 10,688,320.

(Continued)

(51) Int. Cl.
*A61N 5/10* (2006.01)

(52) U.S. Cl.
CPC ......... *A61N 5/1067* (2013.01); *A61N 5/1036* (2013.01); *A61N 5/1039* (2013.01);
(Continued)

(58) Field of Classification Search
CPC .. A61N 5/1067; A61N 5/1081; A61N 5/1049; A61N 5/1071; A61N 5/1036;
(Continued)

(56) References Cited

U.S. PATENT DOCUMENTS 3,794,840 A 2/1974 Scott
5,647,663 A 7/1997 Holmes
(Continued)

FOREIGN PATENT DOCUMENTS

CN 104866928 A 8/2015
CN 104994909 A 10/2015
(Continued)

OTHER PUBLICATIONS

Akpati, H.C. et al. (2008). "Unified dosimetry index (UDI): A figure of merit for ranking treatment plans," J Appl Clin Med Phys. 9:99-108.
(Continued)

*Primary Examiner* — Courtney D Thomas
(74) *Attorney, Agent, or Firm* — Cooley LLP

(57) ABSTRACT

Disclosed herein are systems and methods for guiding the delivery of therapeutic radiation using incomplete or partial images acquired during a treatment session. A partial image does not have enough information to determine the location of a target region due to, for example, poor or low contrast and/or low SNR. The radiation fluence calculation methods described herein do not require knowledge or calculation of the target location, and yet may help to provide real-time image guided radiation therapy using arbitrarily low SNR images.

39 Claims, 18 Drawing Sheets

Related U.S. Application Data

(60) Provisional application No. 62/537,384, filed on Jul. 26, 2017, provisional application No. 62/512,632, filed on May 30, 2017.

(52) U.S. Cl.
CPC ......... *A61N 5/1049* (2013.01); *A61N 5/1071* (2013.01); *A61N 5/1081* (2013.01); *A61N 5/1068* (2013.01); *A61N 2005/1052* (2013.01); *A61N 2005/1055* (2013.01); *A61N 2005/1061* (2013.01); *A61N 2005/1091* (2013.01)

(58) Field of Classification Search
CPC .......... A61N 5/1039; A61N 2005/1091; A61N 2005/1052; A61N 2005/1055; A61N 2005/1061; A61N 5/1068
See application file for complete search history.

(56) References Cited

U.S. PATENT DOCUMENTS

| | | | |
|---|---|---|---|
| 6,023,494 A | 2/2000 | Senzig et al. | |
| 6,038,283 A | 3/2000 | Carol et al. | |
| 6,393,096 B1 | 5/2002 | Carol et al. | |
| 6,438,202 B1 | 8/2002 | Olivera et al. | |
| 6,459,762 B1 | 10/2002 | Wong et al. | |
| 6,504,899 B2 | 1/2003 | Pugachev et al. | |
| 6,661,870 B2 | 12/2003 | Kapatoes et al. | |
| 6,714,620 B2 | 3/2004 | Caflisch et al. | |
| 6,810,108 B2 | 10/2004 | Clark et al. | |
| 7,015,490 B2 | 3/2006 | Wang et al. | |
| 7,265,356 B2 | 9/2007 | Pelizzari et al. | |
| 7,266,175 B1 | 9/2007 | Romesberg | |
| 7,280,633 B2 | 10/2007 | Cheng et al. | |
| 7,302,038 B2 | 11/2007 | Mackie et al. | |
| 7,343,030 B2 | 3/2008 | Sawyer | |
| 7,379,531 B2 | 5/2008 | Esham et al. | |
| 7,412,029 B2 | 8/2008 | Myles | |
| 7,446,328 B2 | 11/2008 | Rigney et al. | |
| 7,508,967 B2 | 3/2009 | Harari et al. | |
| 7,513,861 B2 | 4/2009 | Klein et al. | |
| 7,611,452 B2 | 11/2009 | Allison et al. | |
| 7,639,853 B2 | 12/2009 | Olivera et al. | |
| 7,657,304 B2 | 2/2010 | Mansfield et al. | |
| 7,693,257 B2 | 4/2010 | Allison | |
| 7,839,972 B2 | 11/2010 | Ruchala et al. | |
| 7,983,380 B2 | 7/2011 | Guertin et al. | |
| 8,019,042 B2 | 9/2011 | Shukla et al. | |
| 8,063,376 B2 | 11/2011 | Maniawski et al. | |
| 8,090,074 B2 | 1/2012 | Filiberti et al. | |
| 8,107,589 B2 | 1/2012 | Sakurai et al. | |
| 8,144,962 B2 | 3/2012 | Busch et al. | |
| 8,149,991 B2 | 4/2012 | Moreau | |
| 8,260,013 B2 | 9/2012 | Pekar et al. | |
| 8,269,195 B2 | 9/2012 | Rigney et al. | |
| 8,278,633 B2 | 10/2012 | Nord et al. | |
| 8,406,844 B2 | 3/2013 | Ruchala et al. | |
| 8,442,287 B2 | 5/2013 | Fordyce, II et al. | |
| 8,467,497 B2 | 6/2013 | Lu et al. | |
| 8,483,803 B2 | 7/2013 | Partain et al. | |
| 8,509,383 B2 | 8/2013 | Lu et al. | |
| 8,588,367 B2 | 11/2013 | Busch et al. | |
| 8,681,938 B2 | 3/2014 | Myles | |
| 8,767,917 B2 | 7/2014 | Ruchala et al. | |
| 8,816,307 B2 | 8/2014 | Kuusela et al. | |
| 8,836,697 B2 | 9/2014 | Nord et al. | |
| 9,437,340 B2 | 9/2016 | Echner et al. | |
| 9,498,167 B2 | 11/2016 | Mostafavi et al. | |
| 9,956,429 B2 | 5/2018 | Holmes et al. | |
| 9,974,494 B2 | 5/2018 | Mostafavi et al. | |
| 10,456,600 B2 | 10/2019 | Owens et al. | |
| 10,688,320 B2 | 6/2020 | Voronenko et al. | |
| 10,918,884 B2 | 2/2021 | O'Connor et al. | |
| 2004/0079899 A1 | 4/2004 | Ma | |
| 2004/0096033 A1 | 5/2004 | Seppi et al. | |
| 2004/0120452 A1 | 6/2004 | Shapiro et al. | |
| 2004/0122308 A1 | 6/2004 | Ding | |
| 2004/0264640 A1 | 12/2004 | Myles | |
| 2005/0089135 A1 | 4/2005 | Toth et al. | |
| 2005/0109939 A1 | 5/2005 | Engler et al. | |
| 2005/0111621 A1 | 5/2005 | Riker et al. | |
| 2005/0111757 A1 | 5/2005 | Brackett et al. | |
| 2005/0113961 A1 | 5/2005 | Sabol et al. | |
| 2005/0197564 A1 | 9/2005 | Dempsey | |
| 2006/0058637 A1 | 3/2006 | Sommer | |
| 2006/0159220 A1 | 7/2006 | Heuscher | |
| 2006/0241332 A1 | 10/2006 | Klein et al. | |
| 2006/0293583 A1 | 12/2006 | Saracen et al. | |
| 2008/0002811 A1 | 1/2008 | Allison | |
| 2008/0031406 A1 | 2/2008 | Yan et al. | |
| 2008/0071131 A1 | 3/2008 | Rietzei | |
| 2009/0116616 A1 | 5/2009 | Lu et al. | |
| 2009/0296886 A1 | 12/2009 | Maltz et al. | |
| 2010/0054411 A1 | 3/2010 | Nord et al. | |
| 2010/0086183 A1 | 4/2010 | Vik et al. | |
| 2010/0150309 A1 | 6/2010 | Nord et al. | |
| 2011/0049377 A1 | 3/2011 | Morf et al. | |
| 2011/0122997 A1 | 5/2011 | Lu et al. | |
| 2011/0291015 A1 | 12/2011 | Mazin | |
| 2012/0053961 A1 | 3/2012 | Wang et al. | |
| 2012/0230464 A1 | 9/2012 | Ling et al. | |
| 2012/0250971 A1 | 10/2012 | Holmes et al. | |
| 2012/0292534 A1 | 11/2012 | Geneser et al. | |
| 2013/0083004 A1 | 4/2013 | Nord et al. | |
| 2013/0102830 A1 | 4/2013 | Otto | |
| 2013/0188856 A1 | 7/2013 | Adler, Jr. et al. | |
| 2014/0126700 A1 | 5/2014 | Gertner et al. | |
| 2014/0270053 A1 | 9/2014 | Larson | |
| 2015/0043709 A1* | 2/2015 | Shapiro ................... A61B 6/42 378/19 |
| 2015/0161338 A1 | 6/2015 | Scherrer et al. | |
| 2015/0224342 A1 | 8/2015 | Baltes et al. | |
| 2015/0360056 A1 | 12/2015 | Xing et al. | |
| 2015/0367143 A1 | 12/2015 | Muraki et al. | |
| 2016/0023019 A1 | 1/2016 | Filiberti et al. | |
| 2016/0038767 A1 | 2/2016 | Wiersma et al. | |
| 2016/0140300 A1 | 5/2016 | Purdie et al. | |
| 2016/0193480 A1 | 7/2016 | Ribbing et al. | |
| 2016/0361566 A1 | 12/2016 | Larkin et al. | |
| 2016/0361568 A1 | 12/2016 | Chappelow et al. | |
| 2017/0023494 A1 | 1/2017 | Yu et al. | |
| 2017/0028220 A1 | 2/2017 | Schulte et al. | |
| 2018/0133518 A1 | 5/2018 | Harper et al. | |
| 2018/0345042 A1 | 12/2018 | Voronenko et al. | |
| 2018/0369611 A1 | 12/2018 | Owens et al. | |
| 2019/0001152 A1 | 1/2019 | O'Connor et al. | |
| 2019/0054320 A1 | 2/2019 | Owens et al. | |
| 2019/0381338 A1 | 12/2019 | Voronenko et al. | |

FOREIGN PATENT DOCUMENTS

| | | |
|---|---|---|
| EP | 0 212 135 B1 | 9/1991 |
| EP | 1 454 653 B1 | 9/2007 |
| EP | 1 501 604 B1 | 12/2009 |
| EP | 1 898 234 B1 | 4/2010 |
| EP | 2 874 702 B1 | 9/2016 |
| JP | 2002-522128 A | 7/2002 |
| WO | WO-03/076003 A2 | 9/2003 |
| WO | WO-03/076003 A3 | 9/2003 |
| WO | WO-2004/105574 A2 | 12/2004 |
| WO | WO-2004/105574 A3 | 12/2004 |
| WO | WO-2005/031629 A1 | 4/2005 |
| WO | WO-2007/082126 A2 | 7/2007 |
| WO | WO-2007/082126 A3 | 7/2007 |
| WO | WO-2008/011725 A1 | 1/2008 |
| WO | WO-2015/168431 A1 | 11/2015 |
| WO | WO-2016/023786 A1 | 2/2016 |

(56) References Cited

FOREIGN PATENT DOCUMENTS

| WO | WO-2018/183748 A1 | 10/2018 |
|---|---|---|
| WO | WO-2018/237328 A1 | 12/2018 |

OTHER PUBLICATIONS

Alrowaili, Z.A. et al. (2015). "2D mapping of the MV photon fluence and 3D dose reconstruction in real time for quality assurance during radiotherapy treatment," J. Instrumentation IOP Science 10:P09019, 17 total pages.
ArcCHECK® & 3DVH (2016). Sun Nuclear, located at https://www.sunnuclear.com/solutions/patientqa/arccheck3dvh, retrieved on Jul. 31, 2019, 12 total pages.
Chang, J.Y. et al. (2008). "Image-guided radiation therapy for non-small cell lung cancer," J. Thorac Oncol. 3:177-186 (Abstract Only).
Chen, Q. et al. (2016). "SU-D-201-03: During-Treatment Delivery Monitoring System for TomoTherapy," Med. Phys. 43:3334, 1 total page.
Chen, Q. (2016) "During treatment delivery monitoring system for tomotherapy," Presentation, University of Virginia Health System, 16 total pages.
Chen, X. et al. (2012). "Smoothing proximal gradient method for general structured sparse regression," The Annals of Applied Statistics 6:719-752.
Dieterich, S. et al. (2003). "Skin respiratory motion tracking for stereotactic radiosurgery using the CyberKnife," Elsevier Int'l Congress Series 1256:130-136.
ECN Magazine (2016). "Magic plate radiation detector helps improve cancer radiotherapy," located at https://www.ecnmag.com/news/2016/03/magic-plate-radiation-detector-helps-improve-cancer-radiotherapy, retrieved on Jul. 31, 2019, 5 total pages.
Fan, Q. et al. (2013). "Toward a Planning Scheme for Emission Guided Radiation Therapy (EGRT): FDG Based Tumor Tracking in a Metastatic Breast Cancer Patient," Med. Phys. 40(8): 12 pages.
Fan, Q. et al. (2012). "Emission Guided Radiation Therapy for Lung and Prostate Cancers: A Feasibility Study on a Digital Patient," Med. Phys. 39(11):7140-7152.
Fredriksson (2013). "Robust optimization of radiation therapy accounting for geometric uncertainty," KTH Engin. Sciences, pp. 8-14.
Gibbons, J.P. (2004). "Dose calculation and verification for tomotherapy," 2004 ACMP Meeting, Scottsdale, AZ., 71 total pages.
Handsfield, L.L. et al. (2014). "Phantomless patient-specific TomoTherapy QA via delivery performance monitoring and a secondary Monte Carlo dose calculation," Med. Phys. 41:101703-1 101703-9.
Hunt, M.A. et al. (2003). "Treatment Planning Considerations using IMRT," pp. 103-121.
International Search Report dated Nov. 16, 2018, for PCT Application No. PCT/US2018/039104, filed on Jun. 22, 2018, 4 pages.
International Search Report dated Oct. 3, 2018, for PCT Application No. PCT/US2018/035188, filed on May 30, 2018, 4 pages.
International Search Report dated Oct. 3, 2018, for PCT Application No. PCT/US2018/043954, filed on Jul. 26, 2018, 3 pages.
Kak, A. et al. (1988). "Aliasing artifacts and noise in CT images," Principles of computerized tomographic imaging, pp. 177-201.
Kapatoes, J.M. et al. (2001). "A feasible method for clinical delivery verification and dose reconstruction in tomotherapy," Med. Phys. 28:528-542.
Kapatoes, J.M. (2001). "On the accuracy and effectiveness of dose reconstruction for tomotherapy," Physics in Med. Biol. 46:943-966.
Keall, P.J. et al. (2001). "Motion adaptive x-ray therapy: a feasibility study," Physics in Med. Biol. 46:1-10.
Lu, W. (2008). "Real-time motion-adaptive delivery (MAD) using binary MLC: I. Static beam (topotherapy) delivery," Phys. Med. Biol. 53:6491-6511.
Lu, W. (2009). "Real-time motion-adaptive-optimization (MAO) in tomotherapy," Phys. Med. Biol. 54:4373-4398.
Mackie, T.R. et al. (1993). "Tomotherapy: A new concept for the delivery of dynamic conformal radiotherapy," Med. Phys. 20:1709-1719.
Mazin, S.R. et al. (2010). "Emission-guided radiation therapy: Biologic targeting and adaptive treatment," Am. College of Radiology, pp. 989-990.
McMahon, R. et al. (2008). "A real-time dynamic-MLC control algorithm for delivering IMRT to targets undergoing 2D rigid motion in the beam's eye view," Med. Phys. 35:3875-3888.
Non-Final Office Action dated Dec. 6, 2019, for U.S. Appl. No. 15/993,325, filed May 30, 2018, 8 pages.
Notice of Allowance dated Jul. 25, 2019, for U.S. Appl. No. 16/046,746, filed Jul. 26, 2018, 8 pages.
Notice of Allowance dated Aug. 15, 2019, for U.S. Appl. No. 16/046,746, filed Jul. 26, 2018, 7 pages.
Olivera, G.H. et al. (2000). "Modifying a plan delivery without re-optimization to account for patient offset in tomotherapy," Proceedings of the $22^{nd}$ Annual EMBS International Conference, Jul. 23-28, 2000, Chicago, IL, pp. 441-444.
Papanikolaou, N. et al. (2010). "MU-Tomo: Independent dose validation software for helical tomo therapy," J. Cancer Sci. Ther. 2:145-152.
Parodi, K. (2015). "Vision 20/20: Positron emission tomography in radiation therapy planning, delivery, and monitoring," Am. Assoc. Phys. Med. 42:7153-7168.
Pyakuryal, A. et al. (2010). "A computational tool for the efficient analysis of dose-volume histograms for radiation therapy treatment plans," J Appl. Clin. Med. Phys. 11:137-157.
Rahmim, A. et al. (2009). "Four-dimensional (4d) image reconstruction strategies in dynamic pet: beyond conventional independent frame reconstruction," Medical physics 36:3654-3670.
Reader, A.J. et al. (2007). "Advances in pet image reconstruction," PET clinics 2:173-190.
Riederer, S.J. et al. (1978). "The noise power spectrum in computed x-ray tomography," Physics in medicine and biology 23:446.
ScandiDos (2019). Delta$^4$, located at https://delta4family.com/products, retrieved on Jul. 31, 2019, 5 total pages.
Seppenwoolde, Y. et al. (2002). "Precise and real-time measurement of 3d tumor motion in lung due to breathing and heartbeat, measured during radiotherapy," International Journal of Radiation Oncology Biology Physics 53:822-834.
Varian Medical Systems (2019). MOBIUS3D, Varian oncology software products, located at https://www.varian.com/oncology/products/software/mobius3d, retrieved on Jul. 31, 2019, 3 total pages.
Written Opinion of the International Searching Authority dated Nov. 16, 2018, for PCT Application No. PCT/US2018/039104, filed on Jun. 22, 2018, 6 pages.
Written Opinion of the International Searching Authority dated Oct. 3, 2018, for PCT Application No. PCT/US2018/035188, filed on May 30, 2018, 28 pages.
Written Opinion of the International Searching Authority dated Oct. 3, 2018, for PCT Application No. PCT/US2018/043954, filed on Jul. 26, 2018, 5 pages.
Yan, D. et al. (1997). "Adaptive radiation therapy," Physics Med. Biol. 42:123-132.
Extended European Search Report dated Feb. 3, 2021, for EP Application No. 18 810 297.4, filed on May 30, 2018, 4 pages.
Extended European Search Report dated Oct. 15, 2019, for European Application No. 17 764 132.1, filed on Mar. 9, 2017, 4 pages.
International Search Report dated Apr. 23, 2020, for PCT Application No. PCT/US2020/013927, filed on Jan. 16, 2020, 3 pages.
International Search Report dated Dec. 1, 2020, for PCT Application No. PCT/US2020/040774, filed on Jul. 2, 2020, 4 pages.
International Search Report dated Jun. 27, 2017, for PCT Patent Application No. PCT/US2017/021647, filed on Mar. 9, 2017, 3 pages.
Non-Final Office Action dated Jun. 26, 2020, for U.S. Appl. No. 16/122,735, filed on Sep. 5, 2018, 16 pages.
Non-Final Office Action dated Feb. 11, 2021, for U.S. Appl. No. 16/582,308, filed on Sep. 25, 2019, 9 pages.
Notice of Allowance dated Apr. 20, 2020, for U.S. Appl. No. 15/993,325, filed on May 30, 2018, 7 pages.

(56) References Cited

OTHER PUBLICATIONS

Notice of Allowance dated Dec. 11, 2020, for U.S. Appl. No. 16/122,735, filed Sep. 5, 2018, 10 pages.
Written Opinion of the International Searching Authority dated Apr. 23, 2020, for PCT Application No. PCT/US2020/013927, filed on Jan. 16, 2020, 4 pages.
Written Opinion of the International Searching Authority dated Dec. 1, 2020, for PCT Application No. PCT/US2020/040774, filed on Jul. 2, 2020, 8 pages.
Written Opinion of the International Searching Authority dated Jun. 27, 2017, for PCT Patent Application No. PCT/US2017/021647, filed on Mar. 9, 2017, 5 pages.

* cited by examiner

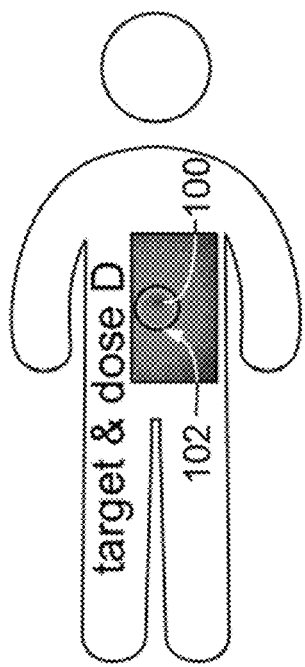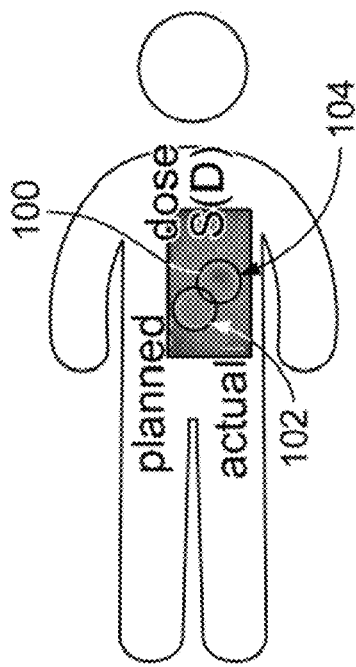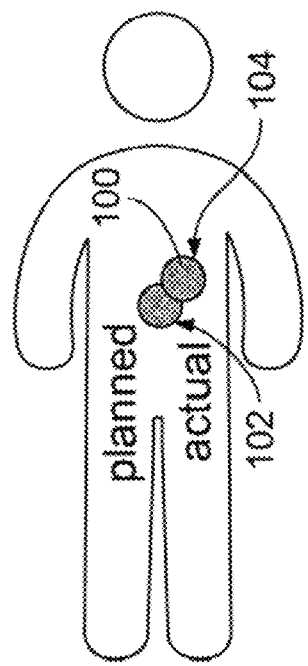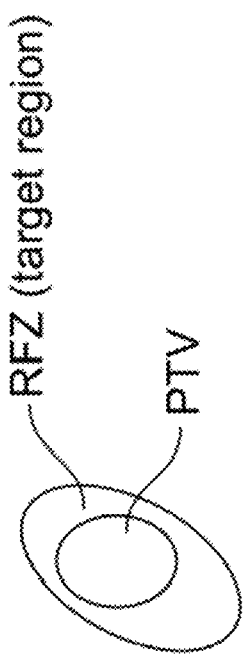

$$p = \mathrm{diag}(s) = \begin{bmatrix} 0 & 0 & 0 & 0 & s_{M-1} \\ 0 & 0 & 0 & \vdots & 0 \\ 0 & 0 & s_2 & 0 & 0 \\ 0 & s_1 & 0 & 0 & 0 \\ s_0 & 0 & 0 & 0 & 0 \end{bmatrix}$$

FIG. 2E $$p = \mathrm{toep}(f) = \begin{bmatrix} 0 & f_{-(M-3)} & \cdots & f_{-1} & f_0 \\ f_{-(M-3)} & \vdots & f_{-2} & \vdots & f_{-1} \\ \vdots & f_{-2} & f_0 & f_1 & \vdots \\ f_{-1} & f_0 & f_1 & \vdots & f_{M-3} \\ f_0 & f_1 & \vdots & f_{M-3} & 0 \end{bmatrix}$$

FIG. 2F

METHODS FOR REAL-TIME IMAGE GUIDED RADIATION THERAPY

CROSS-REFERENCE TO RELATED APPLICATIONS

This application is a continuation of U.S. patent application Ser. No. 15/993,325, filed May 30, 2018, now issued as U.S. Pat. No. 10,688,320, which claims priority to U.S. Provisional Patent Application No. 62/512,632, filed May 30, 2017 and U.S. Provisional Patent Application No. 62/537,384, filed Jul. 26, 2017, the disclosures of each of which are hereby incorporated by reference in their entirety.

TECHNICAL FIELD

Disclosed herein are systems and methods for guiding the delivery of therapeutic radiation using incomplete or partial images, and/or image data acquired during a treatment session.

BACKGROUND

Image guided radiation therapy (IGRT) uses images acquired before a treatment session to guide the application of therapeutic radiation during a treatment session. The goal of an IGRT system is to deliver precise dose of radiation to a stationary or moving target inside the patient and avoid irradiating organs-at-risk. This often includes generating a treatment plan that accounts for target motion before a treatment session, as well as gating or motion tracking during a treatment session (e.g., during radiation delivery). The treatment plan typically contains a fluence map or a segmented fluence map that accounts for radiation therapy machine geometry and a list of firing positions (also known as control points, which may be any locations from which a therapeutic radiation source may apply radiation to a patient), from which instructions to the radiation therapy system may be generated, so that the therapeutic radiation source emits radiation that generates a dose distribution that approximates or matches the dose distribution specified by the treatment plan. The machine instructions may include, for example, a set of beam intensities to be applied to the patient at each firing position (or a control point), and/or beam-limiting device instructions (e.g., multi-leaf collimator or MLC instructions) that indicate the MLC configuration for each of those firing positions. Some radiation therapy systems may have integrated imaging systems to aid in target motion tracking during a treatment session. Some treatment plans may generate and store the machine instructions directly, without generating a fluence map initially. However, it is generally understood that a set of machine instructions can be equivalently represented by a segmented fluence map together with radiation therapy machine geometry and a list of firing positions or control points.

Currently, radiation therapy systems that track the motion of a target region, do so by acquiring a high-SNR or high-resolution image of a target region using an imaging system, determining the location of the centroid of the target region, shifting the treatment plan fluence map according to backprojected shifts in the location of the target centroid, and delivering dose based on the shifted fluence map. That is, if a radiation target has shifted to the left (or right), the treatment plan fluence map is shifted such that the generated beam also shifts to the left (or right). These steps may be repeated in the duration of a treatment session. Some systems may use the changing target centroid location over time to generate a motion model to predict the future location of a target region, which may be used to gate the radiation beam delivery. Some systems create motion models that correlate surrogate marker motion with internal tumor motion, and use predicted tumor location (based on surrogate marker location) to shift the fluence maps.

However, these methods require that the acquired images $X_i$ are high-quality, high-SNR full or complete images (e.g., sufficient contrast data between the radiation target and the background of the image), otherwise the target centroid cannot be accurately calculated. Shifting a treatment plan's fluence map based on an imprecise or inaccurate target centroid location data may not improve the efficacy of the treatment plan, and may still result in the irradiation of non-target regions. Since high-quality images sufficient for centroid calculations often require several minutes of data acquisition, or cannot be acquired at sufficiently high frame rates (at least 1 or 2 images per second) due to imaging dose concerns (as in X-ray radiography or tomography), such images acquired during a treatment session do not provide real-time target location data upon which the radiation therapy system may act. The inability to update or correct the delivery of radiation to account for patient and/or tumor motion in real-time may result in radiation delivery to non-target regions.

SUMMARY

Disclosed herein are systems and methods for guiding the delivery of therapeutic radiation using incomplete or partial images and/or image data acquired during a treatment session. A partial image does not have enough information to determine the location of a target region due to, for example, poor or low contrast and/or low signal-to-noise ratio (SNR), but may be acquired quickly and frequently during the treatment session. The radiation fluence calculation methods described herein do not require knowledge or calculation of the target location, and yet may help to provide real-time image guided radiation therapy using arbitrarily low-SNR images. The low-SNR or partial images may be acquired just before (e.g., less than an hour, less than 30 minutes) and/or during a treatment session at a relatively high frame rate (e.g., at a rate that is similar to, or greater than, an average breathing rate, at least about 2 frames per second, at least about 4 frame per second, etc.). The imaging data provided in partial images, in combination with a radiation-firing matrix (RFM), which may be calculated as part of the treatment plan, may help to guide radiation delivery so that a prescribed radiation dose is delivered to the actual, real-time location of the target region(s) over the course of the treatment session. Optionally, some methods may comprise storing the partial images in a controller memory, and generating a full image by summing the partial images.

One variation of a method of image guided radiation therapy using partial images may comprise calculating a treatment plan including a radiation firing matrix based on tumor image data set with a sufficiently high SNR for identifying the tumor location and desired radiation dose to be delivered to the tumor. The RFM may be calculated in conjunction with a treatment plan. A treatment plan may be generated based on desired dose constraints and/or delineated target regions. The treatment plan and RFM may be calculated in advance of the treatment session, for example, minutes, days, weeks, and/or months before the treatment session. A method for IGRT may comprise acquiring a partial image or low-SNR image data of the tumor immediately before (e.g., minutes, seconds) and/or during a treatment session and calculating a real-time or updated fluence map by multiplying a RFM of the treatment plan and the partial image. A fluence map may include a set of beamlets and beamlet intensities to be applied to a patient. Radiation fluence computations may include calculations that compensate for imperfect contrast between the tumor and background structures (e.g., filtering or masking partial images). In some variations, masking or filtering partial images may comprise limiting the field-of-view (FOV) of the partial image to help reduce the effect of background structures. In some variations, masking or filtering a partial image may comprise removing regions of the partial image that do not correspond with the location of the tumor region (with or without a margin around the tumor region). That is, a mask may be applied to the partial image to extract the portion of the image that corresponds with the location of the target region or radiation-firing zone. The methods described herein may further comprise calculating a segmented fluence map from a fluence map, where the segmented fluence map includes multi-leaf collimator (MLC) instructions and/or therapeutic radiation source firing instructions for each firing angle or position. The radiation therapy system may then deliver radiation to the patient in accordance with the segmented fluence map for each firing angle or position.

A method for calculating a radiation fluence for delivery may comprise acquiring a partial image $x_i$ of a target region, and calculating a radiation fluence to be delivered to the target region by multiplying a radiation-firing matrix P and the partial image $x_i$. The radiation-firing matrix P may be calculated based on a full image X of a target region. The full image X may be acquired during a prior imaging session. In some variations, calculating the radiation fluence may comprise a point-wise multiplication or convolving radiation-firing matrix P with the partial image $x_i$. The radiation-firing matrix P may be a diagonal matrix of scalars s diag(s), such that $P \cdot x_i = s \odot x_i$, where $\odot$ is a point-wise product operation and results in a fluence to be delivered to the target region according to a treatment plan. Alternatively, the radiation-firing matrix P may be a Toeplitz matrix toep(f), such that $P \cdot x_i = f * x_i$, where * is a convolution operation and also results in a fluence. The signal-to-noise ratio (SNR) of the partial image $x_i$ is less than the SNR of the image X. In some variations, the partial image $x_i$ may be acquired using a tomographic imaging system. The partial image $x_i$ may comprise a reconstruction from a set of positron emission paths, X-ray projections, and/or sub-samples in k-space from a MM imaging pulse sequence. The image X may be a motion de-blurred image. The method may further comprise selecting a projection angle $\alpha$ and calculating a projected fluence $f_\alpha$ of the calculated fluence at a radiation beam firing angle $\alpha$ and storing it in a controller memory.

Optionally, a method may further comprise applying radiation to the target region, where applying radiation may comprise moving a radiation source of a radiation therapy system to a radiation beam firing angle $\alpha$, the radiation therapy system further comprising a multi-leaf collimator having an array of leaves disposed over the radiation source, segmenting the projected fluence $f_\alpha$ to collimator leaf position instructions and storing the leaf position instructions in controller memory, adjusting the position of each of the collimator leaves according to the collimator leaf position instructions, and emitting a radiation beam from the radiation source. The method may further comprise comprising continuously repeating the projected fluence $f_\alpha$ calculation and applying radiation to the target region after each fluence calculation, until a desired fluence is applied. Calculating the projected fluence $f_\alpha$ may comprise selecting a projection angle $\alpha$, calculating a projection $x_{i,\alpha}$ of partial image $x_i$ at the radiation beam firing angle $\alpha$ and storing the projected partial image $x_{i,\alpha}$ in controller memory, and multiplying a per angle radiation-firing matrix $P_\alpha$ with the projected partial image $x_{i,\alpha}$ ($P_\alpha$ $x_{i,\alpha}$), wherein the per-angle radiation-firing matrices $P_\alpha$. The per-angle radiation-firing matrices $P_\alpha$ may be Toeplitz matrices toep($p_\alpha$) that implement the convolution operation $p_\alpha * x_i$. The radiation-firing matrices $P_\alpha$ may be diagonal matrices diag($p_\alpha$) that implement a pointwise multiplication operation $p_\alpha \cdot x_i$. The partial image $x_j$ may be generated from a set of positron emission paths, X-ray projections, or sub-samples in k-space from a MM imaging pulse sequence. The method may optionally comprise applying a linear contrast filter to the partial image $x_i$. Any negative values of the filtered partial image $x_i$ may be added to a subsequent filtered partial image $x_{i+1}$. The signal-to-noise ratio (SNR) of the partial image $x_j$ is less than the SNR of the image X. Multiplying by the firing matrix P, selecting the projection angle $\alpha$, calculating projected fluence $f_\alpha$, moving the radiation source, segmenting the projected fluence $f_\alpha$ to collimator leaf position instructions and/or therapeutic radiation source firing instructions, adjusting the position of collimator leaves, and emitting a radiation beam may occur within a specified time period after acquiring the partial image $x_i$. The specified time period may be less than about 10 seconds, e.g., less than about 5 seconds, less than about 1 second. The radiation source may be mounted on a rotatable gantry configured to rotate at a speed of about 20 RPM or more (e.g., about 40 RPM, about 50 RPM, about 60 RPM or more). Methods may optionally comprise calculating a real-time delivered dose estimate, and/or comprising applying a spatial filter to the partial image $x_i$. Optionally, in some methods, the previously-acquired image X may be a first image and A may be a known dose calculation matrix, and the method may further comprise calculating an updated radiation-firing matrix $P_{prescan}$ by acquiring a second image $X_{prescan}$ and iterating through matrix values for $P_{prescan}$ such that the following conditions are met:

$$A \cdot P \cdot X \approx A \cdot P_{prescan} \cdot X_{prescan}$$

Some methods may optionally comprise calculating a dose matrix $D_{prescan}$ based on $X_{prescan}$, calculating a difference value between $D_{prescan}$ with a dose matrix D that has been calculated based on image X, and if the difference value exceeds a pre-selected threshold, generating a notification that the pre-selected threshold has been exceeded.

One variation of a system for radiation therapy may comprise a rotatable gantry, a therapeutic radiation source mounted on the gantry, one or more imaging sensors mounted on the gantry to acquire a partial image $x_i$ of a target region, and a controller in communication with the gantry, the therapeutic radiation source and the one or more imaging sensors. The controller may be configured to calculate a radiation fluence to be delivered to the target region, wherein calculating a radiation fluence comprises multiplying a radiation-firing matrix P and the partial image $x_i$, wherein the radiation-firing matrix P is calculated based on a previously-acquired image X of the target region. The radiation-firing matrix P may be a diagonal matrix of scalars s diag(s), such that $P \cdot x_i = s \lfloor x_i$, where $\lfloor$ is a point-wise product operation. Calculating the radiation fluence may comprise convolving the radiation-firing matrix P with the partial image $x_i$. The radiation-firing matrix P may be a Toeplitz matrix toep(f), such that $P \cdot x_i = f x_i$, where * is a convolution operation and f is a fluence to be delivered to the target region according to a treatment plan. The signal-to-noise ratio (SNR) of the partial image $x_i$ may be less than the SNR of the image X. For example, the SNR of the partial image $x_i$ may be about 40% less than the SNR of the image X The partial image $x_i$ may comprise a reconstruction from a set of positron emission paths, X-ray projections, or sub-samples in k-space from a MM imaging pulse sequence, and/or may be a motion de-blurred image. The controller may be further configured to select a projection angle α, calculate a projected fluence $f_\alpha$ of the calculated fluence at a radiation beam firing angle α and store the projected fluence $f_\alpha$ in a memory of the controller. The system may further comprise a multi-leaf collimator having an array of leaves disposed in a beam path of the radiation source, and the rotatable gantry may be configured to move the therapeutic radiation source to the radiation beam firing angle α, and the controller may be further configured to segment the projected fluence $f_\alpha$ to collimator leaf position instructions, store the leaf position instructions in controller memory. The position of each of the collimator leaves may be adjustable according to the collimator leaf position instructions. Calculating the projected fluence $f_\alpha$ may comprise selecting a projection angle α, calculating a projection $x_{i,\alpha}$ of the partial image $x_i$ at the radiation beam firing angle α and storing the projected partial image $x_{i,\alpha}$ in controller memory, and multiplying a per angle radiation-firing matrix $P_\alpha$ with the projected partial image $x_{i,\alpha}$ ($P_\alpha x_{i,\alpha}$). The per-angle radiation-firing matrix $P_\alpha$ may comprise a set of radiation-firing matrices $P_{i,\alpha}$ for each projection angle α. The per-angle radiation-firing matrices $P_\alpha$ may be Toeplitz matrices toep($p_\alpha$) that implement a convolution operation $p_\alpha * x_i$. The radiation-firing matrices $P_\alpha$ may be diagonal matrices diag($p_\alpha$) that implement a pointwise multiplication operation $p_\alpha \cdot x_i$. The one or more imaging sensors may comprise one or more PET detectors and the partial image $x_i$ is generated from a set of positron emission paths. Alternatively or additionally, the one or more imaging sensors may comprise one or more X-ray detectors and the partial image $x_i$ is generated from a set of X-ray projections, and/or the one or more imaging sensors may comprise one or more MM sensors and the partial image $x_i$ is generated from a set of sub-samples in k-space from a MRI imaging pulse sequence. The gantry may be configured to move the therapeutic radiation source to firing beam angle α and emit a radiation beam in accordance with the calculated fluence $f_\alpha$ within a specified time period after acquiring the partial image $x_i$. The specified time period is less than about 10 seconds, e.g., less than about 5 seconds, less than about 1 second, etc. The gantry may be rotatable at a speed of about 20 RPM or more, e.g., about 60 RPM or more. The controller may be further configured to apply a linear contrast filter to the partial image $x_i$, and/or any negative values of the filtered partial image $x_i$ may be added to a subsequent filtered partial image $x_{i+1}$. In some variations, the controller may be further configured to calculate a real-time delivered dose estimate. The controller may be further configured to apply a spatial filter to the partial image $x_i$. In one variation, the previously-acquired image X may be a first image and A is may be known dose calculation matrix, and the controller may be further configured to calculate an updated radiation-firing matrix $P_{prescan}$ by acquiring a second image $X_{prescan}$ using the one or more imaging sensors and iterating through matrix values for $P_{prescan}$ such that the following conditions are met:

$$A \cdot P \cdot X \approx A \cdot P_{prescan} \cdot X_{prescan}$$

The controller may be further configured to calculate a dose matrix $D_{prescan}$ based on $X_{prescan}$, calculate a difference value between $D_{prescan}$ with a dose matrix D that has been calculated based on image X, and if the difference value exceeds a pre-selected threshold, the controller may be configured to generate a notification that the pre-selected threshold has been exceeded.

Also described herein are methods for evaluating treatment plan quality. Methods for evaluating treatment plan quality may comprise powering on a radiation therapy system comprising a therapeutic radiation source, and a controller in communication with the therapeutic radiation source, where the controller comprises a processor and a memory with a treatment plan and positron emission activity data stored therein, and where the treatment plan comprises a radiation-firing matrix P and a planned fluence map, and the positron emission activity data comprises line-of-response (LOR) data, calculating a radiation fluence based on the radiation-firing matrix P and LOR data using the controller, emitting radiation using the therapeutic radiation source according to the calculated radiation fluence, measuring the emitted radiation, calculating a fluence map based on the measured radiation, calculating a fluence difference between the calculated fluence map and the planned fluence map, and generating a notification of whether the calculated fluence difference meets or exceeds a pre-specified fluence difference threshold. The radiation therapy system may further comprise a treatment area and the method may further comprise placing one or more radiographic films in the treatment area, and measuring the emitted radiation by analyzing the radiographic films. The radiation therapy system may further comprise a radiation detector located across from the therapeutic radiation source and in communication with the controller, and measuring the emitted radiation may comprise acquiring radiation data using the radiation detector and transmitting the radiation data to the controller. In some variations, positron emission activity data may comprise diagnostic PET imaging data, for example, spatially filtered diagnostic PET imaging data. A radiation therapy system may comprise an array of PET detectors having a detector field-of-view, and the spatially filtered diagnostic PET imaging data may have a field-of-view that corresponds to the detector field-of-view. Alternatively or additionally, the positron emission activity data may comprise a plurality of synthetic lines-of-response (LORs) generated based on diagnostic PET imaging data acquired on a PET imaging system and machine parameters of the PET imaging system. In some variations, the method may comprise adjusting the treatment plan if the calculated fluence difference exceeds the pre-specified fluence difference threshold. Adjusting the treatment plan may comprise updating the radiation-firing matrix P. The treatment plan may comprise a planned dose map, and the method may further comprise calculating a dose map based on the measured radiation, calculating a dose difference between the calculated dose map and the planned dose map, and generating a notification of whether the calculated dose difference meets or exceeds a pre-specified dose difference threshold. For example, generating a notification may comprise calculating a distance to agreement (DTA) value of fluence isodoses and an absolute dose difference between the calculated dose map and the planned dose map for multiple time points, and determining whether a percentage of time points that are within a DTA value and within a specified absolute dose difference threshold is greater than a threshold percentage. As an example, the threshold percentage may be about 95%, the DTA value may be about 3 mm, and the specified absolute dose difference threshold may be about 3% from a planned absolute dose.

Also described herein are systems and methods for real-time segmentation of fluence maps that are calculated based on imaging data acquired during a treatment session (e.g., partial images). One variation of a radiation therapy system may comprise a continuously rotatable gantry, a therapeutic radiation source mounted on the gantry and movable to a plurality of firing positions by the gantry, a multi-leaf collimator mounted on the gantry and located in a beam path of the radiation therapy source, one or more imaging sensors mounted on the gantry, and a controller in communication with the gantry, the radiation source, the multi-leaf collimator and the one or more imaging sensors. The controller may be configured to generate radiation delivery instructions by calculating a fluence map $f_{calc}$ using imaging data from the one or more imaging sensors and a cumulative residual fluence map $\Delta f_{cumulative}$, and segmenting the fluence map $f_{calc}$ into a set of radiation delivery instructions comprising MLC instructions and therapeutic radiation source instructions for each firing position over one or more gantry rotations. Each set of radiation delivery instructions may comprise instructions for the MLC and the therapeutic radiation source for each firing position over multiple gantry rotations. The one or more imaging sensors may comprise one or more PET detectors, and/or one or more imaging sensors comprises one or more X-ray detectors, and/or one or more MRI sensors. The multi-leaf collimator may be a binary multi-leaf collimator. MLC instructions may comprise leaf position instructions for each leaf in the MLC. Therapeutic radiation source instructions may comprise a beam pulse width, and/or a beam pulse intensity, and/or a number of beam pulses for each firing position. In some variations, segmenting the fluence map $f_{calc}$ may comprise deconstructing $f_{calc}$ into a sub-fluence map for each firing position, and segmenting each of the sub-fluence maps into radiation delivery instructions. The MLC may be a binary MLC, and each sub-fluence map may have a probability coefficient. Alternatively or additionally, the MLC is a binary MLC, and each leaf of the MLC may a probability coefficient that determines whether the leaf is in the open configuration and/or whether radiation is emitted by the therapeutic radiation source at a selected fluence level. In some variations, updating the cumulative residual fluence map $\Delta f_{cumulative}$ may comprise calculating a delivery fluence map $f_{delivery}$ based on the radiation delivery instructions, calculating an incremental residual fluence map $f_{increment}$ by subtracting the delivery fluence map $f_{delivery}$ from the fluence map $f_{calc}$, and updating the cumulative residual fluence map $\Delta f_{cumulative}$ by combining incremental residual fluence map $f_{increment}$ to the cumulative residual fluence map $\Delta f_{cumulative}$.

In some variations, the system may further comprise a plurality of sub-firing positions located between each of the firing positions, and the system may be configured to deliver radiation according the radiation delivery instructions corresponding to a firing position as the therapeutic radiation source passes over the sub-firing positions preceding the firing position. Segmenting the fluence map $f_{calc}$ may comprise deconstructing $f_{calc}$ into a plurality of sub-fluence maps for each sub-firing position, and segmenting each of the sub-fluence maps into radiation delivery instructions for each sub-firing position.

One variation of a method for real-time fluence map segmentation for radiation delivery may comprise acquiring imaging data from one or more imaging sensors mounted on a continuously rotatable gantry during a session, calculating a fluence map $f_{calc}$ using the imaging data and a cumulative residual fluence map $\Delta f_{cumulative}$, segmenting the fluence map $f_{calc}$ during the session into a set of radiation delivery instructions for one or more radiation firing positions over one or more gantry rotations. Radiation delivery instructions may comprise multi-leaf collimator (MLC) instructions and therapeutic radiation source instructions. Each set of radiation delivery instructions may comprise MLC instructions and the therapeutic radiation source over multiple gantry rotations. MLC instructions may comprise leaf position instructions for each leaf in the MLC. Therapeutic radiation source instructions may comprise a beam pulse width, and/or beam intensity, and/or a number of beam pulses for each firing position. Segmenting the fluence map $f_{calc}$ may comprise deconstructing $f_{calc}$ into a plurality of sub-fluence maps for each therapeutic radiation source firing position, and segmenting each of the sub-fluence maps into radiation delivery instructions. In some variations, the MLC may be a binary MLC, and each sub-fluence map may have a probability coefficient. Each leaf of a binary MLC may have a probability coefficient that determines whether the leaf is in the open configuration and/or whether radiation is emitted by the therapeutic radiation source at a selected fluence level. Optionally, the method may further comprise updating the cumulative residual fluence map $\Delta f_{cumulative}$ by calculating a delivery fluence map $f_{delivery}$ based on the radiation delivery instructions, calculating an incremental residual fluence map $f_{increment}$ by subtracting the delivery fluence map $f_{delivery}$ from the fluence map $f_{calc}$, and updating the cumulative residual fluence map $\Delta f_{cumulative}$ by combining the incremental residual fluence $f_{increment}$ to the cumulative residual fluence map $\Delta f_{cumulative}$. In some variations, a plurality of sub-firing positions may be located between each of the therapeutic radiation source firing positions and the method may further comprise delivering radiation according the radiation delivery instructions corresponding to a therapeutic radiation source firing position as the therapeutic radiation source passes over the sub-firing positions preceding the therapeutic radiation source firing position. Segmenting the fluence map $f_{calc}$ may comprise deconstructing $f_{calc}$ into a plurality of sub-fluence maps for each sub-firing position, and segmenting each of the sub-fluence maps into radiation delivery instructions for each sub-firing position. Optionally, some methods may comprise rotating the gantry to position a therapeutic radiation source mounted on the gantry at each firing position, and delivering radiation according to the radiation delivery instructions corresponding to each firing position. Acquiring imaging data and rotating the gantry may occur simultaneously. Acquiring imaging data and activating the therapeutic radiation source for radiation delivery may occur simultaneously. The one or more imaging sensors may be selected from a group consisting of: PET detectors, X-ray detectors, and MRI sensors.

BRIEF DESCRIPTION OF THE DRAWINGS

FIGS. 1A-1D depict a schematic representation of one variation of a method for IGRT.

FIG. 1E is a depiction of a radiation-firing zone (RFZ) or target region and a planning target volume.

FIG. 2E depicts one example of a radiation-firing matrix P.

FIG. 2F depicts one example of a radiation-firing matrix P.

DETAILED DESCRIPTION

Figure 1H:
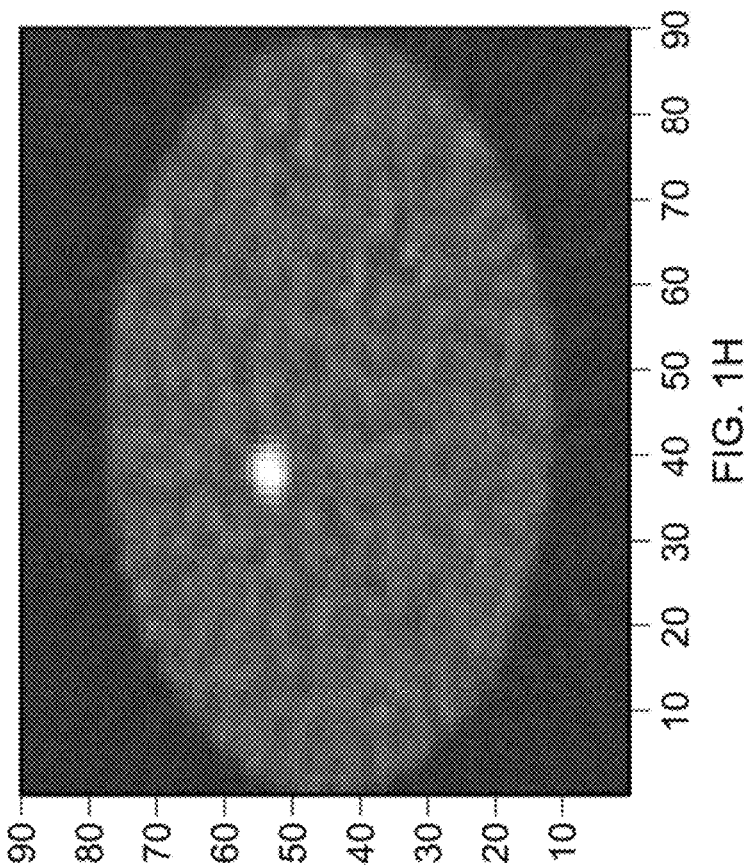
FIG. 1H depicts an example of a full PET image derived from summing the partial PET images of FIG. 1G.

Disclosed herein are systems and methods for guiding the delivery of therapeutic radiation using incomplete or partial images, and/or image data acquired during a treatment session. Some methods may comprise acquiring a partial image of a patient target region and multiplying it with a radiation-firing matrix. A radiation-firing matrix may be calculated during a treatment planning session based on the same data set used to calculate a treatment plan. The treatment plan may be previously generated using patient images acquired during a diagnostic imaging and/or prior treatment session. A treatment plan may contain a map or matrix that identifies one or more patient target regions (e.g., irradiation-target regions such as a planning target volume or PTV) and the desired radiation dose to be delivered to each of the one or more target regions. A radiation-firing matrix (RFM) may be a matrix that designates the conversion from partial images to a fluence map, which may include beamlet pattern (e.g., representing beamlets to be emitted by the therapeutic radiation source at various positions around the target regions) and/or beamlet intensities to be applied to the patient during a treatment session. A RFM may be used to generate a fluence map that specifies the radiation dose to be delivered to each patient target region. A fluence map may comprise a set of beamlets and beamlet intensities to be emitted at one or more firing angles (or firing positions) of a therapeutic radiation source (e.g., a linear accelerator or linac, and multi-leaf collimator) to deliver a prescribed radiation dose to one or more target regions. A fluence map may be converted to a set of radiation therapy system machine instructions (e.g., by segmentation) for execution by the radiation therapy system.

A treatment plan may contain one or more radiation-firing zones (RFZs), which may include a PTV and a margin around the PTV (as depicted in FIG. 1E). For example, a PTV may include a tumor region, and the margin around the PTV may account for location estimation errors of the PTV, and/or movement of the PTV or tumor region, and/or possible locations of the PTV or tumor region during radiation delivery, and/or geometrical changes to the tumor region. The treatment plan may also identify irradiation-avoidance regions, such as organs-at-risk (OARs), to which radiation exposure should be reduced or eliminated.

Also disclosed herein are radiation therapy systems configured to acquire real-time partial images during a treatment session and to dynamically vary radiation delivery to the patient based on a fluence map derived by multiplying a RFM with one or more acquired partial images. One variation of a radiation therapy system may comprise an imaging system configured to acquire one or more partial images or imaging data in real-time during a treatment session, such as one or more PET detectors, and/or an imaging radiation source with one or more X-ray detectors (e.g., an array of kV detectors and/or an array of MV detectors), and/or one or more MRI sensors. The radiation therapy system may also comprise a therapeutic radiation source and one or more radiation beam-shaping components disposed in the beam path of the therapeutic radiation source. The therapeutic radiation source and the beam-shaping components may be mounted on a motion system (e.g., gantry) configured to position the therapeutic radiation source, in real-time, with respect to a patient area. The beam-shaping components may be configured to change configurations in real-time in accordance with any real-time changes to the fluence map (e.g., change the size and/or shape of MLC apertures). The imaging system and the therapeutic radiation source may be configured such that the latency between the acquisition of a partial image and the corresponding radiation delivery to the patient is reduced, and in some variations, may be less than about 5 minutes, e.g., less than about 1 minute, less than about 45 seconds, less than about 30 seconds, less than about 20 seconds, less than about 10 seconds, less than about 5 seconds, less than about 1 second, less than about 500 milliseconds, etc.

Figure 4:
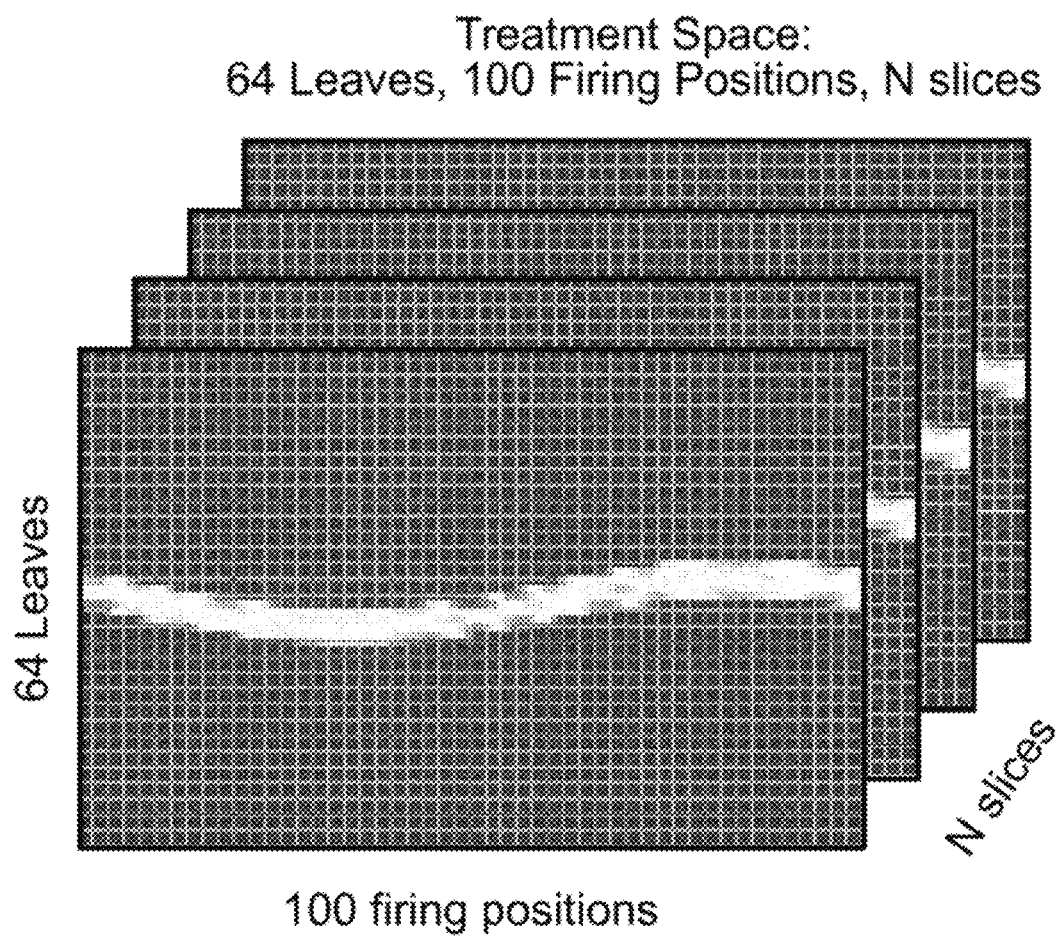
FIG. 4 depicts examples of sinograms for a radiation treatment system having 100 firing positions and a multi-leaf collimator with 64 leaves.

A RFM may be generated based on a treatment plan and multiplied with one or more partial images to calculate a fluence map. A fluence map may comprise a set of radiation beamlet weights (e.g., beamlet intensities) that may be segmented into a segmented fluence map, which can be used to generate a corresponding set of radiation therapy system instructions that would deliver radiation to the patient such that the delivered dose distribution corresponds to (i.e., matches or approximates) that specified in the treatment plan. FIG. 4 depicts one representation of a segmented fluence map for a system comprising a MLC with 64 leaves, a therapeutic radiation source with 100 firing positions, and N slices or patient platform positions (i.e., beam stations) in the radiation treatment system. Treatment planning may comprise calculating an initial estimated fluence map F and initial estimated dose distribution D based on the patient images and dose constraints. Upon acquisition of one or more partial images or imaging data at the start of and/or during a treatment session, the radiation-firing matrix may be multiplied and/or convolved with the partial images to generate a fluence map $F_i$, which may be used to guide radiation to the real-time location of the patient target region. One example of a multiplication operation is a point-wise multiplication operation such as diagonal matrix multiplication. One example of a convolution operation is a Toeplitz matrix operation. The fluence map $F_i$ may then be segmented to, for example, MLC instructions for radiation delivery. As described previously, the shape and location of patient target regions may change between the time the treatment plan was generated and the treatment session. The shape and location of patient and/or target regions may even change during a treatment session. Imaging data acquired during a treatment session may be used to calculate a fluence map so that the dose delivered to the patient target regions correspond with the dose distributions specified in the treatment plan, despite shape and/or location changes of target regions and/or OAR regions. The methods described herein modify and/or update the fluence map using partial (e.g., low-SNR) images. These partial images may be quickly (and in some variations, frequently) acquired during treatment, as compared to full images. Using partial images instead of full images may allow the fluence map to be modified or updated in real-time.

Partial Images and Full Images

Figure 1F:
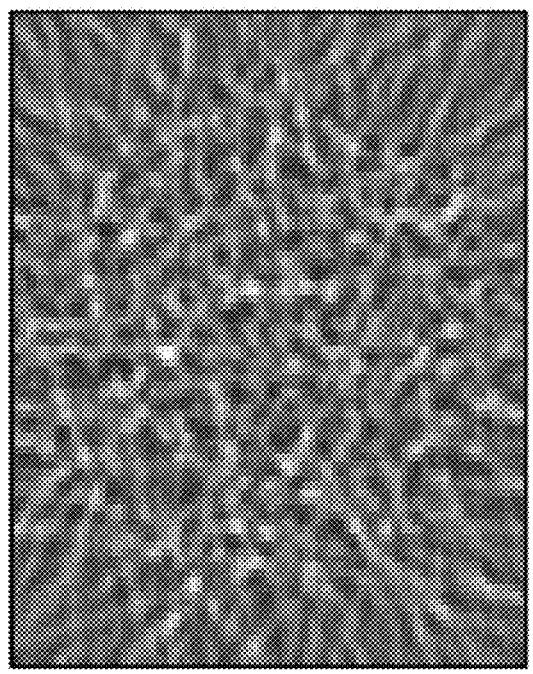
FIG. 1F depicts an example of a partial PET image.
Figure 1G:
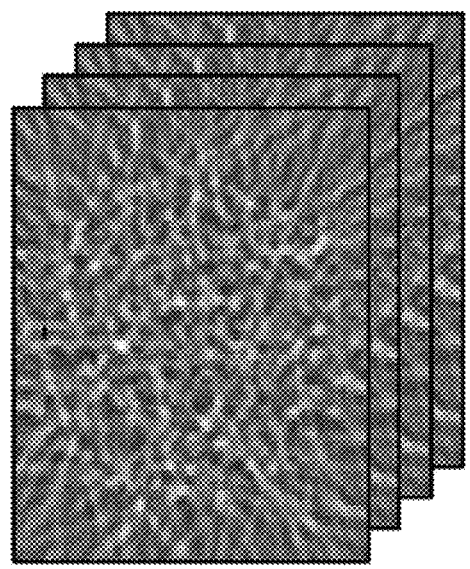
FIG. 1G depicts an example set of partial PET images.

A partial image may be any imaging data that has the linear property where the sum of a plurality of partial images yields a full image. A full image may have sufficient image data for treatment planning, target region delineation, target centroid calculations, and/or identification of anatomical structures or regions, while a partial image may not contain sufficient image data for these calculations or functions. Partial images acquired during a treatment session may have a lower-SNR than the image(s) from which the treatment plan is generated. More generally, the SNR of a partial image is less than the SNR of a full image. FIG. 1F depicts an example of a partial PET image, FIG. 1G depicts a set of partial PET images, and FIG. 1H depicts a full PET image that is a summation of a plurality of partial images, such as those in FIGS. 1F-1G. Each of the partial images in FIGS. 1F-1G was acquired in a 0.5 second time window, while the full image is constructed from partial images acquired in a 10 minute time window. The higher the SNR of a partial image, the fewer the number of partial images that needed to form to a full image. That is, since partial images with lower-SNR values (e.g., about 7% or less) have less image data than partial images with higher-SNR values (e.g., about 8% or more, about 10%), a greater number of low-SNR partial images are needed to form a full image as compared to high-SNR partial images. For example, a low-SNR partial image may have a thousandth ($1/1000$) of the image data of a full image (that is, the sum of about 1000 of such partial images would yield a full image). A higher-SNR partial image may have a hundredth ($1/100$), or a tenth ($1/10$) of the image data of a full image (that is, the sum of about 100 or 10, respectively, of such partial images would yield a full image). In some variations, a partial image may have a SNR that is at least about 30% less than the SNR of a full image. In some variations, a partial image may have a SNR that is about 40% less, or about 50% less, or about 55% less than the SNR of a full image. In still other variations, the SNR of a partial image may be about 0.18.

Alternatively or additionally, a partial image may comprise image data with a field-of-view (FOV) that is a subset or portion of the FOV of a full image. For example, a full image may comprise a 360 degree FOV while a partial image may comprise a portion of that FOV (e.g., about 30 degree FOV, about 45 degree FOV, about 50 degree FOV, etc.). In CT imaging, a partial image may comprise image data acquired from one or more low dose X-rays. A partial image may comprise a single slice or subset of a full tomographic scan (i.e., where the full image includes all of the slices in the tomographic scan) or a limited set of projections. A partial image may alternatively or additionally comprise the image data acquired within a time period that is shorter than the time period for acquiring image data for a full image. For example, if acquiring image data for a full image takes about five minutes, acquiring image data for a partial image may take about one minute or less, about 30 seconds or less, about 10 seconds or less, about one second or less. A partial image may be acquired in about 50% or less, about 40% or less, about 30% or less, about 20% or less, about 10% or less, about 1% or less, about 0.1% or less time than the acquisition time for a full image. In some variations, a full image may comprise a diagnostic image acquired in a pre-treatment or diagnostic imaging session to identify target region(s), including the size, shape, and location of target region(s). In some variations, a full image may comprise location and geometry data of a tumor. A plurality of full images of a tumor acquired over time may provide tumor motion data (e.g., tumor motion envelope). The sum of all partial images acquired just prior and/or during a treatment session may approximate a full image that may be acquired before or after the treatment session.

To summarize, a high-SNR image may be represented as full image X. An imaging system that operates in conjunction with a radiation therapy system (e.g., a radiation therapy system that has an on-board imaging system) may acquire or produce partial images $x_i$ at a faster frame rate than the frame rate for full image X, such that $$X = \Sigma x_i$$

In the context of PET imaging, a full 3D PET image may be obtained from millions of positron annihilation emission paths or individual positron emission lines-of-response or LORs (i.e., a line of response defined by a pair of coincident photons emitted by a positron annihilation event). The LORs may be backprojected into a 3D volume. Typical LOR acquisition rates are approximately 10,000 LORs/sec, hence requiring up to hundreds of seconds to obtain sufficient data for a full PET image of acceptable quality for treatment planning (typically including data from millions of LORs) or for identifying the shape and location of a patient target region and/or for calculating a target centroid location. A partial PET image may comprise any arbitrary incomplete set of LORs. For example, some methods may backproject LORs obtained every second into a partial 3D volume $x_i$. The sum of a plurality of these partial 3D volumes $x_i$ may be a full image $X (X = \Sigma x_i)$. A partial PET image may comprise a partial set of list-mode data. As depicted in FIGS. 1F-1G, such partial PET images may not have any visually discernible cues.

In the context of MRI imaging, a full 3D MRI image is obtained from thousands of acquired pulses from a MRI imaging pulse sequence. The sequences acquire individual lines of k-space in the Fourier domain. The lines in k-space may be assembled and interpolated into a series of 2D or 3D Cartesian Fourier spaces. In 2D acquisition, the slices are individual reconstructed using the inverse 2D FFT and then assembled into a 3D stack. In 3D acquisition, the direct 3D inverse FFT is applied and a 3D volume is reconstructed. A partial MM image may be sub-sampling in k-space or by a real-time 2D or 3D acquisition. Because of the linearity and noise properties of MRI, these partial images can be linearly combined to improve image quality.

In the context of CT imaging, a full 3D CT image may be obtained by acquiring 2D projection images (i.e., partial images) and backprojecting them into a 3D volume. Backprojection is a linear operator, hence an incomplete set of projections or even a single projection can be backprojected to obtain a partial 3D volume $x_i$, such that $X=\Sigma x_i$. Further, multiple low-dose (and low SNR) x-ray projection images may be summed to obtain a higher-SNR image. A partial CT image may comprise one or more 2-D projection X-ray images. In some variations, a partial CT image may comprise a single x-ray projection image, in contrast to a full image which may be a full field-of-view tomographic CT image. Adding up all of the x-ray projection images via a backprojection algorithm may yield the full CT image. In some variations, the x-ray dose may be progressively reduced as the treatment session proceeds, allowing a trade-off between patient dose and image guidance accuracy.

Typically, IGRT methods require the acquisition of full, high SNR images in order to calculate the centroid of target regions and/or generate motion models that are used to adjust radiation delivery. Partial, low SNR images may not provide sufficient data for these types of calculations. The methods described herein, however, adjust radiation delivery based on fluence maps calculated using partial images acquired in real-time, and emitting radiation at a set of beam angles with a set of multi-leaf collimator instructions. That is, when partial images are combined with the radiation-firing matrix contained in a treatment plan, an up-to-date fluence map may be provided for radiation delivery such that the radiation therapy system delivers the prescribed dose to a target region that has moved (and/or may continue to move). In some variations, combining a partial image with a radiation-firing matrix may comprise multiplying the partial image with the radiation-firing matrix to derive an updated (i.e., up-to-date) fluence map. The updated fluence map may then be converted or segmented into a segmented fluence map which may be associated with a set of MLC leaf configurations and/or therapeutic radiation source firing instructions. In some variations, segmenting the updated fluence map may comprise calculating MLC configurations for each firing position (e.g., firing or beam angle).

Radiation-Firing Matrix

A radiation-firing matrix (RFM) may be a matrix that designates the conversion from partial images to a fluence map that may include beamlet pattern and/or beamlet intensities to be applied to the patient during a treatment session. A RFM may represent the relationship between a fluence map F for radiation delivery to a patient region and an image X of that patient region. That is, a radiation-firing matrix P may be any matrix such that $F=P\cdot X$. A RFM may be calculated during a treatment planning session in conjunction with calculating a fluence map that minimizes one or more cost functions, for example, a cost function C(D, F) of a resulting dose distribution D and fluence F, formed based on the radiation dose constraints and objectives described and depicted in FIG. 2A, and optional limitations on F. Examples of cost functions may include, but are not limited to, minimum dose to target region, average or maximum dose on OARs, and/or fluence smoothness, total radiation output, total tissue dose, treatment time, etc. In some variations, generating a radiation-firing matrix P may comprise setting up an optimization problem for minimizing the cost function C(D, F), and iterating through different sets of P such that the cost function C(D, F) is minimized while the following conditions are met:

$$F=P\cdot X \text{ and}$$

$$D=A\cdot F=A\cdot P\cdot X;$$

where D is the predicted dose distribution, A is a pre-calculated dose calculation matrix, F is the predicted total delivered radiation fluence, and X is a known full image (e.g., an image acquired during a diagnostic imaging session and/or previous treatment session). The predicted dose distribution D and the predicted radiation fluence F may be calculated using dose constraints, PTV, ROI, and/or OAR data, and a patient CT image (e.g., as described and depicted in FIG. 2A). One example of a dose calculation matrix A may be a (k×n) matrix where n may be the number of candidate beamlets $\{b_i\}$ and k may be the number of pre-selected voxels for a radiation-firing zone (RFZ). An i-th column of the dose calculation matrix A (which has k elements) represents a dose contribution from a unity-weighted beamlet $b_i$ to each of the k voxels.

Dose calculation matrix A may be calculated column-by-column, for example, by ray-tracing each beamlet's aperture along the path through a RFZ or patient volume and calculating the contribution of a unity-weighted beamlet to each of the k voxels. A beamlet aperture may be a MLC aperture defined by a single MLC leaf opening (i.e., of a binary MLC or a 2-D MLC). Examples of dose calculation algorithms that may be used in any of the methods described herein may include Monte-Carlo simulation, collapsed-cone convolution superposition, pencil-beam convolution, and others.

The radiation-firing matrix P may be a matrix that, when multiplied by the full image X, yields the predicted or desired delivered radiation fluence F that minimizes the cost function. The cost function may be convex, allowing the use of well-known convex optimization algorithms, such as gradient descent, fast proximal gradient method, or interior-point methods. The calculated radiation-firing matrix P may represent a multiplication factor that relates fluence F to the full image X This relationship may be used during a treatment session to update fluence f at a particular time point based on a partial image $x_i$ acquired at that same time point by multiplying the partial image with the radiation-firing matrix P (e.g., $f_i=P\cdot x_i$).

In contrast, typical treatment planning does not include the calculation of a radiation-firing matrix. Treatment planning usually comprises forming an optimization problem for minimizing a similar cost function C(D, F) formed from the desired constraints and objectives described herein, and iterating through different sets of F (without using P) such that:

$$D=A\cdot F$$

Typical treatment planning does not have any additional condition or requirement that fluence F is to be related to the full image X via a radiation-firing matrix such as $F=P\cdot X$. That is, typical treatment planning calculates fluence F without any consideration of a multiplication factor that relates the fluence F to the full image X Fluence Map A radiation therapy system may comprise a therapeutic radiation source, such as a linear accelerator (linac), and one or more beam-limiting components, such as jaws and/or a dynamic multi-leaf collimator, both of which may be mounted on a motion system configured to move the radiation source and associated beam-limiting components about a patient area. A fluence map may comprise a set of beamlet intensities and firing positions (e.g., firing angles) that may be used by a radiation therapy system to position a radiation source and to control the intensity and shape of the generated radiation beam such that a selected/prescribed dose of radiation is applied to a RFZ while limiting the amount of radiation applied to one or more organs-at-risk or OARs (e.g., irradiation-avoidance volumes). A beamlet may be a portion of a full radiation beam from the therapeutic radiation source, where the beamlet is defined by a multi-leaf collimator leaf opening at a particular firing position with respect to a patient area. A beamlet has a fluence level that may be determined at least in part by the size of the multi-leaf collimator leaf opening (e.g., the length and width of a collimator leaf, and/or the number of collimator leaves in an open configuration, and/or position of one or more collimator leaves along its travel path between a completely open configuration and a closed configuration), and/or radiation intensity per therapeutic radiation source pulse, and/or the number of pulses fired when the therapeutic radiation source is located at a particular firing position. In some variations, the therapeutic radiation source may emit radiation pulses having discrete intensity levels (e.g., fluence levels), and the number of radiation pulses may be determined at least in part by the maximum firing rate of the therapeutic radiation source and the amount of time the therapeutic radiation source is located at a firing position. For example, in some radiation therapy systems, the therapeutic radiation source may be a linac that fires radiation pulses at two intensity values (e.g., half intensity and full-intensity, or 0.5 and 1). The linac may be mounted on a continuously rotating gantry where the time duration the linac is at any particular firing position and the firing rate of the linac are such that the linac may fire two pulses at each firing position. In this example, at each firing position, for each beamlet defined by a single binary multi-leaf collimator leaf, there may be five discrete fluence levels: 0 (no pulses fired at all), 0.5 (one pulse fired at half intensity), 1 (one pulse fired at full intensity or two pulses fired at half intensity), 1.5 (a first pulse fired at full intensity and a second pulse fired at half intensity), and 2 (two pulses fired at full intensity).

In some variations, a fluence map may be segmented to minimize the number of required MLC or other beam-shaping component configurations required deliver the fluence map. Based on an updated (segmented) fluence map calculated by multiplying a radiation-firing matrix and one or more partial images acquired in real-time, the motion system may be configured to move the therapeutic radiation source and/or components of the collimation subsystem to deliver the desired dose distribution to the patient. In some variations, the therapeutic radiation source may be mounted on a rotatable gantry and the motion system may continuously rotate the therapeutic radiation source through each of the firing positions (e.g., firing angles about the circular gantry). A fluence map may specify the beamlet(s) that are emitted to the RFZ or patient region by the therapeutic radiation source as it moves to, and/or moves through, each firing position.

Methods

Variations of methods for calculating radiation fluence maps using partial image data acquired just before and/or during a treatment session are described below.

Turning now to the figures, FIG. 1A represents a diagnostic imaging session where images of the patient and/or target region(s) are acquired using any imaging modality. Examples of imaging modalities may include X-ray images (e.g., CT images), MRI, PET, ultrasound, etc. The acquired images may have sufficiently high SNR such that the size, shape and location of anatomical features and the target regions, as well as the relative positioning of the target regions to patient anatomical features may be identified. A radiation-firing zone (RFZ) may be selected and delineated based on these images. As an example, the RFZ may include a PTV (100), located at a first location (102), is delineated in the image. In some variations, a RFZ may include one or more regions of interest, for example, a tumor region, and/or a tumor region with a motion envelope that represents the region around a tumor within which the tumor may move (e.g., a planned target volume or PTV (100)). Based on the images acquired during a diagnostic imaging session where the PTV (100) is at the first location (102), a treatment planning system may generate a treatment plan. The treatment plan may include a desired dose distribution D to be delivered to the PTV(s) and/or RFZ(s) identified in the images from the diagnostic imaging session. FIG. 1B depicts one example of a dose distribution D to the PTV (100) as defined in a treatment plan. For example, a treatment plan may comprise a dose map D with high-dose regions corresponding to the first location (102), which is where the PTV (100) was located in the diagnostic images. In some variations, a treatment plan may also define radiation-sensitive regions of a patient (e.g., organs-at-risk or OARs) to which radiation exposure should be limited or minimized. Optionally, a radiation-firing matrix P and/or a fluence map may be generated as part of the treatment plan.

In the time period between the diagnostic imaging session and a treatment session, the PTV (100) may have moved from the first location (102). In some cases, the PTV (100) may continue to move during the treatment session. During radiation treatment delivery, the position of the PTV (100) may move periodically, for example, due to breathing motion and patient's shift on the couch. FIG. 1C depicts a situation where the PTV (100) has moved from the first location (102) (which is where it was during the diagnostic imaging session) to a second location (104).

The systems and methods described herein may calculate an updated (i.e., up-to-date) fluence map for delivery to a patient based on partial or low SNR images acquired during a radiation treatment session. These methods may comprise acquiring partial or low SNR images and/or image data at the beginning of and/or during a treatment session, and multiplying the radiation-firing matrix P with the partial images and/or image data to derive an updated fluence map. The updated fluence map may be segmented to a segmented fluence map, which may comprise a set of MLC configurations and radiation source positioning and/or firing instructions. When radiation is delivered according to the updated (segmented) fluence map, the desired radiation dose may be delivered to the target region, even if the target region has shifted after treatment planning and/or before and/or during treatment. FIG. 1D conceptually depicts the delivered dose distribution when radiation is delivered in accordance with the methods described herein, where radiation delivery is based on an updated fluence map that has been calculated by multiplying the radiation-firing matrix P and partial images and/or partial image data acquired at the time of treatment. Even though the treatment plan was calculated based on the PTV (100) being located at the first location (102), radiation may be delivered to the actual location of the PTV during the treatment session (i.e., second location (104)).

Figure 2A:
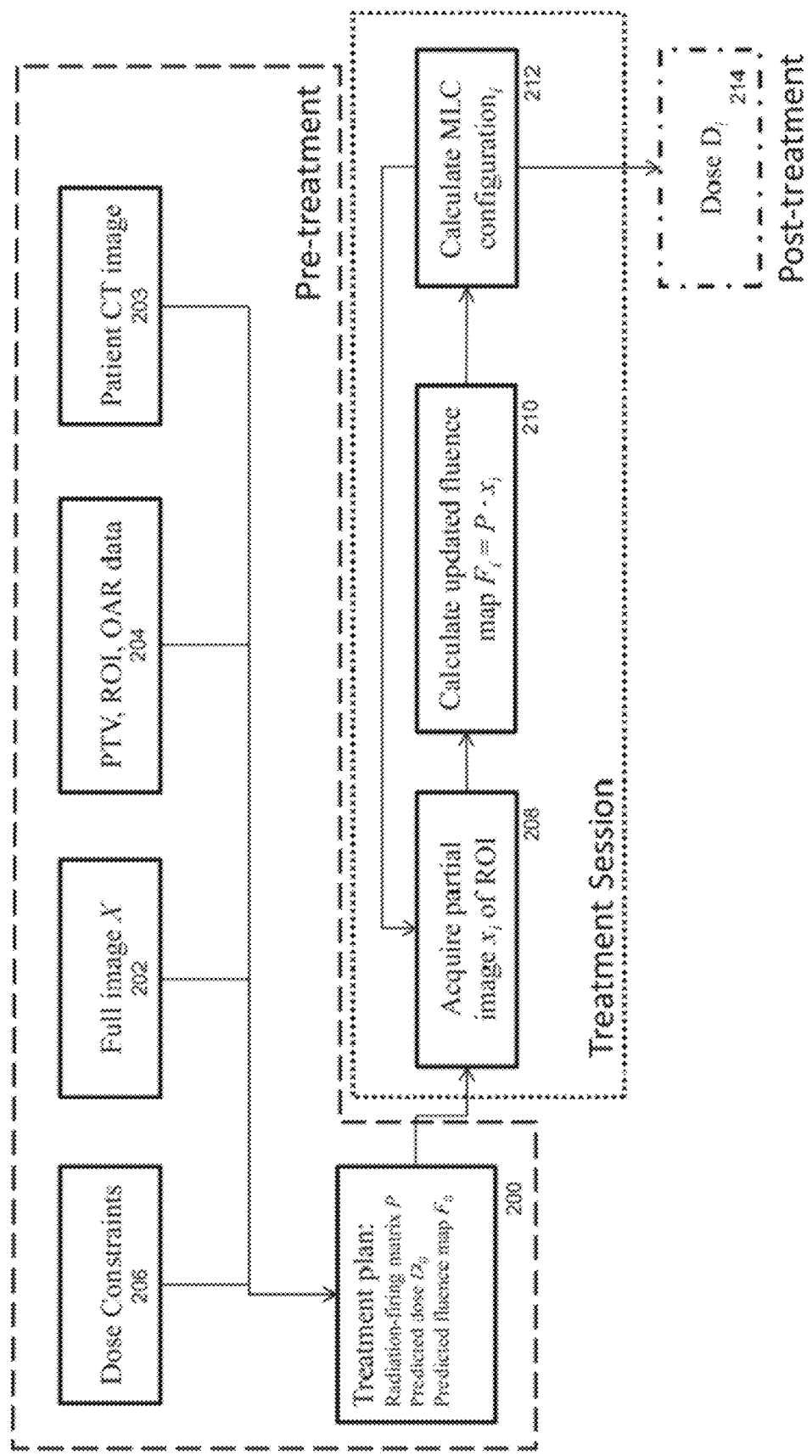
FIG. 2A depicts a block diagram of one variation of a method for delivering therapeutic radiation to a moving patient target region using partial image data acquired during a treatment session.
Figure 2B:
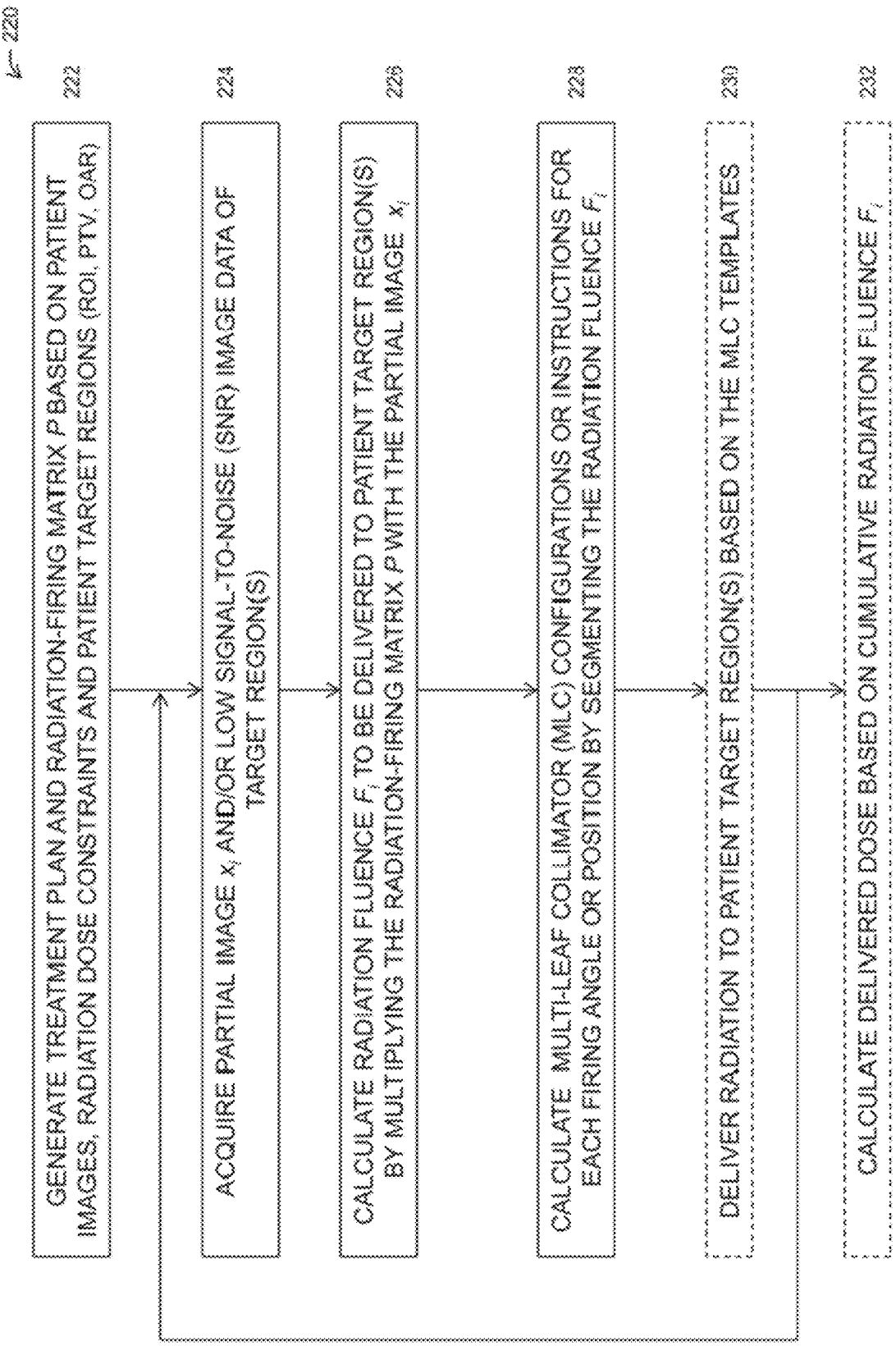
FIG. 2B depicts a flowchart diagram of one variation of a method for calculating a radiation fluence for delivery based on partial image data acquired during a treatment session.

FIG. 2A is a functional block diagram of one variation of a method for image-guided radiation therapy based on partial images and FIG. 2B is a flow chart diagram of a method for calculating a radiation fluence using partial images for image-guided radiation therapy. As depicted in FIG. 2A, a treatment plan (200) may be calculated prior to a treatment session. The treatment plan may comprise a radiation-firing matrix P (200) that may be calculated based on, for example, one or more full or complete images X (202) and/or a patient CT image (203). RFZ (e.g., target regions and/or PTVs) and/or OARs may be identified or outlined using the full or complete images X and/or the patient CT image, and/or other supplemental patient images in the same frame of reference. This information may also be used to calculate the radiation-firing matrix P. Additional data (204) regarding the RFZ(s) and/or OARs such as their size, shape, location, and degree of radiation-sensitivity, maximum tolerable radiation exposure, and/or a prescribed radiation dose to be delivered to irradiation-target regions, and/or other dose constraints (206) such as maximum and minimum dose delivered for each patient target region may also be used in the calculations of a RFM. The patient CT image (203) may also be used for dose calculations, for example, predicting the distribution of the delivered dose Do if radiation were applied to the patient according to the radiation-firing matrix P.

On the day of a treatment session or fraction, the radiation fluence delivered to the patient may be updated based on image data acquired just before and/or during the treatment session. Optionally, at the start of a treatment session (such as the set-up phase of the treatment session), a patient pre-scan image $X_{prescan}$ may be acquired. Image data from the pre-scan image $X_{prescan}$ may be used to update the radiation-firing matrix P just prior to radiation delivery (for example, by multiplying by a scalar factor). In some variations, the pre-scan image $X_{prescan}$ may be compared to the full image X If the pre-scan image $X_{prescan}$ and the full image X are substantially different (e.g., large changes in target region location and/or shape), a clinician may determine that the radiation treatment is not suitable for delivery to the patient and the treatment session may be paused or canceled. In some variations, the fluence map predicted during planning phase F=P·X may be compared to the fluence map predicted using the pre-scan image $F_{prescan}$=P·$X_{prescan}$ in order to modify the radiation-firing matrix P so that $F_{prescan} \approx F$, or pause or cancel the treatment session, referring the patient to a repeated treatment planning step. In some variations, the dose map predicted during the planning phase D=A·P·X may be compared to the dose map predicted using the pre-scan image $D_{prescan}$=A·P·$X_{prescan}$ in order to modify P so that $D_{prescan} \approx D$, or pause or cancel the treatment session, referring the patient to a repeated treatment planning step.

Proceeding to the radiation-delivery portion of the treatment session, as depicted in FIG. 2A, radiation delivered to the patient may be updated by acquiring (208) a partial image $x_i$, and calculating (210) an updated fluence map $F_i$ by multiplying the radiation-firing matrix P and the partial image $x_i$. Partial images can be one-, two-, three- or higher-dimensional images. The updated fluence map $F_i$ may have dimensions that are independent of the dimensions of the partial image $x_i$. $F_i$ and may be one-, two-, three-dimensional or higher-dimensional. Dimensions of $F_i$ may correspond with the machine parameters or configurations of the treatment system. For example, a 3D partial image may be 256 pixels by 256 pixels by 50 pixels, while the (3D) fluence map may be 100 pixels by 64 pixels by 50 pixels, corresponding to a treatment system having 100 firing positions and a one-dimensional multi-leaf collimator with 64 leaves, and using 50 possible couch stop positions, or alternatively corresponding to a treatment system with 100 firing positions, and a two-dimensional multi-leaf collimator with 64 leaf pairs, and 50 unique allowable couch (i.e., patient platform) stops. Due to potentially different dimensionality and size, the radiation-firing matrix P is generally rectangular, and it is assumed that multiplication with P is performed on $x_i$ linearized into a 1D vector form using column-major or row-major ordering. The resulting fluence map may be linearized, and can be reshaped back from a 1D vector into its proper N-dimensional form. Image-guided radiation therapy methods may optionally comprise segmenting the fluence map $F_i$ (which may have dimensions that correspond to the machine configuration) in order to calculate MLC configurations$_i$ (212). A segmented fluence map may comprise a set of MLC and radiation source positioning and/or firing instructions to deliver beamlets to one or more RFZs as specified by the fluence map. The radiation therapy system may then configure the linac and MLC in accordance with the calculated MLC configuration (e.g., by moving the linac and MLC to a firing position and adjusting MLC leaf positions, and optionally moving the couch) to emit radiation fluence as specified by the fluence map $F_i$. Optionally, at the end of a treatment session or after the treatment session, the cumulative dose $D_t$ may be calculated (214) as $D_{treatment} = \Sigma D_i$. In some variations, dose $D_i$ may be calculated based on data from a radiation detector of the radiation therapy system, such as a radiation detector (e.g., MV detector) located across from the therapeutic radiation source (e.g., a linac).

The total delivered treatment session dose can be further analyzed using the linearity of the matrix multiplication and the fact that partial images add up to the full image $X_{treatment} = \Sigma x_i$, hence $$D_{treatment} = \Sigma D_i = \Sigma A \cdot P \cdot x_i = A \cdot P \cdot \Sigma x_i = A \cdot P \cdot X_{treatment}$$

In some variations, an image acquired just before treatment (e.g., in a prescan) may be used to estimate the dose to be delivered during the treatment session. When little or no anatomical changes occur between the time of prescan and the treatment session, the predicted delivered dose at prescan may approximate the actual delivered dose.

FIG. 2B summarizes one variation of a method (220) for continuously updating radiation fluence in image-guided radiation therapy using a RFM and one or more partial images. The method (220) may comprise generating (222) a treatment plan including a radiation-firing matrix P based on one or more patient images, radiation dose constraints and objectives, and patient target regions (e.g., RFZ, PTV or irradiation-target regions, OAR or irradiation-avoidance regions).

In some variations, a treatment plan and radiation-firing matrix may be calculated based on patient target region data, including the size, shape, location, degree of radiation-sensitivity of RFZs and/or PTVs and/or OARs, and radiation dose constraints and objectives. Radiation dose constraints may include, for example, maximum tolerable radiation exposure and/or a prescribed radiation dose to be delivered to irradiation-target regions or PTVs, and/or may include a desired radiation dose distribution, which may be determined by a controller under the guidance of a clinician and/or user (such as a medical physicist or technician). Radiation dose objectives may include, for example, identifying and/or delineating OARs which should be maximally spared of radiation. Generating a treatment plan may optionally comprise calculating a predicted dose distribution D and determining whether it satisfies the desired dose constraints and objectives. Generating a treatment plan and radiation-firing matrix P may be performed before a treatment session and/or at the start of a treatment session.

The patient images may be full images from which the patient target regions (e.g., PTVs), radiation-firing zones (RFZs) and/or OARs are identified and/or delineated. For example, one of the patient images can be designated as the primary image guidance image X The image X may be equal to the sum of partial images, i.e., $X=\Sigma x_i$.

Method (220) may comprise acquiring (224) one or more partial images and/or low SNR image data $x_i$, which may be used to calculate (226) an updated fluence map F to be delivered to the patient tumor region(s) by multiplying the radiation-firing matrix P with the partial image $x_i$. The partial image $x_i$ may optionally be masked or filtered to include only the area(s) within the RFZ(s). In some variations, a multiplication of the radiation-firing matrix P and the one or more acquired partial images $x_i$ may be equivalent to convolving a certain linear FIR filter f and a partial image $x_i$, or a point-wise multiplication of a scaling vector s a partial image. For example, as depicted in FIGS. 2E and 2F, in these cases, the radiation-firing matrix P may be expressed as a Toeplitz matrix toep(f), or may be expressed as a diagonal matrix diag(s), respectively. Multiplying a Toeplitz radiation-firing matrix P=toep(f) with an acquired partial image $x_i$ may be expressed as a convolution $P x_i = f*x_i$ and multiplying a diagonal-shaped P=diag(s) with a partial image is equivalent to a point-wise multiplication $P x_i = s \odot x_i$. The radiation-firing matrix P may have any number of columns and rows other than what is depicted in FIGS. 2E and 2F. Method (220) may comprise segmenting (228) the updated fluence map $F_i$ into MLC configurations and/or radiation beam emission instructions for each firing angle or position. For example, radiation beam emission instructions for a radiation therapy system comprising a rotatable gantry, a linac and a dynamic MLC (e.g., binary or 2D MLC) mounted on the gantry may comprise a matrix that indicates the beamlet pattern or beamlet intensities to be emitted or fired by the linac and dynamic MLC at every firing angle. Radiation beam instructions may also comprise a set of beamlets (e.g., beam intensities and/or beam pulses, etc.) applied sequentially to the patient in order to deliver the fluence specified by the fluence map $F_i$. Method (220) may optionally comprise delivering (230) radiation to the patient target region(s) based on the MLC templates and/or radiation beam emission instructions (e.g., linac intensity and/or pulse instructions), as well as optionally calculating (232) delivered dose (i.e., radiation dose distribution delivered in accordance with the calculated radiation fluence from step (226)) using radiation detector (e.g., MV detector) data. Steps (224)-(230) may be repeated and/or replicated for multiple target regions or RFZs until the treatment session ends (e.g., per clinician or patient command, or when radiation delivered to all patient target regions reaches the level specified by the treatment plan, etc.).

Although the variations described herein may be in the context of applying radiation to a single target region, it should be understood that these systems and methods may be used to apply radiation to any number of target regions, and/or any number of tumor regions or regions of interest in general. As described above, a target region may include irradiation-regions such as PTVs and irradiation-avoidance regions such as OARs. A radiation-firing zone (RFZ) may include a PTV and a margin around the PTV.

Some variations of method (220) may comprise preprocessing the images used for image-guidance. One variation of a method may comprise applying a linear preprocessing transform T to full image X prior calculation of P in step (222), and apply the same preprocessing transform T to each acquired partial image in step (224). If X* is the original unmodified image, and the original partial images are $x_i^*$, then the image used in treatment planning step would be (222) is X=T(X*), and the partial images used in (226) are $x_i=T(x_i^*)$. The linearity of the transform ensures that the sum of preprocessed partial images is still equal to the preprocessed full image, as shown below:

$$\Sigma x_i = \Sigma T(x_i^*) = T(\Sigma x_i^*) = T(X^*) = X$$

In some variations T may be non-linear, and the dose and fluence prediction equations may need to be updated based on this.

Some variations of method (220) may comprise improving the image contrast in full images used for image-guidance using a contrast-enhancing filter (CEF) as a preprocessing step, e.g. a difference of gaussians (DoG) finite impulse response image filter. One variation of a method may apply a linear CEF to a full image prior to calculation of P, and apply the same CEF to each acquired partial image prior to fluence calculation (e.g., prior to multiplying the partial image by P). If X* is the original unfiltered image, and the original partial images are $x_i^*$, then the image used in treatment planning step (222) is X=CEF(X*), and the partial images used in (226) are $x_i$=CEF ($x_i^*$). The linearity of the filter ensures that the sum of CEF filtered partial images is still equal to the filtered full image, as shown below:

$$\Sigma x_i = \Sigma CEF(x_i^*) = CEF(\Sigma x_i^*) = CEF(X^*) = X$$

Some variations of calculating a fluence map based on partial images acquired in real-time just before and/or during a treatment session may optionally comprise steps for removing background anatomical structures (e.g., anatomical clutter, such as bony structures, and the like) and other such noise that may be present in the partial image. Some variations may comprise masking out only a certain radiation-firing zone (RFZ), e.g., target region with an additional expansion, from the full and partial images, which can be done by using a preprocessing step T which comprises a point-wise multiplication of an image with a binary mask image, containing 0s in pixels outside of the RFZ, and is in pixels inside the RFZ. The RFZ of interest (e.g., in a fixed frame of reference) may contain the entire possible range of motion of the tumor, including regular and dynamic breathing motion, as well as irregular motion. Examples of irregular motion may include, but may not be limited to, patient shifts while on the couch, couch deflections due to patient shifts and/or weight, and setup error. In some variations, preprocessing step T comprises, a masking operation and a contrast enhancing filter. High contrast may be more easily achieved in a localized area of an image, for example, in the vicinity of the target itself, e.g. within the radiation-firing zone (RFZ).

In some cases unmodified partial images, or partial images preprocessed with T, may contain negative values because the expected delivered fluence in $F_i=P\cdot x_i$ may be negative, and negative radiation fluence may not be delivered. The methods described herein which use one or more partial or low SNR (e.g., noisy) images, partial images may optionally be added to form the full image. A simple truncation or thresholding of negative values that appear in the partial image will render the property $X=\Sigma x_i$ invalid, and modify the predicted dose equation $D=A\cdot P\cdot X$, possibly making it dependent on individual partial images, and/or shifting the mean, and/or modifying the equation in other ways. In order to preserve the partial image sum property and the predicted dose equation, in some variations, "negative fluence" or "negative beamlets" may be maintained forward in the next fluence map computation, which may, for example, may cancel future delivered fluence that may have otherwise been fired. One example of such "carry forward" algorithm is given below:

1. Initialize $C_0=0 \cdot F$, i.e., a zero matrix of same dimension as fluence.
2. Imaging system acquires a partial (low-SNR) image $x_i^*$, the image is preprocessed to form $x_i=T(x_i^*)$ and may contain negative values.
3. Fluence $F_i$ is formed $$F_i = |P \cdot x_i + C_{i-1}|_+$$
$$C_i = |P \cdot x_i + C_{i-1}|_-$$

Above $$|x|_+ = \begin{cases} x, & x > 0 \\ 0, & x \leq 0 \end{cases}$$

$$|x|_- = \begin{cases} 0, & x > 0 \\ x, & x \leq 0 \end{cases}$$

when applied to a vector it is applied element-wise.

4. Fluence is segmented and delivered using the radiation source.
5. Steps 2-4 may be repeated until a desired or prescribed dose is delivered to the RFZ or target region.

The same method can be applied to a positive maximum threshold. The partial images may be truncated to a predetermined positive threshold. Any intensity above the maximum threshold may be carry-forwarded to the next partial image.

Dose Variability Calculations

Optionally, the expected delivered dose may be calculated based on a full image. Due to variations in setup, imaging conditions, internal organ motion, biological variations and others, reimaging the patient just prior to a treatment session (e.g. during "prescan") may yield a full image $X_{prescan}$ that is different from the image X used in planning. Hence, the expected delivered dose $D_{prescan}$ may also be different from D presented at the planning step, which may have been used to secure clinician approval. To avoid requiring a new clinician approval, in some variations, the calculated/predicted dosimetric outcome (at treatment planning time) may include a probabilistic distribution that represents a range of dose variability (e.g., mean and standard deviation, or as full probability distributions). The variabilities may be generated for total delivered MU, and individual DVH curves. The variability calculations may be based on the expected and/or worst-case expected variations in the full image between a full image $X_{prescan}$ and the image X used in planning. This range of dose variability may be reviewed and approved by a clinician prior to a treatment session and as long as the calculated dose variations at the time of treatment are within the approved range, the treatment session may proceed.

For example, in a radiation therapy system comprising an imaging system that includes PET detectors (e.g., biologically-guided radiotherapy or BGRT system), the calculated/predicted dosimetric outcome may account for the inherent stochastic nature of PET imaging, variability in patient's biology and PET uptake and standard uptake value (SUV), patient setup errors and other factors. The expected differences between the full images $X_{prescan}$ and X can be calculating by mapping the expected variations into the image space. For example, the SUV variation of ±20% may be modeled as the image variation (X±0.2 max(X))/1.2. The noise inherent in PET imaging using filter-backprojection reconstruction can be modeled as X+N(X), where N is the Gaussian noise function. All known variabilities may be mapped into the image space, and the resulting dose variability can be derived using probabilistic models and the fact that $D=A \cdot P \cdot X$.

Methods for Fluence Map Delivery by Projection Views

A radiation therapy system may deliver radiation fluence on a projection angle-by-projection angle basis to attain a desired dose distribution for the patient. A projection angle or view of a fluence map at a radiation beam firing angle or position may be the portion the fluence map that is aligned with that particular firing angle or position. Delivery of the entire fluence map may be achieved via a sum of contributions of separate fluence maps for each projection view. Given an image I, a projection of the image onto a view α may be a linear operation $R_\alpha(I)$. The linearity of the projection operator means that there may be a homomorphism between the space of images and their projections, which may preserve the relationship between them. The definition of partial images may be preserved in the projection space:

$$X = \sum_i x_i$$

$$R_\alpha(X) = R_\alpha\left(\sum_i x_i\right) = \sum_i R_\alpha(x_i)$$

This may be used to formulate radiation delivery using any of the methods described herein for a beam-by-beam (or projection view-by-view) delivery system that operates on partial projected images. Full and partial images may be denoted as:

$$X_\alpha = R_\alpha(X)$$

$$x_{i,\alpha} = R_\alpha(x_i)$$

A treatment plan may contain a separate radiation firing matrix $P_\alpha$ for each view α, calculated using the corresponding projection of the full image $X_\alpha$ for each view α, where each view α may be a firing position or angle. As described further below and depicted in FIG. 5, multiplied with projected partial image gives the fluence map that corresponds to the firing angle (or view) α. Since P is a matrix that maps partial images to fluence maps, the fluence maps and partial images may be grouped based on their firing angle α. In this way, the matrix P can be arranged as a block-diagonal matrix from a set of separate radiation firing matrices $P_\alpha$ for each firing angle, which maps projected partial images to fluence maps for the same firing angle. For example, for n firing angles (i.e., firing angles α):

$$P = \begin{bmatrix} P_1 & \cdots & 0 \\ \vdots & \ddots & \vdots \\ 0 & \cdots & P_n \end{bmatrix}$$

This may correspond to a partial image-guided radiation therapy method that operates separately from all projections α. If a partial image $x_{i,\alpha}$ is obtained at a projection a, the radiation delivery device may be able to quickly delivery radiation dosage corresponding to the fluence map $P_\alpha \cdot x_{i,\alpha}$ for that projection. This may be attained with any of the radiation treatment systems described herein.

Figure 5:
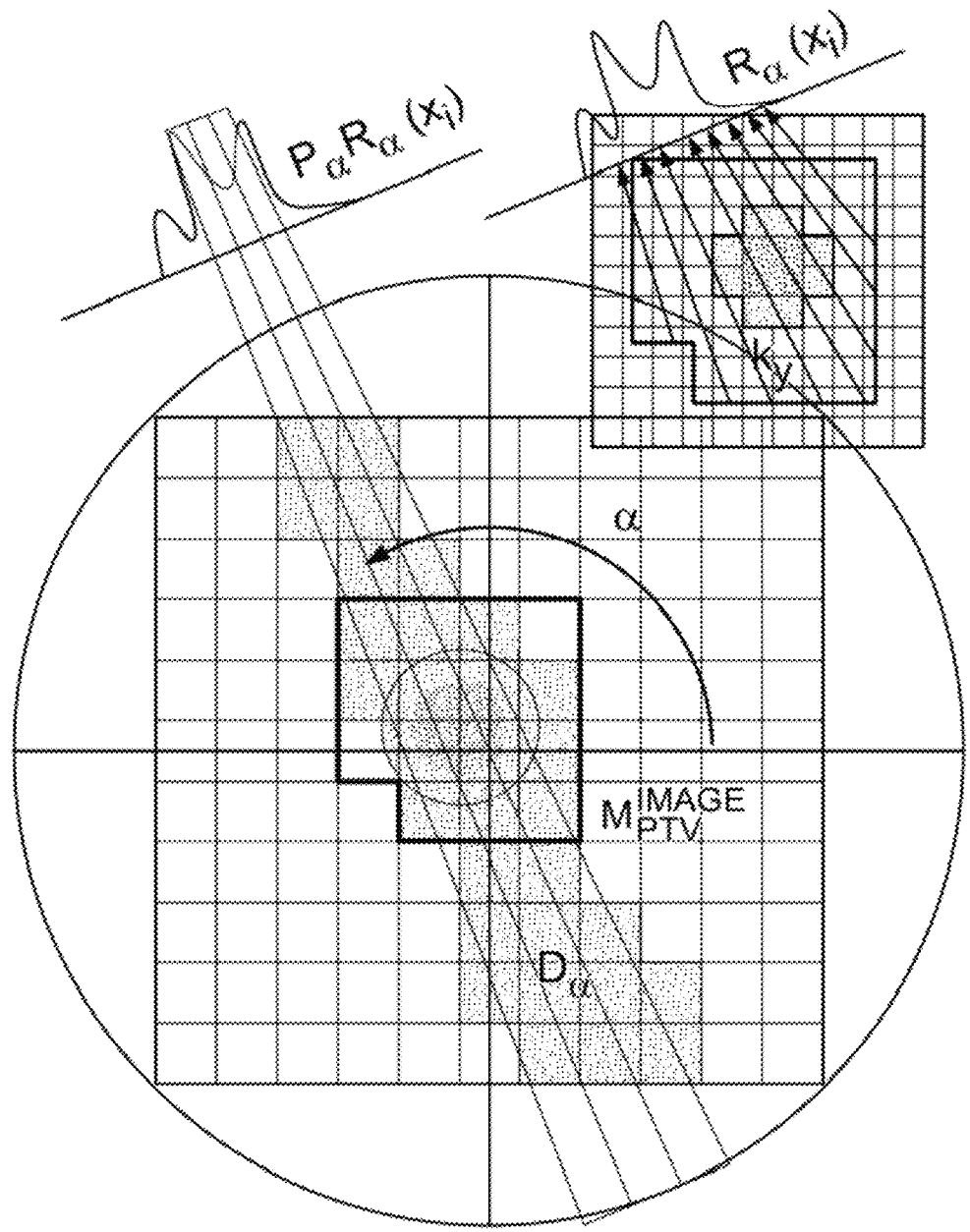
FIG. 5 depicts a plot that conceptually represents a method of image guided radiation therapy using partial images.

FIG. 5 depicts one variation of a method of image-guided radiation therapy using partial PET images, which may help to improve contrast in sinogram projection by masking the partial image in the image space and convolving with the treatment plan (e.g., convolving with a RFM of a treatment plan). This method may comprise collecting a PET tomographic dataset over a selected time window, reconstructing a partial PET image $x_i$, masking the partial PET image $x_i$, forward projecting the masked partial PET image to a given firing position, multiplying with a radiation-firing matrix, segmenting fluence into discrete MLC leaves at particular firing positions and patient platform locations, and back-projecting radiation from the firing position. The equation listed in FIG. 5 depicts a mathematical representation of the dose delivered in firing angle or view $\alpha$ (e.g., from the frame of reference of a radiation source located at firing angle $\alpha$). The linear operator K represents the process of reconstructing the PET projection data y using filter-backprojection and masking the resulting image by the PTV mask. The linear operator $R(\alpha)$ describes the process of forward projection of the masked partial image $K_y$ to the view $\alpha$. The projection estimate is multiplied by the RFM P at view $\alpha$ (i.e., $P_\alpha$) to generate the fluence that is delivered by the radiation therapy system. The matrix A may be a linear operator that maps fluence to dose in the image space. The equation described in FIG. 5 is an embodiment that can be used to map measured PET data y into dose. The operators described in FIG. 5 are linear operators with respect to the PET measurement y and the dose D. The linearity property may allow for the matrix P to be optimized on the full image, but delivered on the partial images.

Methods for Real-Time Fluence Map Segmentation

Fluence maps may be delivered as a combination of beamlets fired separately, e.g., at different firing positions and/or with different MLC configurations and/or therapeutic radiation source emission properties (e.g., pulse width, pulse intensity, pulse frequency, pulse number, etc.). Segmentation is the process by which a fluence map is translated into beamlets and/or radiation delivery instructions. Fluence maps that are calculated and/or adjusted in real-time (i.e., during a treatment session) based on imaging data (e.g., partial image data) acquired during the treatment session may be segmented in real-time into discrete fluence levels and/or beamlets, so that the desired or planned fluence may be delivered to the current location and/or geometry of the target region. For example, an updated fluence map may be segmented into discrete fluence levels and/or beamlets while the therapeutic radiation source and gantry are continuously rotating and delivering radiation to the patient. Reducing the latency between the detection of target region location and/or geometry may help facilitate more precise and accurate radiation delivery to target regions, even as they move during the treatment session.

In some variations, a radiation treatment planning method comprises calculating the radiation fluence such that the delivered radiation meets the treatment goals and objectives (e.g., such as organ-at-risk sparing and target(s) coverage and minimum dose). While such fluence map (i.e., planned fluence map) may indicate the fluence to be delivered at each firing position (or control point) in light of the limitations of the geometry and/or motion of the gantry and/or robotic arm(s) upon which the therapeutic radiation source is mounted, the planned fluence map may not include specific radiation therapy system instructions (e.g., MLC leaf configurations, radiation source beam pulse parameters, etc.). As a treatment session starts, radiation delivery instructions may be generated by segmenting the planned fluence map and used to operate the radiotherapy system hardware. However, as imaging data is acquired during the session, the planned fluence map may be updated based on that data and/or be replaced by a fluence map calculated based on the acquired imaging data. The radiation therapy system may then segment the updated or calculated fluence map into radiation therapy system instructions, which may allow for the delivery of arbitrary-shaped radiation fluence in response to a real-time imaging signal (e.g., partial images or noisy imaging signals acquired during the treatment session that may reflect the real-time location of the target region).

Figure 6A:
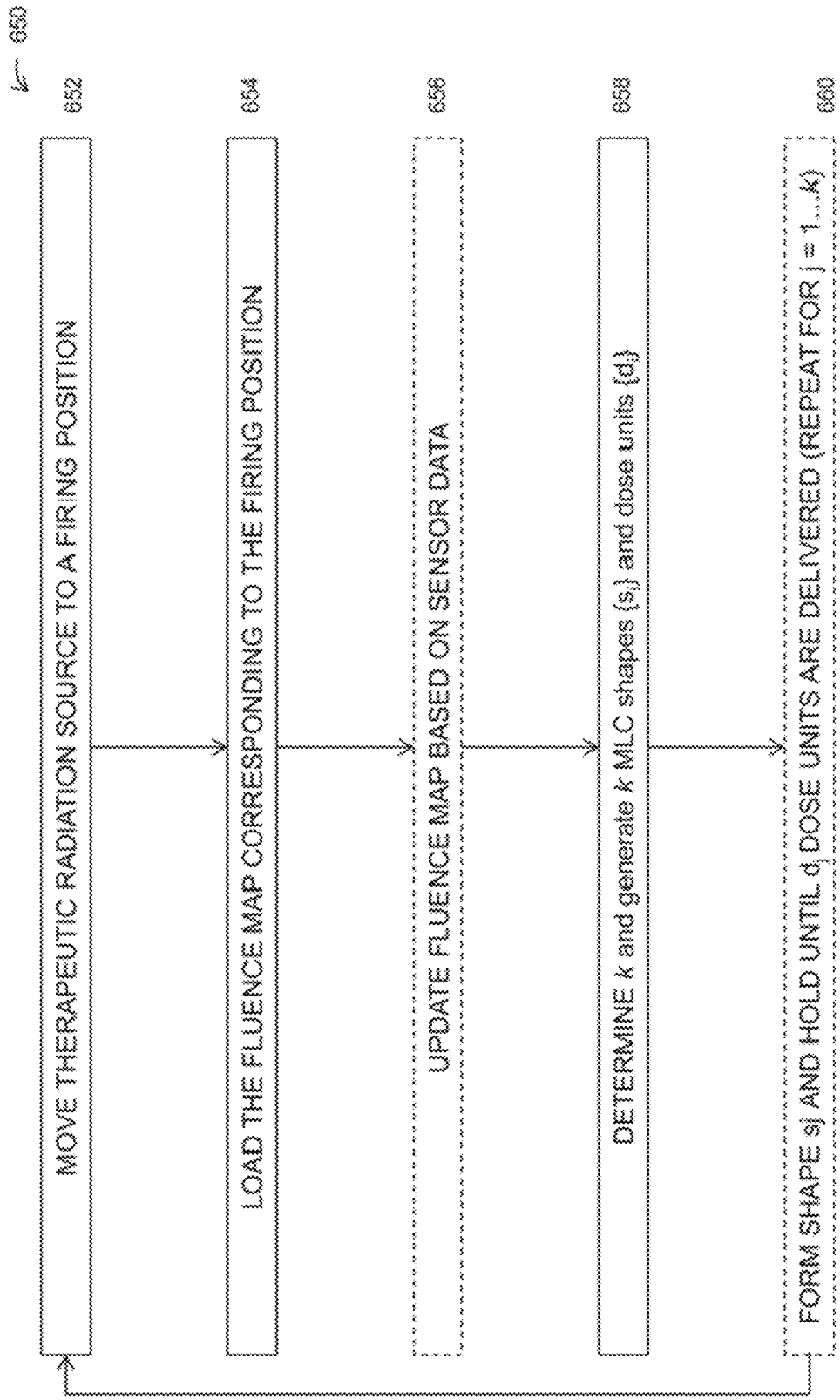
FIG. 6A depicts a flowchart representation of one variation of a method for delivering radiation based on a fluence map that has been calculated/updated in real-time during a treatment session.

In some variations, the radiation fluence for each firing position or control point may be updated during the treatment session, and/or the cumulative fluence map (i.e., the sum of all radiation fluence over all firing positions or control points may be updated. Modifying radiation delivery based on a real-time signal may facilitate radiation delivery to the target region despite any target motion and/or deformation. While the examples herein describe real-time segmentation using PET imaging data, it should be understood that real-time segmentation may use imaging data of any modality, e.g., X-ray fluoroscopy, MR, ultrasound and the like. The fluence map and corresponding segmentation into radiation delivery instructions and/or beamlets may take place once per firing position, or once per several firing positions or control points, etc. Each time the fluence is updated, it may be converted to MLC configurations or apertures (i.e., apertures formed by opening/closing leaves of the MLC in a specified configuration) and/or other delivery commands for one or more firing positions or control points to deliver the desired fluence. FIG. 6A is a flowchart representation of a method of real-time segmentation during a treatment session. While the examples herein are described in the context of a radiation therapy system with a continuously rotating circular gantry with firing positions at particular angles around the circumference of the gantry and a movable patient platform that translates within a bore of the gantry, it should be understood that one or more of these method steps may be applicable to radiation therapy systems of any gantry type (e.g., C-arm, robotic arm, circular gantry that moves along arc segments, etc.) that may have any number of control points at any location about the patient and/or radiation therapy system isocenter.

The steps depicted in the method (650) may be repeated throughout a treatment session. Method (650) may comprise moving (652) the therapeutic radiation source to a firing position, loading (654) the fluence map corresponding to the firing position, updating (656) the fluence map based on imaging or other sensor data (if needed), determining (658) a series of k MLC aperture shapes and/or other collimation component configurations $\{s_j\}$ and corresponding dose units $\{d_j\}$, and adjusting the MLC (660) and/or other collimation components to have the aperture shapes/configurations $\{s_j\}$ to deliver the dose units $\{d_j\}$ repeatedly over j=1 . . . k.

In some variations, the therapeutic radiation source may be held stationary at the firing position as the MLC is adjusted through all k aperture shapes. The number of aperture shapes k may be a fixed or predetermined parameter, and/or may be based on a maximum fluence level of a fluence map, and/or may be determined at least in part on the geometry complexity of a fluence map. In some examples, the number of aperture shapes k may be less than about 100, less than about 50, less than about 20, less than about 10, less than about 4, and/or less than about 2. In other variations, going through all of the k configurations may require k rotations of the therapeutic radiation source through all firing positions, adjusting the MLC to only one desired configuration at each firing position upon every rotation, in order to deliver the total prescribed dose. In other variations, the therapeutic radiation source may continue moving as the MLC is adjusted through all k configurations over k sub-firing positions located in-between the firing positions, as long as total desired dose over k configurations can be delivered before the radiation source is positioned at the next firing position. Method (650) may be repeated at each discrete patient platform position (i.e., beam station, location at which the platform is stopped or not moving), or may be repeated as the patient platform moves continuously through the therapeutic radiation beam path.

However, as with any segmentation of a fluence map into radiation therapy system instructions, there may be differences between the planned fluence map and the radiation fluence that is deliverable by the system (i.e., fluence discrepancies or deviations resulting in a fluence residual, or segmentation errors) due to a variety of factors, including, but not limited to, machine geometry constraints (e.g., number, size, speed, range of motion, and/or shape of MLC leaves), and/or system capability constraints (e.g., therapeutic radiation source firing rate, pulse width, timing and synchronization constraints). Segmentation errors may arise when discretizing a continuous fluence map into a segmented fluence map comprised of discrete fluence levels. Such fluence segmentation errors may be due to imperfect segmentation and imperfect dose calculation (e.g., precise MLC leaf configurations may not be known at time of the treatment planning dose calculation). For example, while the MLC leaves may closely approximate the shape of the fluence to be delivered from a particular firing position, there may be small differences between the shape of the MLC aperture attained by MLC leaf configuration and the shape of the fluence that is intended to be delivered. Another example of a factor that may contribute to segmentation errors is that a fluence map for a particular firing position may not be deliverable with an integer number of MLC leaf configurations and/or at the segmented fluence levels. That is, the fluence deliverable at a firing position may be a discrete fluence level that is deliverable with a single MLC leaf configuration and/or therapeutic radiation source pulse width or number and the calculated fluence map may designate a fluence level that cannot be discretized without a remainder or residual quantity of fluence. Furthermore, depending on the architecture of the therapeutic radiation source, the number of segmented fluence levels may be limited, and as a result, the calculated fluence map may not be discretized into segmented fluence levels without a fluence remainder or residual.

When segmentation occurs before a treatment session, these segmentation errors can be mitigated by identifying the target regions affected by these fluence deviations or segmentation errors and adjusting the radiation therapy system instructions over the entire treatment session to deliver any differences in fluence. For example, fluence deviations or segmentation errors can be compensated by reweighting the dose levels associated with the all of the MLC leaf configurations, across the entire treatment plan. To mitigate the dose calculation errors, the treatment planning system may perform additional dose calculations after calculating the exact MLC leaf configurations, in order to model leaf edge effects properly. However, in a treatment session where radiation treatment is based on imaging data acquired in real-time, the cumulative fluence map deliverable by the system for an entire treatment session is not known, since the fluence map from the treatment planning system is continuously and/or dynamically being updated based on real-time data. As radiation treatment proceeds during the session, the segmentation errors may accumulate and result in an unacceptable dose delivery profile over time. Real-time segmentation cannot use traditional methods to compensate for this, and may include other methods to mitigate imperfect segmentation and dose calculation inaccuracies. Furthermore, in the course of real-time fluence map updates, the updated fluence map may include fluence values that are not deliverable by the radiation source at the next firing position. This may result in a residual fluence that may be carried over into the next fluence map update for another (e.g., future) firing position. For example, the residual fluence may be delivered by (repeatedly) emitting radiation from the therapeutic radiation source at the same firing position.

One method for real-time segmentation and mitigation of segmentation errors during a radiation treatment session may comprise calculating a fluence map $f_{calc}$ using imaging data acquired in real-time and a residual fluence map $\Delta f_{residual}$. The fluence map that is updated may be a fluence map calculated during treatment planning. The residual fluence map $\Delta f_{residual}$ may be an aggregate of segmentation errors and fluence deviations incurred during the treatment session preceding the calculation of the fluence map $f_{calc}$. In some variations, the fluence map for delivering at a particular firing position may be calculated by updating a fluence map corresponding to that firing position before the therapeutic source is moved to that firing position. The calculated fluence map $f_{calc}$ may be segmented into radiation delivery instructions deliverable at that firing position over one or more gantry rotations. Some methods may comprise calculating and updating the residual fluence map $\Delta f_{residual}$ throughout the treatment session (e.g., once per firing position, once per gantry rotation, etc.). Each set of radiation delivery instructions may be system/machine instructions, for example, MLC instructions (e.g., MLC apertures shapes attained by MLC leaf configurations, leaf position instructions for each leaf in the MLC, etc.) for each firing position over one or more gantry rotations, and therapeutic radiation source instructions for each firing position over one or more gantry rotations (e.g., beam pulse width, number of beam pulses to be fired at each firing position, firing probability coefficient for each firing position or sub-firing position, and/or firing probability coefficient for each MLC leaf at each firing position or sub-firing position). The radiation beam pulse width, and the number of pulses per firing position may be selected to approximate or match the fluence that is to be delivered at that firing position.

A radiation therapy system may be configured to help mitigate segmentation errors and/or fluence deviations or remainders that may occur when a fluence map is discretized by comprising a therapeutic radiation source that may emit radiation at a number of discrete fluence levels. In some variations, having an increased number of discrete fluence levels may help the radiation therapy system segmentation process to generate a segmented fluence map that more closely approximates the updated fluence map, which may help to lower fluence remainders or residuals. For example, a radiation therapy system comprising a therapeutic radiation source and a dynamic binary multi-leaf collimator both of which are mounted on a fast-rotating circular gantry (e.g., rotating at about 60 RPM to about 70 RPM) may have at least two discrete fluence levels since each leaf can either be open or closed at a firing position. Additional discrete fluence levels may be added if the therapeutic radiation source can fire two or more pulses at each firing position, and/or if the radiation pulse width can be adjusted to two or more widths. For example, a radiation therapy system having a binary multi-leaf collimator that can fire up to two pulses at each firing position, at two possible pulse width values for each pulse may have five discrete fluence levels (0, 0.5, 1, 1.5, 2) for discretizing a fluence map. In some variations where the therapeutic radiation source may fire radiation pulses while being moved between firing positions (e.g., at a sub-firing position located between two firing positions), additional discrete fluence levels may be available for discretizing a fluence map with continuous fluence values to a segmented fluence map with discrete fluence levels. The fluence map can be segmented with more accuracy, if the multi-leaf collimator can change its configuration at each sub-firing position.

One or more variations of methods for real-time segmentation and mitigation of segmentation errors during a radiation treatment session may comprise assigning a firing probability coefficient (i.e., probability coefficient) for a particular beamlet at a particular firing position (or sub-firing position). The firing probability coefficient (i.e., probability coefficient) specifies the likelihood that the therapeutic radiation source will fire that beamlet and/or the likelihood that the therapeutic radiation source will fire a beamlet at a particular fluence level at a firing position or sub-firing position. Alternatively or additionally, a probability coefficient may be calculated for each leaf of an MLC, and may specify the likelihood that a leaf of a binary MLC is in an open configuration (or closed configuration) at a particular firing position (or sub-firing position). The firing probability coefficient may be derived from the calculated fluence map for that firing position (or sub-firing position). Probabilistic radiation delivery may help to reduce fluence residuals when a fluence value to be delivered falls between discrete (e.g., deliverable) fluence levels. In variations where the calculated fluence for a firing position falls between two discrete fluence levels, the fluence for delivery (i.e., segmented fluence level) may be rounded up or down to the next fluence level, depending on the firing probability coefficient. For example, when fluence values fall below a threshold fluence level (e.g., below the minimum deliverable fluence level at a firing position), a firing probability coefficient may represent the likelihood that the fluence for delivery is rounded up to the threshold fluence level (e.g., the likelihood that one or more MLC leaves is in the open configuration). The probability coefficient represents the probability of firing a beamlet at a particular fluence level (e.g., by opening and closing the MLC leaves according to their probability coefficients and/or by adjusting linac pulse emission parameters such as pulse width and/or pulse intensity) and may be calculated by dividing a fractional fluence increment (e.g., which may be the difference between the desired fluence and the deliverable fluence) by a preselected fluence level to be delivered at a sub-firing position (e.g., the minimum deliverable fluence). For example, a therapeutic radiation source such as a linac may be configured to emit radiation pulses at two intensity levels (e.g., 0.5 and 1) and to emit up to two pulses at each sub-firing position. Therefore, the linac may be able to deliver emit four non-zero fluence levels (0.5, 1, 1.5, and 2) per sub-firing position. Over a single firing position which groups several sub-firing positions (e.g. 4 sub-firing positions per firing position), the therapeutic source may deliver multiple non-zero fluence levels (e.g. 16 non-zero fluence levels), and change the MLC configuration at every sub-firing position. While the variations described herein have 4 sub-firing positions per firing position, in other variations, there may be any number of sub-firing positions per firing position, for example, 2, 3, 4, 5, 6, 7, 8, 10, 12, 20, more than 20, etc.

In a radiation therapy system where the linac is continuously rotated through the firing positions multiple times, the probability coefficient may determine the likelihood that an MLC leaf is in the open configuration at a particular firing position each time the MLC and linac is at that firing position. Alternatively or additionally, the probability coefficient may determine the likelihood that the linac will fire a beamlet at a particular fluence level each time the MLC and linac is at that firing position. For example, if the calculated fluence map indicates that a fluence value of 1.7 is to be emitted at a firing position and the linac is configured to emit fluence only at the fluence levels (0, 0.5, 1, 1.5, and 2), where the minimum deliverable fluence level is 0.5, the fluence level of 1.7 may be deconstructed into two fluence values: 1.5 (which is a deliverable fluence level) and 0.2 (which is an undeliverable fluence value). A firing probability coefficient value of 0.4 may be calculated by dividing 0.2 (the difference between the desired fluence value and the deliverable fluence level) by 0.5 (e.g., the minimum deliverable unit of fluence at a sub-firing position, or a preselected fluence level to be delivered at a sub-firing position), i.e., (1.7−1.5)/0.5=0.4. During delivery, a fluence level of 1.5 may be emitted by the linac every time the linac is located at (and/or passes through) the firing position, while the additional 0.5 fluence level is delivered according to the probability coefficient. That is, whenever the linac is located at the firing position, there is a 40% chance that a fluence level of 2 is emitted (i.e., 1.5 with the extra 0.5 fluence level), and a 60% chance that a fluence level of 1.5 is emitted (i.e., without the extra 0.5 fluence level). Alternatively or additionally, whenever the linac is located at the firing position, there is a 40% chance that an MLC leaf is in the open configuration at a particular sub-firing position so that a fluence level of 2 is emitted, and a 60% chance that the MLC leaf is in the closed configuration at a particular sub-firing position so that a fluence level of 1.5 is emitted. Over multiple passes as the linac is continuously rotated about the patient, the fluence delivered to the patient from that firing position may converge to 1.7. In some variations, a random numerical value between 0 and 1 may be selected from an unbiased uniform random distribution and compared against the firing probability coefficient to determine whether the extra 0.5 fluence level is to be delivered. In this example, if the random numerical value is less than or equal to 0.4, the extra 0.5 fluence level is emitted by the linac (i.e., linac emits a fluence level of 2) and/or an MLC leaf is in the open configuration, and if the numerical value is greater than 0.4, the extra 0.5 fluence level is not emitted by the linac and/or the MLC is in the closed configuration. Such probabilistic firing may allow the radiation therapy system to increase the accuracy and/or precision of delivery beyond the minimum deliverable dose quanta, and may not require carrying any state information associated with firing position. This approach may be advantageous, for example, when delivering dose to a moving target.

Figure 7A:
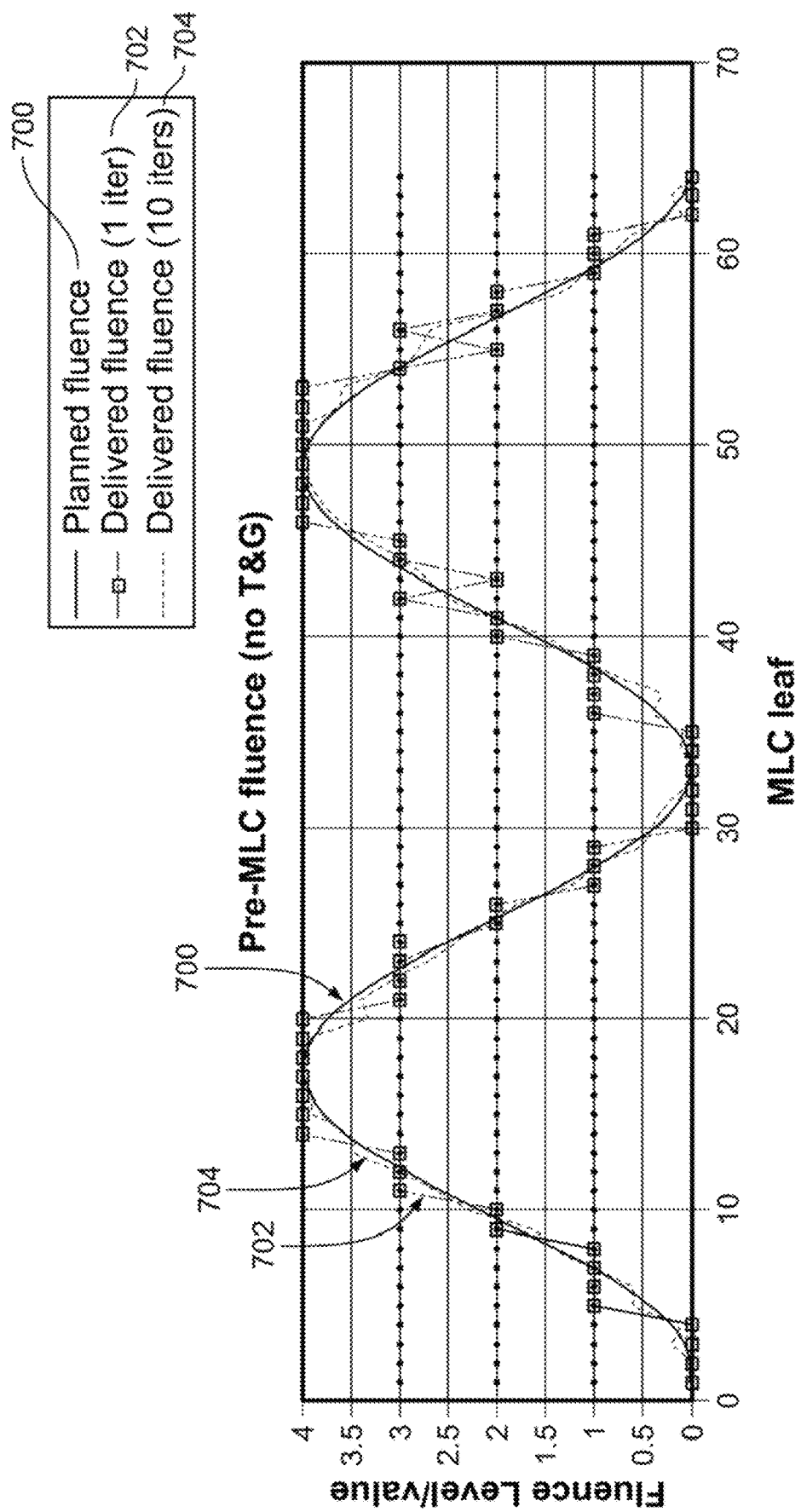
FIG. 7A depicts an exemplary plot of simulated emission $f_{delivery}$ of a fluence map that has been discretized into discrete fluence levels, comparing the planned fluence values, emitted fluence values after one iteration, and emitted fluence values after 10 iterations.

FIG. 7A depicts one example of a simulation resulting from emitting fluence based on a probability coefficient as described above. In this example, the therapeutic radiation source (e.g., linac) is continuously rotated about the patient, and the fluence emitted for each MLC leaf opening of a 64-leaf binary MLC is plotted. A first solid line (700) represents the planned fluence values to be emitted for each leaf based on a fluence map for a firing position, which may be calculated using any of the methods described herein. For example, these fluence values may be derived from a fluence map ($F_i$) calculated by multiplying an RFM for the corresponding firing angle with a partial image ($x_i$) acquired in real-time. When the fluence map is segmented into beamlets that are deliverable by the linac, the continuous fluence values may be discretized into deliverable fluence levels (e.g., 0, 0.5, 1, 1.5, 2, 2.5, 3, 3.5, 4) that may be emitted over multiple sub-firing positions corresponding to a firing position. In the example of FIG. 7A, the fluence values may be emitted over 4 sub-firing positions, where up to two fluence levels (0.5 and 1) may be emitted per sub-firing position. A second line (702) with square bullets represents the fluence levels that may be emitted for each leaf after the linac has revolved around the patient once (e.g., one rotation of the gantry, one iteration or pass). As can be seen in the plot, when fluence values fall between the fluence levels, for a single iteration, the emitted fluence is rounded up or down to a fluence level based on the calculated probability coefficient. In this example, the maximum planned fluence that may be delivered at a firing position (i.e., according to a fluence map calculated using any of the methods described herein) across all MLC leaves is 4, which may deconstruct to a maximum deliverable fluence level of 1 for each of the 4 sub-firing positions. For example, the planned fluence value as depicted in FIG. 7A for MLC leaf number 40 is about 1.6. Since the fluence level per sub-firing position is 1, the probability coefficient may be (1.6−1)/1=0.6. Based on a probability coefficient of 0.6, there is a 60% chance that the emitted fluence level for MLC leaf number 40 is 2 and an 40% chance that the emitted fluence level for MLC leaf number 40 is 1. For example, with a probability coefficient of 0.6, there may be a 60% chance that MLC leaf number 40 is open and a 40% change that MLC leaf number 40 is closed. Each MLC leaf may have a different probability coefficient calculated based on the fluence map, and may be calculated by the system controller. Referring back to line (702) in FIG. 7A, in this particular single iteration, the fluence level for MLC leaf number 40 is 2. However, over 10 iterations, as represented by a third dotted line (704), the average fluence emitted for MLC leaf number 40 converges closely to fluence value 1.6. That is, by emitting a fluence level of 2 for about 60% of the time and emitting a fluence level of 1 for about 40% of the time (e.g., MLC leaf number 40 in the open configuration for about 60% of the time and in the closed configuration for about 40% of the time), the average emitted fluence may eventually converge toward about 1.6. Probabilistically firing at certain discrete fluence levels over multiple passes or iterations may facilitate precise delivery of planned fluence values, which may help offset and/or reduce any fluence differences when the planned fluence is discretized into beamlet fluence levels as part of the segmentation process.

In some variations, segmenting the fluence map $f_{calc}$ may optionally comprise deconstructing $f_{calc}$ into a plurality of sub-fluence maps for each firing position that correspond to sub-firing positions located between firing positions, and segmenting each of the sub-fluence maps into radiation delivery instructions for each sub-firing position. For radiation therapy systems comprising a binary MLC, each sub-fluence map in addition may have a firing probability coefficient, and each leaf of the MLC may be configured to open or close based on the firing probability coefficient.

Figure 6B:
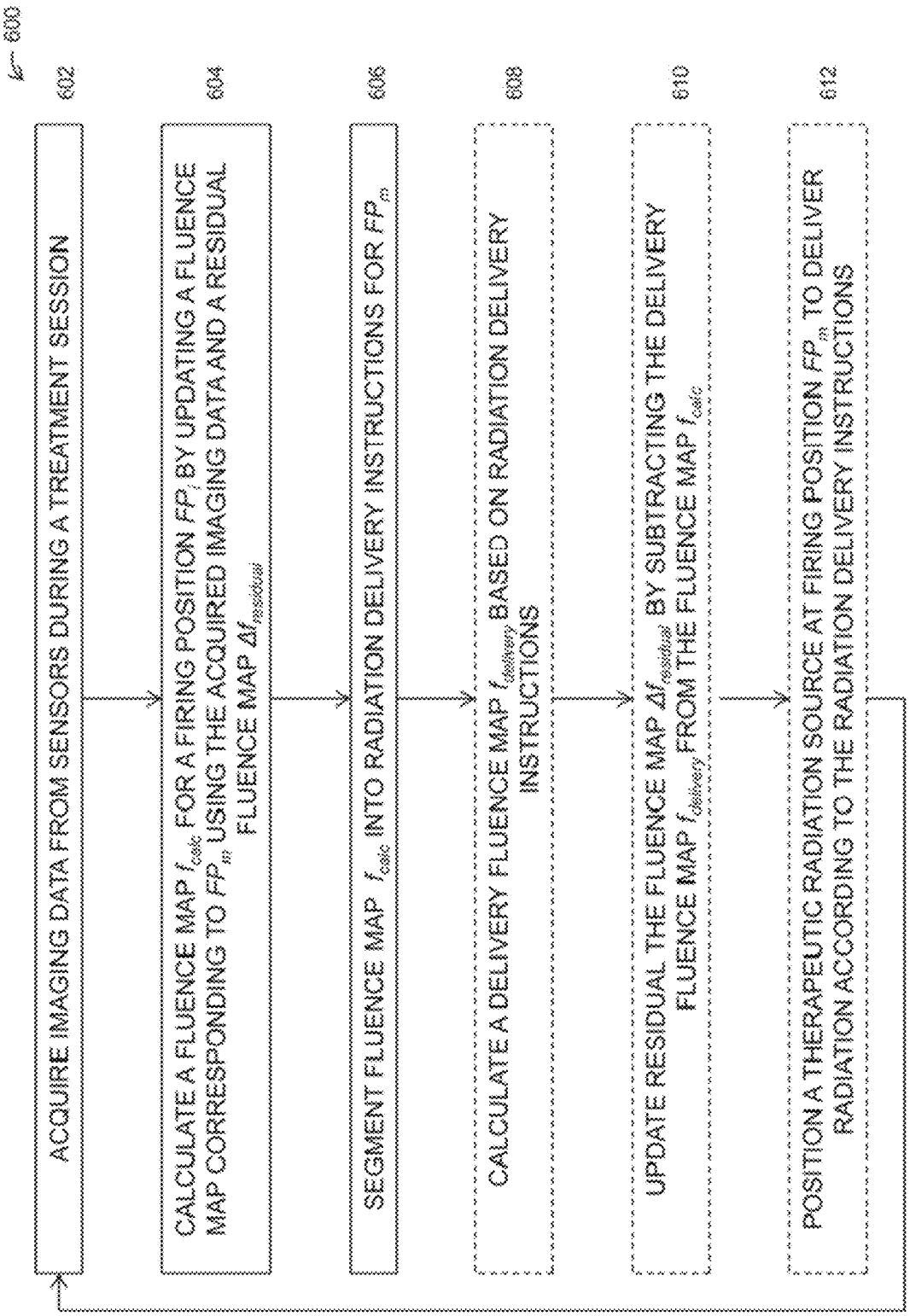
FIG. 6B depicts a flowchart representation of one variation of a method for real-time segmentation of a fluence map calculated during a treatment session.

One variation of a method for real-time segmentation of updated fluence maps and mitigation of segmentation errors is depicted in FIG. 6B. Method (600) may comprise acquiring (602) imaging data (e.g., from imaging sensors of any modality such as PET detectors, X-ray detectors, MR sensors, and the like that may be rotatable about a patient) during a treatment session, calculating (604) a fluence map $f_{calc}$ for a firing position $FP_m$ by updating a fluence map corresponding to $FP_m$ using imaging data and a residual fluence map $\Delta f_{residual}$, and segmenting (606) the fluence map $f_{calc}$ into a set of radiation delivery instructions for $FP_m$ (e.g., a segmented fluence map that designates the beamlets for one or more firing position or angle). In some variations, calculating (604) a fluence map $f_{calc}$ may comprise updating an existing fluence map from the treatment plan (i.e., fluence map F) that has been loaded onto the radiation therapy system or a fluence map that has been previously updated during earlier in the treatment session (i.e., fluence map $F_i$ or a previous $f_{calc}$). The fluence map $f_{calc}$ may be the fluence map for the entire treatment session (i.e., across all firing positions, all patient platform positions or beam stations, for the entire duration of the treatment session) and/or may be a fluence map for a subset of firing positions, beam stations, and/or treatment session time interval and/or may be a fluence map for the next one or more firing positions (e.g., $FP_m$, $FP_{m+1}$). Segmenting (606) may also comprise calculating one or more probability coefficients for each MLC leaf for each firing position and/or sub-firing position, as described above. Optionally, the radiation therapy system may then deliver radiation to the patient in accordance with the radiation delivery instructions. For example, method (600) may optionally comprise positioning (612) a therapeutic radiation source at the firing position $FP_m$ and/or adjusting MLC leaf configurations to deliver radiation according to the radiation delivery instructions. In some variations, after calculating the segmented fluence map, method (600) may further comprise updating the residual fluence map, which may be used for future fluence map updates. Method (600) may comprise calculating (608) a delivery fluence map $f_{delivery}$ based on the radiation delivery instructions and/or the segmented fluence map, updating (610) a residual fluence map $\Delta f_{residual}$ by subtracting the delivery fluence map $f_{delivery}$ from the fluence map $f_{calc}$. Delivery of radiation according to the radiation delivery instructions may occur before, during, and/or after the residual fluence map $\Delta f_{residual}$ is updated. In some variations, the radiation delivery instructions may include radiation delivery source instructions for multiple gantry rotations (e.g., one set of instructions for each gantry rotation at a patient platform position or beam station).

Figure 6C:
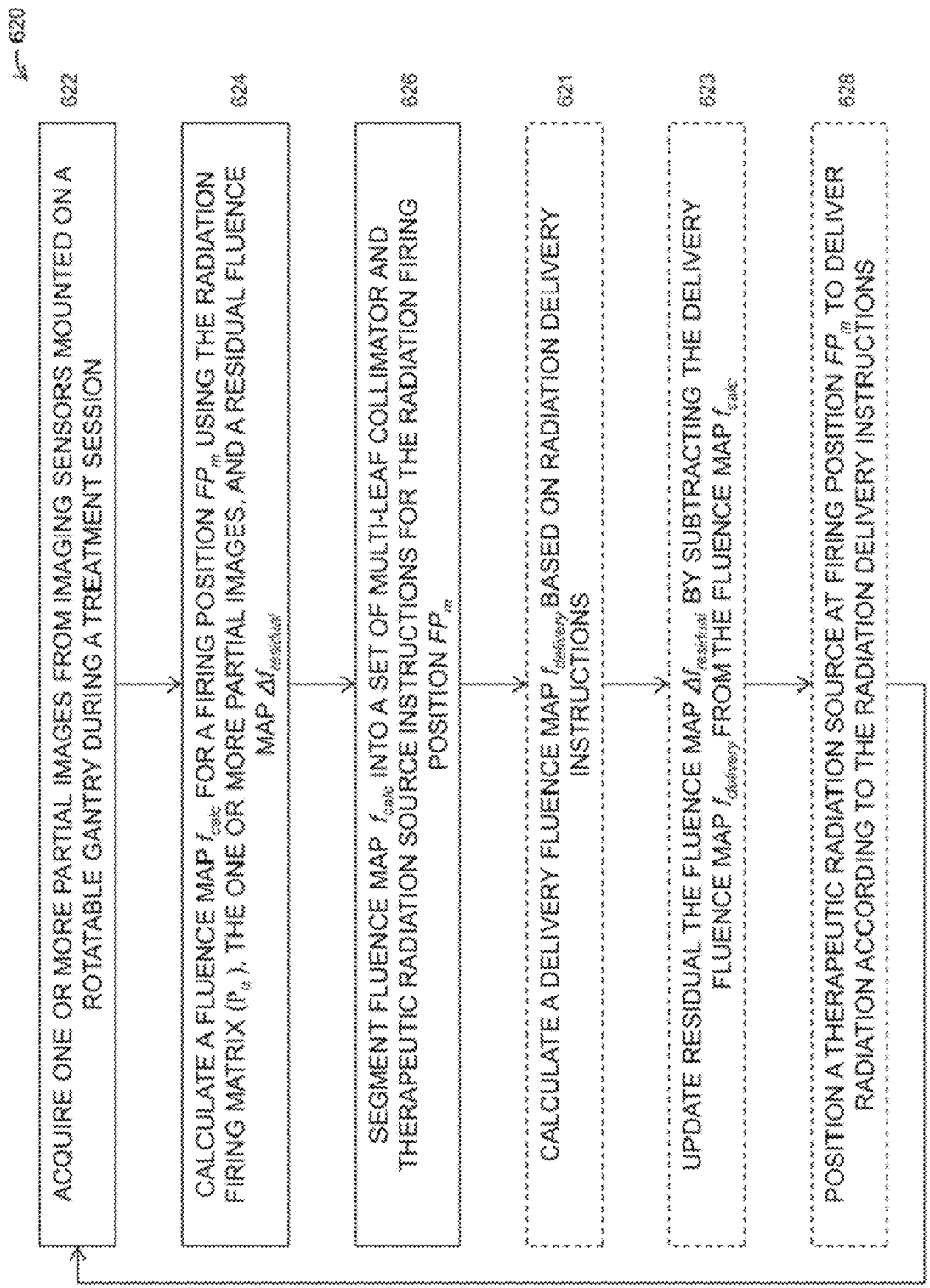
FIG. 6C depicts a flowchart representation of one variation of a method for real-time segmentation of a fluence map calculated during a treatment session.

In some variations, real-time fluence map segmentation and mitigation of segmentation errors may comprise calculating the fluence map using partial images (e.g., by multiplying the partial image with the treatment plan radiation firing matrix) and the residual fluence map $\Delta f_{residual}$. One example of a method (620) is depicted in FIG. 6C. Method (620) may comprise acquiring (622) one or more partial images (e.g., from imaging sensors of any modality such as PET detectors, X-ray detectors, MR sensors, and the like that may be rotatable about a patient) during a treatment session, calculating (624) a fluence map $f_{calc}$ for a firing position $FP_m$ by multiplying an RFM from the treatment plan corresponding to $FP_m$ (i.e., the radiation-firing matrix $P_\alpha$ for firing angle $\alpha$) with one or more partial images adding a residual fluence map $\Delta f_{residual}$, and then segmenting (626) the fluence map $f_{calc}$ into a set of MLC and therapeutic radiation source instructions for firing position $FP_m$ (and optionally, for each radiation firing position during the treatment session or for the next firing position $FP_{m+1}$). The fluence map $f_{calc}$ for firing position $FP_m$ may be calculated by multiplying the one or more partial images by a RFM from the treatment plan that corresponds to that firing position $FP_m$ (e.g., $P_\alpha$).

Alternatively or additionally, calculating (624) a fluence map $f_{calc}$ may comprise updating an existing fluence map from the treatment plan (i.e., fluence map F) or a fluence map that has been previously updated during earlier in the treatment session (i.e., fluence map F, or a previous fait). In some variations, the updated fluence map $f_{calc}$ may be the fluence map for the entire treatment session (i.e., across all firing positions, all patient platform positions or beam stations, for the entire duration of the treatment session) or may be a fluence map for a subset of firing positions, beam stations, and/or treatment session time interval and/or may be a fluence map for the next one or more firing positions (e.g., $FP_m$, $FP_{m+1}$). Segmenting the fluence map $f_{calc}$ may generate a set of MLC and therapeutic radiation source instructions for all firing positions at a particular (i.e., current) patient platform position or beam station (e.g., where the platform is stationary). In some variations where the gantry rotates multiple times at a beam station, the segmented fluence map of updated fluence map $f_{calc}$ may comprise one or more sets of discrete fluence levels and/or MLC and therapeutic radiation source instructions for one or more firing positions for each gantry rotation.

Figure 7B:
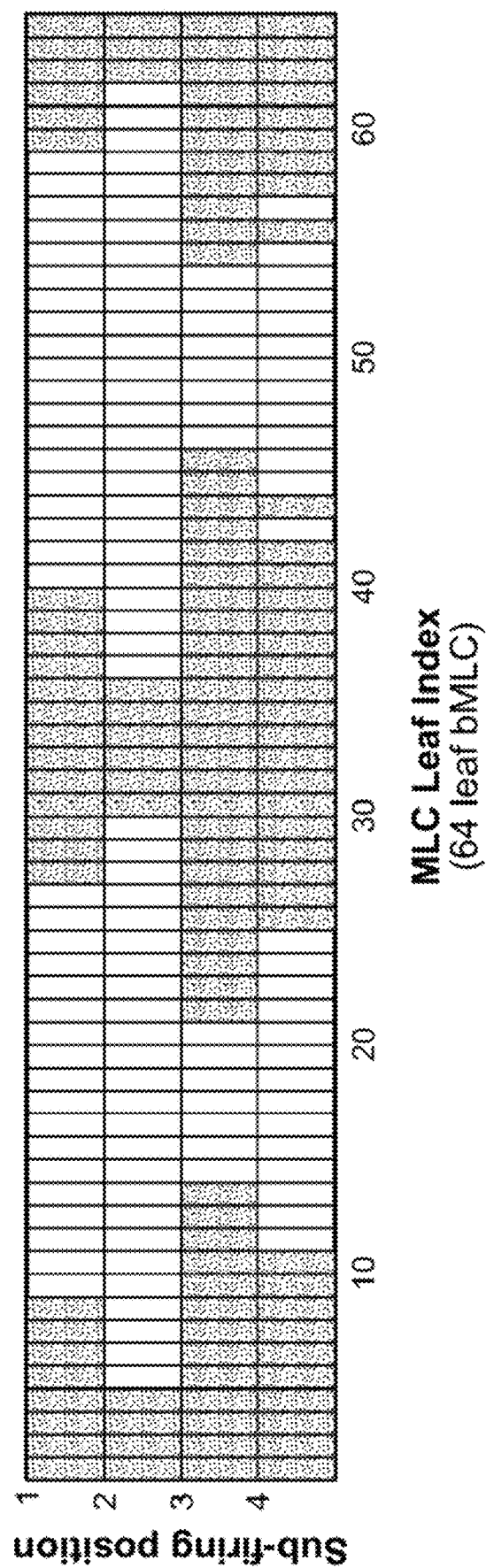
FIG. 7B depicts a graphical representation of multi-leaf collimator leaf positions over four sub-firing positions of a firing position.

Segmentation of a fluence map (e.g., the result of steps (606) and (626) of the methods of FIGS. 6B and 6C respectively) may generate a set of MLC instructions and therapeutic radiation source instructions. Examples of instructions may include MLC leaf opening commands or data on a per-firing position basis and linac pulse parameters on a per-firing station basis. FIG. 7A is a graphical representation of one example of the linac pulse parameters (e.g., fluence values discretized into fluence levels that are deliverable over one or more gantry rotations) and FIG. 7B is a graphical representation of one example of the each of leaf positions of a binary MLC over 4 sub-firing firing positions corresponding to a single firing position in a single gantry rotation. Each cell or block in the plot represents a particular leaf at a particular sub-firing position, and the color represents the position of the leaf, where a dark shade indicates that the leaf is in a closed configuration and a light shade indicates that the leaf is in an open configuration. The sum of the fluence emitted through the binary MLC apertures of 4 sub-firing positions may approximate or equal to the calculated fluence for that firing position. The profile of the binary MLC opening may correspond with the linac pulse parameters of FIG. 7A. At each pass, the binary MLC opening shape (i.e., the individual MLC leaf positions) may change according to the calculated fluence map. A variety of MLC leaf configurations for the 4 sub-firing positions may be possible while still cumulatively delivering the calculated fluence for that firing position. For example, the rows be reordered (i.e., changing the order of the MLC leaf configurations), and/or the columns may be reordered (i.e., slightly adjusting the angle from which fluence is emitted), while the sum of the fluence delivered over the 4 sub-firing positions still approximate or equal to the calculated fluence for that firing position.

Optionally, the radiation therapy system may then deliver radiation to the patient in accordance with the radiation delivery instructions. For example, method (620) may optionally comprise positioning (628) a therapeutic radiation source at the firing position $FP_m$ and/or adjusting MLC leaf configurations to deliver radiation according to the radiation delivery instructions. In some variations, after calculating the segmented fluence map, method (620) may further comprise updating the residual fluence map, which may be used for future fluence map updates. Method (620) may comprise calculating (621) a delivery fluence map $f_{delivery}$ based on the radiation delivery instructions and/or the segmented fluence map, updating (623) a residual fluence map $\Delta f_{residual}$ by subtracting the delivery fluence map $f_{delivery}$ from the fluence map $f_{calc}$. Delivery of radiation according to the radiation delivery instructions may occur before, during, and/or after the residual fluence map $\Delta f_{residual}$ is updated. In some variations, the radiation delivery instructions may include radiation delivery source instructions for multiple gantry rotations (e.g., one set of instructions for each gantry rotation at a patient platform position or beam station). Method (620) may be repeated for multiple gantry rotations at each beam station.

In some variations, real-time fluence map segmentation and mitigation of segmentation errors comprises calculating MLC and/or therapeutic radiation source instructions or commands for each firing position and/or sub-firing position. The MLC may step through a series of aperture shapes at each of the sub-firing positions while the therapeutic radiation source travels through the angular region corresponding to a firing position so that the sum of the fluence delivered through each of the sub-firing position aperture shapes is equal to (or approximates) the fluence to be delivered at the corresponding firing position. FIG. 7B depicts an example of a series of MLC aperture shapes of the 4 sub-firing positions of a firing position. Alternatively or additionally, segmentation and mitigation of segmentation errors may comprise deconstructing a fluence map into sub-fluence maps to be delivered at firing positions and/or locations between the firing positions (i.e., sub-firing positions). For example, a fluence map for an entire treatment session may be deconstructed into a series of sub-fluence maps to be delivered at a firing position and/or at a series of sub-firing positions located in-between firing positions. Any of the segmentation methods described herein may be used to calculate sub-fluence maps for each of the sub-firing positions. In some radiation therapy systems comprising a continuously rotating gantry, there may be 50 firing positions and 4 sub-firing positions for each firing position. For a particular firing position, the MLC may transition through various aperture shapes at each of the sub-firing positions preceding the firing position such that once the therapeutic radiation source delivers radiation at the firing position, the sub-fluence map for that particular firing position has been delivered. Segmentation methods may generate radiation delivery instructions for each sub-firing position between two firing positions.

Figure 6D:
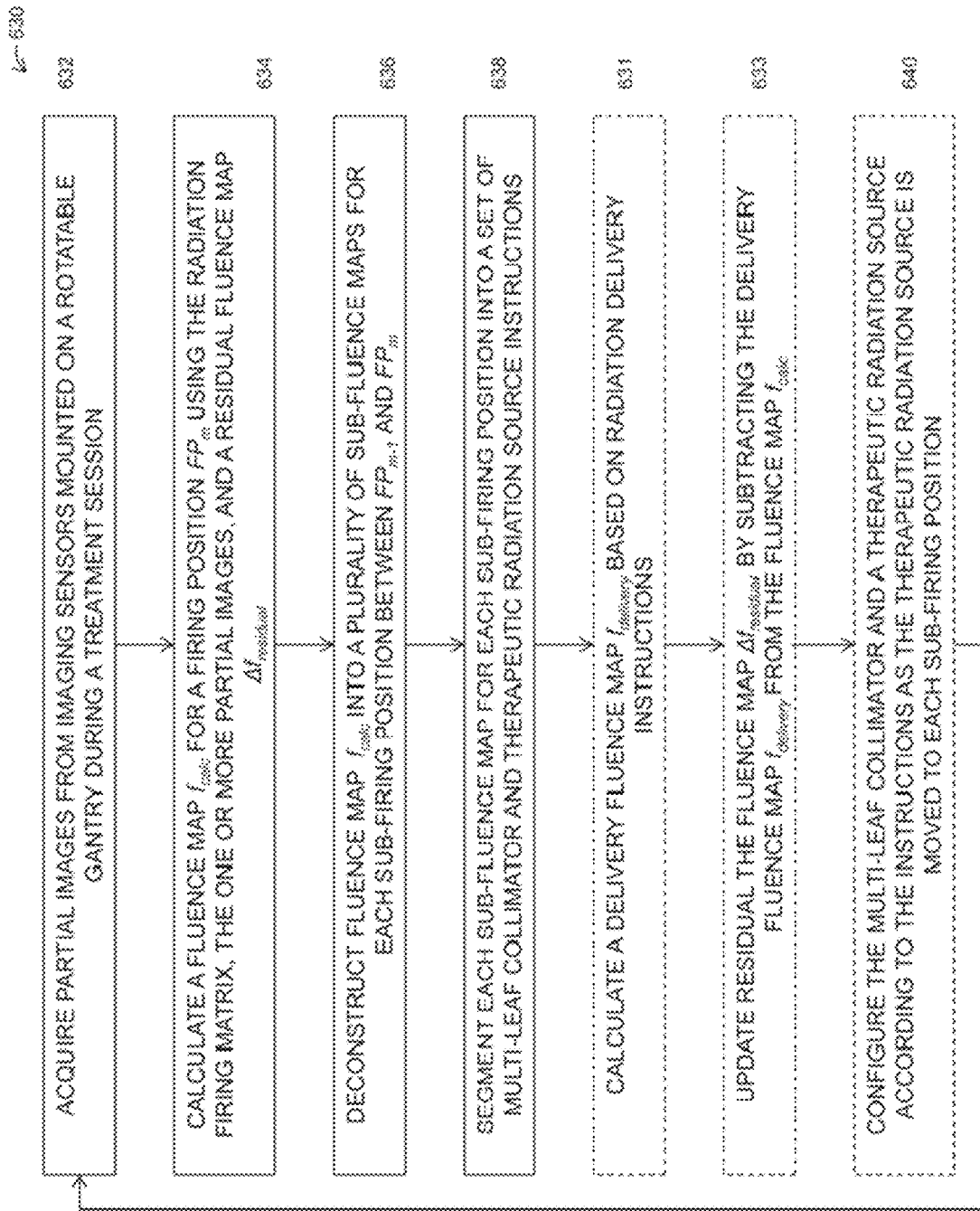
FIG. 6D depicts a flowchart representation of one variation of a method for real-time segmentation of a fluence map into sub-fluence maps during a treatment session.

FIG. 6D depicts one variation of a method (630) for segmenting an updated fluence map into a set of radiation delivery instructions for sub-firing positions. The method (630) may comprise acquiring (632) imaging data from imaging sensors mounted on a rotatable gantry during a treatment session, calculating (634) a fluence map $f_{calc}$ for a firing position $FP_m$ using a RFM calculated during treatment planning, the acquired imaging data, and a residual fluence map $\Delta f_{residual}$, deconstructing (636) the fluence map $f_{calc}$ into a plurality of sub-fluence maps for each radiation sub-firing position between $FP_{m-1}$ and $FP_m$ (e.g., $FP_{m-0.5}$, $FP_{m-0.25}$, etc.), and segmenting (638) each sub-fluence map for each sub-firing position and/or firing position into a set of MLC and therapeutic radiation source instruction. Segmenting (638) may also comprise calculating one or more probability coefficients for each MLC leaf for each firing position and/or sub-firing position, as described above. The imaging data may be acquired from imaging sensors of any modality such as PET detectors, X-ray detectors, MR sensors, and the like. Optionally, method (630) may comprise configuring (640) the MLC and therapeutic radiation source during the treatment session according to the instructions at each sub-firing and/or firing position. In some variations, the set of MLC and therapeutic radiation source instructions may include MLC and therapeutic radiation source instructions for multiple gantry rotations (e.g., one set of instructions for each gantry rotation at a beam station). Method (630) may be repeated for each patient platform position or beam station, and/or may be repeated for multiple gantry rotations at each beam station. In some variations, after calculating the segmented fluence map, method (630) may further comprise updating the residual fluence map, which may be used for future fluence map updates. Method (630) may comprise calculating (631) a delivery fluence map $f_{delivery}$ based on the radiation delivery instructions and/or the segmented fluence map, updating (633) a residual fluence map $\Delta f_{residual}$ by subtracting the delivery fluence map $f_{delivery}$ from the fluence map $f_{calc}$.

Fluence maps that are calculated or updated in real-time may be segmented into MLC and therapeutic radiation source instructions that are to be executed over multiple gantry rotations while the patient is held stationary at a patient platform location (i.e., beam station). In some variations, the updated fluence map $f_{calc}$ for a particular firing position may be delivered in one gantry rotation (e.g., as described above using sub-firing positions), or may be delivered in two or more gantry rotations. For example, $f_{calc}$ may be deconstructed into a set of fluence maps that may be delivered at the particular firing position over multiple gantry rotations. That is, the calculated fluence map for a particular beam station may be deconstructed or split into one or more fluence map "installments" that are deliverable over two or more gantry rotations. Applying therapeutic radiation from the same firing position multiple times may help to mitigate segmentation errors by calculating the amount and distribution of the fluence segmentation error or fluence residual, and delivering the fluence residual at a subsequent gantry rotation. In one method, a segmentation error may be calculated by calculating the fluence difference or residual $\Delta f_{residual}$ between the updated or calculated fluence map $f_{calc}$ and the delivery fluence map $f_{delivery}$ (i.e., radiation delivery instructions), and delivering the fluence residual $\Delta f_{residual}$ at a subsequent gantry rotation over the firing position (e.g., in a system with a continuously rotating gantry). Alternatively, in a system where the duration of time that a therapeutic radiation source is positioned at a firing position can be adjusted (i.e., not in a continuously rotating gantry), the MLC and therapeutic radiation source may be adjusted to deliver multiple fluence levels as designated by multiple segmented fluence maps.

Segmentation errors may also arise from leaf fluence errors. Leaf fluence errors represent the difference between the fluence map deliverable through a MLC aperture shape (e.g., which can be estimated using leaf models applied to a segmented fluence map) and the segmented fluence map deliverable through a hypothetical "ideal" MLC that does not exhibit any of the leaf artifacts described below. For example, leaf models may represent leaf artifacts such as tongue-and-groove notches at the leaf edges that cause radiation beam shadows, which may alter the fluence at the end of the leaves. Other sources or causes of radiation beam shadows may include leaf mounts (e.g., screws, shafts, etc.). Leaf fluence errors that result in fluence residuals may be delivered, in subsequent gantry rotations, as described above. The above methods may be augmented to model these additional factors in $f_{delivery}$ calculations, and as a result the residual fluence $\Delta f_{residual}$ may include these additional errors.

As described previously, a segmented fluence map may comprise a set of radiation therapy system or machine instructions, including but not limited to, MLC configuration at each firing position (e.g., for each gantry rotation and for each beam station), radiation pulse width, and number of pulses at each firing position. In some variations where the radiation therapy system comprises a binary MLC (bMLC) where a leaf can either be opened or closed, one way to mitigate segmentation errors is to deliver the residual fluence map $\Delta f_{residual}$ by probabilistic leaf opening, where a firing probability coefficient (i.e., probability coefficient) of a leaf moving to the open configuration is derived from the residual fluence $\Delta f_{residual}$. In some variations, a leaf may be open during delivery, but the beamlet fluence level emitted may be determined by a firing probability coefficient, as described above. Segmentation of an updated fluence map $f_{calc}$ for bMLCs may comprise deconstructing the fluence map $f_{calc}$ into a discrete fluence levels, where the minimum fluence level may be the minimum dose unit that can be delivered. Probabilistic segmentation (i.e., segmenting a fluence map of continuous fluence values into a fluence map of discrete fluence levels, where each fluence level may have a corresponding firing probability coefficient) may be used to deliver fluence residuals that are less than what the therapeutic radiation source can deliver. In one variation of probabilistic segmentation, a probability of a leaf opening may be the fluence residual or sub-level fluence.

When a firing position is visited multiple times by the radiation source (e.g., in the case of a continuously rotating gantry) and radiation applied according to a firing probability coefficient calculated based on the residual fluence levels, multiple random decisions may converge to the desired fluence, where any remaining residual noise may be random noise.

One or more of the methods above may be combined and used for real-time segmentation of real-time calculated fluence maps in biologically-guided radiotherapy (BGRT), where the radiation therapy system updates a fluence map using PET emission data. The cumulative fluence map for the entire treatment session or fraction may be calculated at various timepoints throughout the session or fraction, and/or per-firing position or per-control point fluence maps may be updated continuously, just before the therapeutic radiation source is moved to that firing position or control point. In addition to updating fluence maps based on PET emission data, fluence maps may also be calculated to include residual fluence that is a combination of segmentation errors (e.g., any of the segmentation errors described above) and/or undeliverable fluence quantities from a previous firing position or control point (e.g., any negative fluence values and/or undelivered fluence due to machine aberrations, etc.). The method may further comprise discretizing the updated fluence map into a map of discrete fluence levels (e.g., segmented fluence levels), and segmenting the map of discrete fluence levels into a set of radiation delivery instructions or system/machine instructions and parameters (e.g., firing location/angle, bMLC configuration, pulse timing, etc.). In some variations, a method for segmentation of a fluence map may optionally comprise calculating a firing probability coefficient for one or more leaves of a bMLC where the fluence value(s) to be delivered by the one or more leaves is in between two segmented fluence levels (or below a threshold fluence level, such as the minimum discrete fluence level). In addition to bMLC aperture shapes or leaf configurations, a set of radiation delivery instructions or system/machine instructions resulting from fluence map segmentation may comprise radiation beam pulse width modulations and the number of pulses fired each time the radiation source is located at (or passes through) a firing position. In particular, for systems comprising a continuously rotating gantry where the time that the therapeutic radiation source is located at a firing position is in the range of a few milliseconds, the therapeutic radiation source or beam generation system may only be able to generate a small number of pulses (e.g., less than 5 pulses), thereby limiting the amount of dose modulation per MLC aperture shape or leaf configuration. Changing the pulse width may help increase the amount of dose modulation at each firing position. Alternatively or additionally, radiation beam pulses may also be applied between firing positions at sub-firing positions (i.e., while the therapeutic radiation is moving from one firing position to the next). Firing radiation beam pulses at sub-firing positions may approximate the effect of increasing the number of beam pulses at the subsequent firing position.

Treatment Plan Normalization

Optionally, a treatment plan may be normalized with patient image data acquired just prior to a treatment session, during a pre-scan. In this case, the imaging system may acquire a new image $X_{prescan}$, intended to to be a more recent version of an image X used in treatment planning. This may help deliver therapeutic radiation to the patient that corresponds with the desired dose, despite any changes in patient data from when the treatment plan images were acquired and when the treatment begins. Normalization of the treatment plan or radiation-firing matrix using a prescan image $X_{prescan}$ may be done so that even if there are any geometric or other differences in the target(s) or other patient organs, or their relative positions, these differences may be factored into the treatment plan and/or RFM. This may help facilitate the delivery of radiation dose as planned (e.g., help to deliver radiation dose that is as close as possible to the desired result). Normalization may facilitate the calculation of an updated radiation firing matrix $P_{prescan}$ so that the dose predicted at treatment planning time is approximately equal the dose recalculated using the prescan image $X_{prescan}$, i.e.

$$D \approx D_{prescan}$$

$$A \cdot P \cdot X \approx A \cdot P_{prescan} \cdot X_{prescan}$$

In this method, the controller of the radiation therapy system may be configured to normalize for any differences in the target regions and/or patient parameters between the simulation and imaging system of the radiation treatment system, by recalculating $P_{prescan}$, given a known dose calculation matrix A, treatment plan RFM P, treatment plan full image X, and a pre-scan image $X_{prescan}$.

One method to calculate $P_{prescan}$ is to assume $P_{prescan} = k \cdot P$, where k is a scalar, and iteratively find k that minimizes $|A \cdot P \cdot X - A \cdot P_{prescan} \cdot X_{prescan}| = |A \cdot (PX - kPX)| = |AP \cdot (X - kX)|$.

By using the updated $P_{prescan}$ during treatment delivery, any differences between the image in scale or shape may be corrected without re-creating the treatment plan.

In some variations, $P_{prescan}$ can be calculated by assuming that $X_{prescan}$ may be approximated by a rigid deformation w of X, that is $X_{prescan} \approx R_w \cdot X$, where $R_w$ is a linear transformation matrix corresponding to a rigid deformation w, and iteratively find the rigid deformation w that minimizes $|A \cdot P \cdot X - A \cdot P \cdot R_w \cdot X_{prescan}| = |AP \cdot (X - R_w \cdot X)|$. This minimization problem may be solved using standard convex optimization techniques, such as gradient descent. Final step may include setting $P_{prescan} = P \cdot R_w$.

In some variations, $P_{prescan}$ may be calculated by assuming that $X_{prescan}$ may be approximated by a general linear function R of X, that is $X_{prescan} \approx R \cdot X$, where R is a linear transformation matrix, and iteratively find R that minimizes $|A \cdot P \cdot X - A \cdot P \cdot R \cdot X_{prescan}| = |AP \cdot (X - R \cdot X)|$. This minimization problem may be solved using standard convex optimization techniques, such as gradient descent. Final step may include setting $P_{prescan} = P \cdot R$.

In some variations, if the difference between the dose $D_{prescan}$ calculated based on $X_{prescan}$ and the planned dose D (i.e., $D_{prescan} - D$) exceeds a pre-selected threshold (e.g., as selected or determined by a clinician), the treatment session may be paused or halted. The treatment plan may be re-evaluated and in some cases, re-calculated to reflect changes in the patient.

In some variations, the desired radiation dose for a RFZ or target region may be calculated from the point-of-view (POV) of the target region (e.g., an irradiation target region). Calculating the desired dose from the POV of the target region may be helpful for a moving target. Usually, radiotherapy tends to plan and deliver radiation in the patient reference frame. In this frame if there is target motion, the target moves inside the patient. In the POV dose space, the target is fixed, and the patient is moving. In radiotherapy, POV target dose may be clinically relevant for meeting the dose prescription to achieve successful treatment of the target. The dose in the patient reference frame may be helpful for defining organs-at-risk (OAR) constraints.

Treatment Plan Evaluation and QA

A treatment plan and corresponding radiation-firing matrix may be evaluated prior to a treatment session to confirm that radiation delivered based on the RFM and partial images acquired during the treatment session would provide the prescribed dose of radiation (or within an approved tolerance) to all the RFZ and/or reduce exposure of any OARs. Evaluating the quality of a treatment plan and RFM may comprise loading the treatment plan (which may comprise a planned fluence map and/or planned dose map) and RFM to a radiation therapy system (e.g., a controller of the radiation therapy system), providing partial image data to the radiation therapy system, calculating a radiation fluence for delivery by multiplying the RFM and the partial image data, emitting radiation according to the calculated radiation delivery fluence, measuring the emitted radiation, calculating a fluence map (and/or dose map) based on the measured radiation, and comparing the calculated fluence map with the planned fluence map (and/or planned dose map). If the difference between the calculated fluence (and/or dose) map and the planned fluence (and/or dose) map exceeds a pre-specified difference threshold, the treatment plan and the RFM may be adjusted (e.g., transmitted back to a treatment planning system for re-planning). Providing a set of positron emission activity data to a radiation therapy system instead of using a PET-avid phantom (i.e., a phantom with one or more positron-emitting regions) may facilitate, and/or simplify, and/or expedite treatment plan evaluation. For example, "replaying" positron emission activity from a PET imaging session during treatment plan evaluation may allow for treatment plan and/or RFM quality to be evaluated using a non-PET-avid phantom and/or MV X-ray detector measurements. This may also help reduce personnel exposure to radioactivity and also help reduce the amount of time on the treatment system spent for quality assurance (QA). For example, a phantom-less QA procedure may reduce the time spent on repeated entrances and exits to the radiation bunker and/or positioning of a phantom on a treatment system patient platform.

The partial image data provided to a therapy system may comprise one or more positron emission line of responses (LOR), MRI sub-samplings in k-space, or CT 2-D projection X-ray images, as described previously. In the context of positron emission-guided radiation therapy, a set of positron emission activity data may comprise PET data (e.g., data about the positron emission events themselves, a set of LORs, and/or digitized and/or filtered PET detector output signals) acquired during a diagnostic PET imaging session. For example, diagnostic PET images used for treatment planning may also be used to evaluate and verify the treatment plan and/or RFM quality. In some variations, the full set of positron emission activity or LOR data from a diagnostic PET imaging session may be used to evaluate treatment plan and/or RFM quality, or a sub-set of the positron emission activity or LOR data may be used (e.g., the portion of the positron emission activity data corresponding to a RFZ, OAR, and/or corresponding to the field-of-view of treatment system PET detectors). In still other variations, simulated or synthetic positron emission activity data or LORs may be used to evaluate the quality of the treatment plan and/or RFM. Simulated or synthetic LORs may be generated based on a diagnostic PET image and/or the geometry of the PET imaging system that acquired the diagnostic PET image and/or PET detectors on the radiotherapy system. Simulated or synthetic LORs may be generated by the treatment planning system or the radiotherapy system. Positron emission activity data may comprise PET detector signals (e.g., voltage output over time, digitized and/or filtered PET detector data) that arise from the detection of positron emission events in a patient, and/or may be LOR data extracted from PET detector signals. Positron emission activity or LOR data may include, but is not limited to, relative timing between the detection of coincident photons, PET and/or detector noise (e.g., to reflect an expected or likely SNR or noise profile during a treatment session) including noise from radiation source(s), detector dark current, PET detector afterglow, artifacts due to patient movement (e.g., platform movement and/or patient fidgeting) and/or non-correlated or "random" events such as patient movement or shifts, and the like.

Figure 2C:
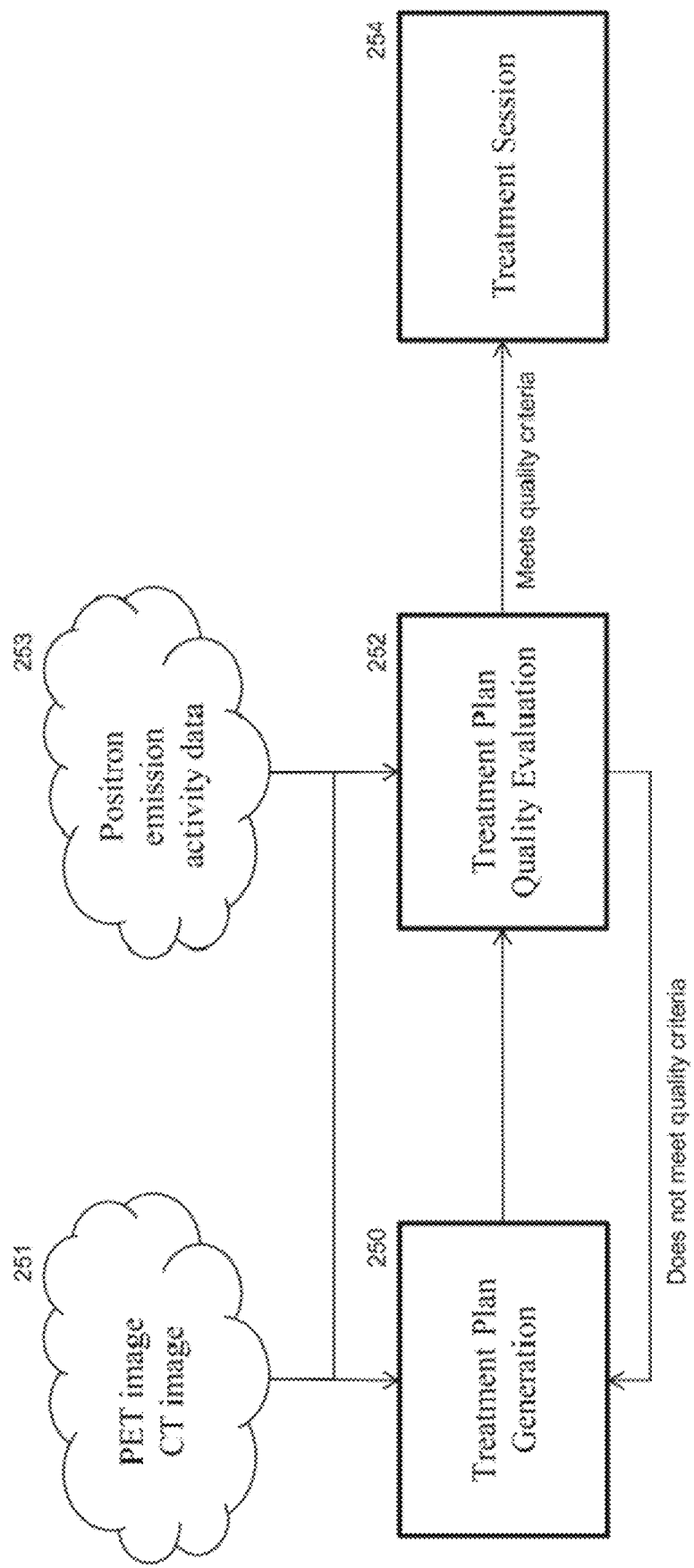
FIG. 2C depicts one variation of a method for treatment plan generation and verification.

FIG. 2C depicts one variation of a workflow that comprises evaluating the quality of a treatment plan and/or RFM before a treatment session. A method may comprise generating (250) a treatment plan and RFM, evaluating (252) the quality of the treatment plan and/or RFM, and then proceeding to the treatment session (254) if the treatment plan and/or RFM meet certain specified quality criteria. Treatment plan and RFM calculation (250) may use PET image and/or CT image data (251), and/or any of the parameters (202-204, 206) depicted in FIG. 2A. The generated treatment plan may comprise a RFM P, a planned dose map $D_0$, and a planned fluence map $F_0$. The treatment plan and associated parameters may be transmitted to a radiation therapy system for quality evaluation (252). PET image and/or CT image (251) data may be transmitted to the radiation therapy system and/or positron emission activity data may be generated based on filtering (e.g., spatial filtering) a set of PET image or LOR data acquired during an imaging session, or synthesizing a set of LORs. The positron emission activity data may comprise, for example, a set of digitized and/or filtered PET detector outputs that mimic or simulate the signals from the PET detectors during a treatment session for that patient. Positron emission activity data may include LORs from the RFZ (e.g., PTV, tumor regions), and may optionally include background LORs (to simulate non-specific PET tracer uptake), OAR LORs, LORs resulting from various noise sources and/or non-specific tracer uptake, and the like. Positron emission activity (i.e., LOR) data and/or PET image data may be transmitted to the radiation therapy system from a PET imaging system and/or a treatment planning system. The radiation therapy system may then generate and emit radiation in response to the positron emission activity (i.e., moving or rotating the gantry, activating the linac, adjusting the position of the leaves of a dynamic multi-leaf collimator, etc.). If the emitted radiation provides the dose and/or fluence as specified by the treatment plan, the treatment plan is determined to be of sufficiently acceptable quality to be used in a patient treatment session (254). Otherwise, the treatment plan and/or RFM P are adjusted by the treatment planning system and then re-evaluated on the radiation therapy system. One or more radiation measurement devices may acquire radiation emission data, and the controller may calculate a fluence and/or dose map based on the acquired emission data. Examples of measurement devices may include radiographic film, scintillators, single or arrays of ion chambers and/or diodes, scintillator-camera based EPIDs, liquid-filled ion chamber EPIDs, dose chamber, and the like. Alternatively or additionally, the emitted radiation may be measured using a phantom placed within the patient treatment region, the phantom having any desired shape, weight or density and any number of the measurement devices above. In some variations, the phantom may not be PET-avid, and may, for example, comprise an array of detectors, such as ARC-CHECK® and MAPCHECK® (by Sun Nuclear Corporation), MATRIXX by IBA Dosimetry, PTW Seven29, and/or radiographic films, and may be located within a patient treatment area (e.g., on a patient platform and/or within a bore of a circular gantry) and/or disposed in the beam path of the radiation source (e.g., downstream from the beam collimation system, over the MLC, etc.). In other variations, the phantom may be PET-avid.

Figure 2D:
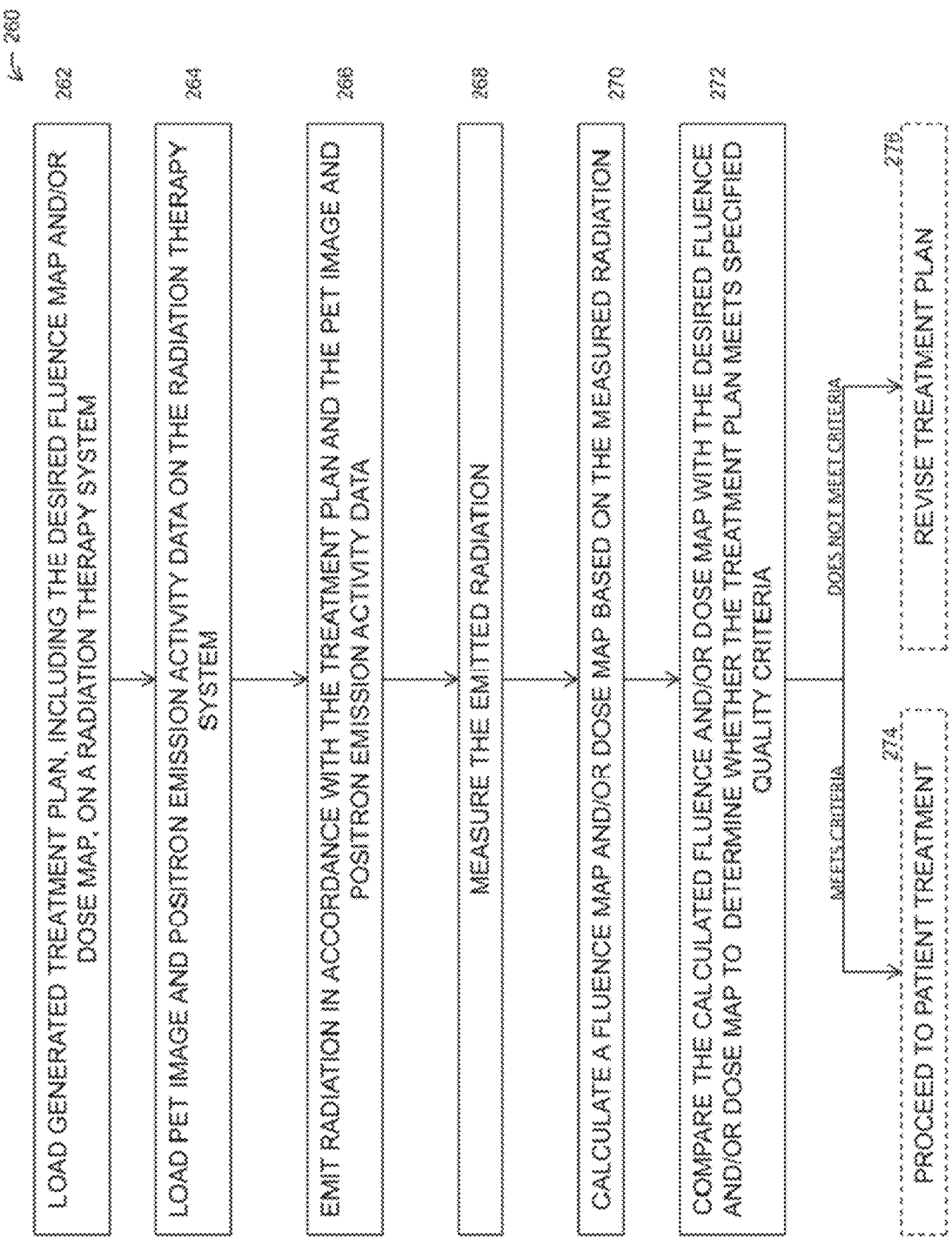
FIG. 2D depicts one variation of a method for treatment plan evaluation and quality assurance.

FIG. 2D depicts one variation of a method for evaluating the quality of a treatment plan and/or RFM. Method (260) comprises loading (262) a treatment plan on a radiation therapy system controller and loading (264) PET image and/or positron emission activity data on the controller. As described above, the treatment plan may comprise a RFM, prescribed or planned dose map and/or fluence map. Positron emission activity data and/or PET image data may comprise simulated or synthetic LORs and/or PET detector signals recorded during PET imaging session. Positron emission activity (i.e., LOR) data and/or PET image data may be spatially limited to ROIs, such as RFZ and/or OARs. The method (260) may further comprise emitting (266) radiation in accordance with the treatment plan and the positron emission activity data and/or PET image data. The radiation emitted by the system may be determined using any of the methods described herein. For example, a radiation therapy system may emit radiation by multiplying partial PET data from the loaded data with the RFM to obtain a calculated fluence map, segmenting the fluence map into hardware instructions and parameters (e.g., firing location/angle, MLC configuration, pulse timing, etc., using any of the methods described previously), and then activating the therapeutic radiation source (e.g., linac) to apply radiation according to the segmented fluence map. The method (260) may comprise measuring (268) the emitted radiation. Measuring the emitted radiation may comprise measuring the radiation (energy) fluence (energy per unit area, e.g., $J/cm^2$) and/or radiation dose (energy per unit mass, e.g. J/kg) over the duration of the session (e.g., continuously or at pre-determined time points or control points). Radiation emission data may be acquired using an MV detector and/or combination of signals from the dose monitor chamber of the radiation therapy system and MLC position sensors, and/or radiographic film or sensor arrays (e.g., diode, ion chamber or scintillation 1-D or 2-D arrays), diamond detectors, and/or 3-D dosimeters, such as polymer gel dosimeter, etc. located within the radiation beam path (e.g., phantom placed in the patient treatment area and/or attached to the emission opening of the therapeutic radiation source and/or dynamic MLC). Radiation fluence may be calculated, for example, by determining MLC configuration (e.g., leaf position) using the MVD data in combination with the firing position and number of radiation pulses fired at the particular firing position. For example, the position of each leaf in an MLC can be determined from MVD imaging data. The number of radiation pulses fired may be determined based on MVD data and/or a dose monitor chamber of the linac. In variations where a phantom is used, radiation dose may be measured using an ion chamber and/or may be calculated based on the geometry, density, attenuation coefficient, and/or mass of the phantom, in combination with the fluence measurements. The system controller may calculate (270) the delivered radiation fluence map and/or dose map and then compare (272) the calculated fluence and/or dose map with the desired fluence and/or dose map specified by the treatment plan. The emitted radiation dose or fluence map(s) may be calculated using machine parameter data, for example, radiation pulse data (e.g., pulse width, duration, magnitude, frequency, etc.), dynamic MLC configuration (e.g., leaf positions at each firing angle and patient platform position), gantry position (e.g., speed, relative positioning to the patient treatment region and/or patient platform), and the like. Based on the comparison of the emitted radiation dose and/or fluence map with the planned dose and/or fluence map, the controller may determine whether the treatment plan meets specified quality criteria. Optionally, a clinician may provide input to the controller as to whether the treatment plan or RFM meets specified quality criteria. Quality criteria may include consistency of radiation delivery over time according to the plan dose or fluence map, and/or precision of radiation delivery to RFZ, and/or avoidance of OARs. For example, the controller may calculate a Gamma metric, which is a combined score representing a distance-to-agreement (DTA) value of the isodoses and the absolute dose differences between the measured and planned dose and/or fluence map. A clinician may specify that in order for a plan or RFM to be of sufficient quality for treatment, the radiation delivered based on the plan must deliver dose within a specified tolerance, to a region within a specified DTA value, for a specified proportion of measurement or time points during the session. In some variations, a treatment plan of sufficient quality for treatment may deliver dose such that a specified percent of measurement points meet a threshold Gamma level for a specified level of DTA and absolute point dose differences. For example, a clinician may specify that passing criteria for a treatment plan is that radiation is delivered within about 3 mm DTA of one or more RFZs, with less than about 3% deviation from the dose specified for each RFZ, for at least 95% of the time points or measurement points. Optionally, the method (260) may comprise proceeding to patient treatment or revising the treatment depending on whether the treatment plan and/or RFM meet the quality criteria. If the plan or RFM meets the quality criteria, the plan or RFM may be used for a patient treatment session. If the plan or RFM does not meet the quality criteria, the plan or RFM may be revised. Plan or RFM revisions or updates may be performed by the treatment system controller and/or treatment planning system.

Verification of Treatment Plan QA Methods

The method for evaluating a radiotherapy treatment described above may itself be verified to confirm that substituting positron emission activity or LOR data for PET detector signals results in radiation delivery that substantially approximates radiation delivery at the time of treatment. One variation of a method for verifying the treatment plan QA method described above may comprise selecting a phantom with a pre-defined PET-avid region (which simulates a target or tumor region in a patient), generating a treatment plan for the phantom, loading the treatment plan on a radiotherapy system, loading the phantom on the patient platform, detecting positron emissions or LORs from the phantom, emitting radiation in accordance with the treatment plan and the emission data, measuring the emitted radiation, and calculating a first fluence map and/or first dose map based on the measurements of the emitted radiation. The LORs emitted by the phantom may be recorded and stored in a memory of the treatment system controller. Next, the method may comprise removing the PET-avid phantom, and repeating radiation delivery as described above using the recorded LOR data instead of the PET-avid phantom (similar to the treatment plan evaluation method depicted in FIG. 2D). The method may comprise calculating a second fluence map and/or second dose map based on the measurements of the emitted radiation and then comparing the first fluence map with the second fluence map (and/or the first dose map with the second dose map). If the difference between the first and second fluence maps (and/or first and second dose maps) are below a pre-selected threshold, the treatment plan verification method and radiotherapy system are considered valid. If the difference is at or above a pre-selected threshold, a notification may be generated to alert the operator to perform additional testing of the treatment plan and/or radiotherapy system.

Systems

A radiation therapy system that may be used to provide image-guided radiation therapy may comprise an imaging system configured to acquire a partial image at a rate that exceeds the rate at which a target region moves. For example, a tumor can move with a maximum velocity of about 0.5 cm/s with a period of approximately 4 s. A sufficiently rapid imaging system may acquire a partial images within about 250 ms to 500 ms. If the imaging system acquires partial images at frequency that is two times greater than the largest frequency (or one-half of the period) of the tumor motion, the partial images may contain a complete sampling of the tumor motion trajectory. An imaging system of a radiation therapy system may be configured to acquire a partial tomographic image $x_i$ in a time window such that the motion of the target region is relatively small. Notably, any temporal blur in partial image acquisition directly maps to temporal blurring of the radiation fluence, and therefore, the delivered dose to the patient. An imaging system may comprise any suitable imaging modality, for example, PET, CT, Mill, ultrasound, etc. In some variations, a radiation therapy system may comprise a motion system to which the imaging system may be mounted. Optionally, a therapeutic radiation source and one or more beam-shaping components of the radiation therapy system may be mounted on the same gantry. In some variations, the imaging system may be mounted on a circular gantry configured to rotate around a patient area at a speed of about 30 RPM or more (e.g., about 60 RPM, about 65 RPM, about 70 RPM). Alternatively or additionally, the imaging system may be capable of acquiring tomographic imaging data without any rotation, for example, MM imaging systems.

A radiation therapy system that may be used to provide IGRT may comprise a therapeutic radiation source that is configured to deliver therapeutic radiation beams in real-time. That is, the therapeutic radiation source may be mounted on a motion system that rapidly moves the radiation source to each firing position around a patient area and the beam-shaping components are configured to change beam-shaping configurations in the time interval between firing positions so that a radiation beam may be applied to a target region before it moves substantially. The greater the latency between partial image acquisition and radiation delivery, the greater the likelihood that the target region would have moved by the time radiation is delivered. Accordingly, the motion system (e.g., gantry, chassis, arms, etc.) and the beam-shaping components (e.g., jaws, collimators, etc.) may be configured to move (e.g., motion system to move the radiation source to a new firing position) and change configuration (e.g., collimators or jaws to move/change the positioning of the radiopaque elements) in about 10 ms or less. For example, a radiation therapy system may comprise an imaging system (PET, CT, Mill, for example), a rotatable gantry, a linac mounted on the rotatable gantry, and a dynamic multi-leaf collimator mounted on the gantry and disposed in the beam path of the linac. The dynamic multi-leaf collimator may be, for example, a binary multi-leaf collimator, where each leaf is either in an open or closed configuration when located at a firing location, and may be in transit between the open and closed configurations while moving between firing positions. One example of radiation therapy system may have a gantry that rotates at 60 rpm, a dynamic multi-leaf binary collimator can change configuration in 10 ms, and a synchronous therapeutic radiation source can fire several pulses within 10 ms. A synchronous therapeutic radiation source pulses radiation while the leaves of the binary multi-leaf collimator are stationary for a brief period between moving between configurations. The instructions for moving the binary multi-leaf collimator may be generated with a latency as low as 10 ms after the acquisition of the partial image. Another example of a radiotherapy system may have a gantry that rotates at 5 rpm, a dynamic 2D multi-leaf collimator that is continuously changing configuration, where each leaf may be at any intermediate position between its fully closed and fully open positions when located at a firing position, and asynchronous therapeutic radiation source either pulsing at a rate of about 100 Hz or more or continuously emitting. In some variations, the leaves of the 2D dynamic multi-leaf collimator may be able to move at a velocity that can track twice the velocity of the tumor. The velocity may be based on a geometric calculation using the location of the therapeutic radiation source relative to both the 2D multi-leaf collimator and the target. The latency between the desired 2D multi-leaf collimator leaf position and the corresponding target position may be as low as 10 ms from the acquisition of the partial image.

For example, a tumor moving at a velocity of about 0.5 cm/s with a 4 second period, a sufficiently rapid therapeutic beam delivery system may be able to deliver radiation within about 10 ms from detecting the partial image. The radiation delivery system may be able to respond to a partial image such as $x_i$ and deliver the appropriate fluence response (using the RFM from the treatment plan) with low latency:

$$F_i = P_\alpha \cdot x_i$$

If fluence $F_i$ is not delivered immediately after it is calculated, then the actual target may have shifted from the delivered location. The amount of error may depend on the spatial extent of the shift. In summary, a radiation therapy system for IGRT may be configured to acquire partial images (some of which may be tomographic) at a frame-rate that captures the motion of the target and have a beam delivery system that may change a multi-leaf collimator configuration to deliver a new partial dose or beamlet to the location of a moving target region of RFZ.

Rapid Gantry System

Figure 3A:
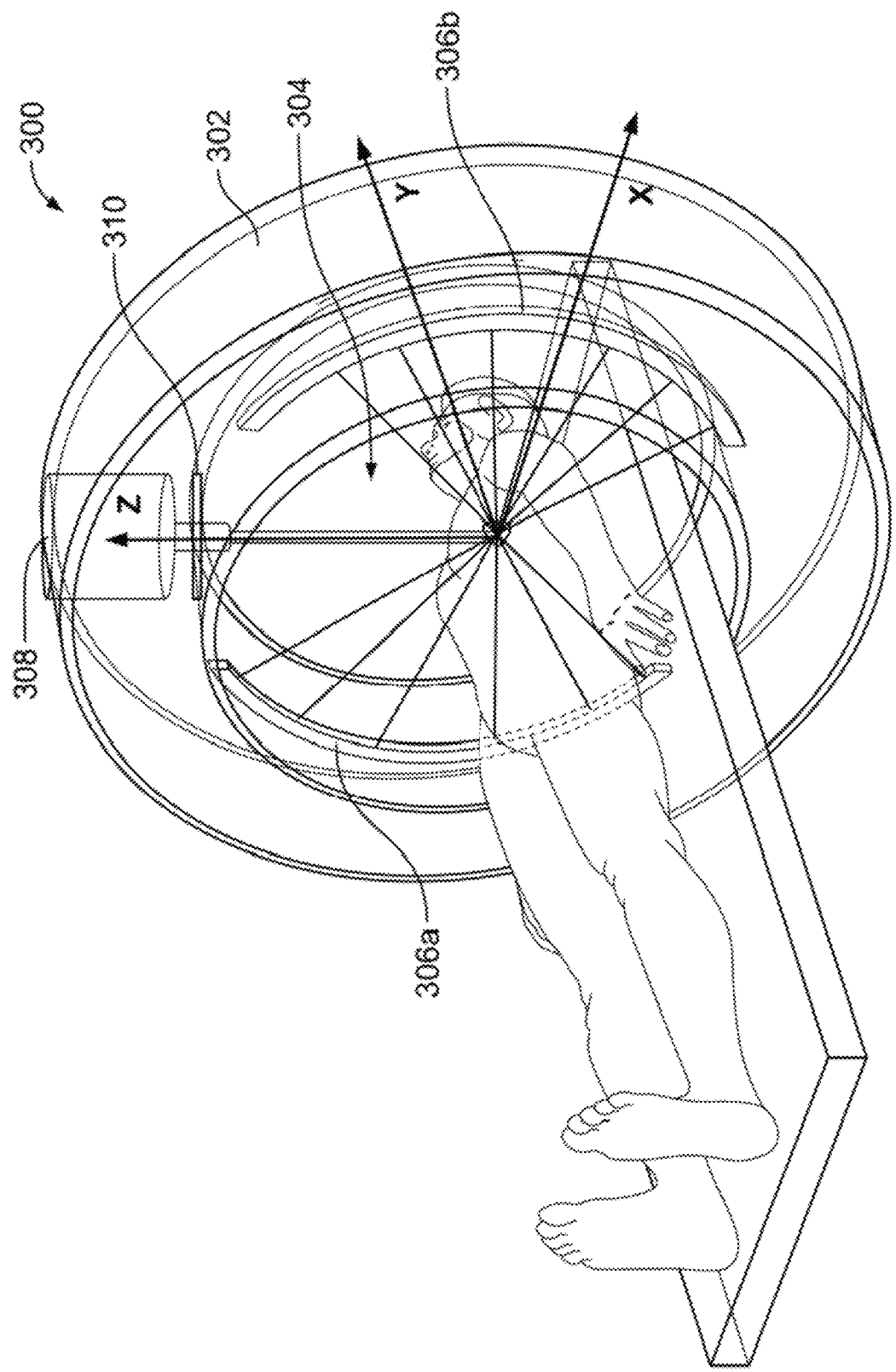
FIG. 3A depicts one variation of a radiation therapy system that may be used with any of the methods described herein.

One variation of a motion system may comprise a rotatable gantry. For example the rotatable gantry may be a continuously rotating gantry, configured to rotate 360 degrees around a patient area. FIG. 3A depicts an example of such a gantry, which may be configured to rotate at a rate of about 60 RPM. In this variation, the latency between the acquisition of a partial image and the delivery of a beamlet according to a fluence map that has been updated based on the acquired partial image may be from about 100 ms to about 5 s.

In some variations, a radiotherapy system may rotate a therapeutic radiation source and collimator around an axis, and my optionally stop at various firing angles α. A controller for the radiation therapy system may track the speed of the gantry as it rotates about the patient area. The gantry may rotate relatively slowly with a low or fixed angular velocity, or may rotate relatively quickly with a higher angular velocity such that it completes one revolution on the order of the frame rate of the imaging system.

Additional details and variations of a radiation therapy system comprising a high-speed gantry is described in U.S. application Ser. No. 15/814,222, filed Nov. 15, 2017, which is hereby incorporated by reference in its entirety.

Dynamic MLC

A radiation therapy system may comprise a beam-shaping component such as a MLC that is configured to change the configuration of the leaves within a selected time interval. For example, the selected time interval may be the time it takes for the motion system to move the linac from a first firing position to a second firing position. The position of the leaf as a function of time may be determined at least in part by the temporal bandwidth and/or configuration transition speed of each MLC leaf. In some variations, the collimator may not complete its configurational change within the time it takes for the motion system to move the linac between firing positions, and as a result, the target region may see some partial dose from the previous partial image.

A radiation therapy system may comprise a rotatable gantry that rotates a multi-leaf collimator around an axis. If the gantry is not rotating fast (e.g., slower than the frame rate of partial image acquisition) and is delivering dose from a given firing angle α for a projection $R_\alpha(x_i)$ from the partial image, the multi-leaf collimator may be a dynamic collimator so that it is in a desired configuration when moved to the firing angle α to deliver a dose at $R_\alpha(x_{i+1})$. In a variation where gantry is moving fast with respect to the imaging system, then the collimator may be a dynamic multi-leaf collimator comprising leaf actuation mechanisms that may change the positions of the leaves from their location at projection at $R_\alpha(x_i)$ to their location at a new angle $R_{\alpha+1}(x_i)$. The new angle may be based on the angular velocity of the gantry.

The leaf positions of a dynamic MLC at each firing location may be determined at least in part by the acquired partial image. That is, the radiation beam or fluence shaped by a dynamic MLC may allow delivery of a partial intensity modulated dose. The dose patterns summed over a treatment session, may approximate the final intensity modulated desired goal of the treatment plan. Some radiation therapy systems may comprise a 2D MLC, and in such systems, the MLC may not be able to faithfully represent the desired dose distribution $D_\alpha$, but may be configured to calculate correction factors to be used in further firing projections to correct for the inability to configure the MLC to the desired projection dose distribution. Some radiation therapy systems may comprise a high-speed binary MLC that may comprise leaf-actuation mechanisms that move each of the leaves to a new MLC configuration or pattern on every firing position or gantry angle. This architecture may facilitate generalized target tracking, even of multiple simultaneous targets. Further details of a dynamic binary multi-leaf collimator that may be used in a radiation therapy system are provided in U.S. patent application Ser. No. 15/179,823, filed Jun. 10, 2016, which is hereby incorporated by reference in its entirety.

FIG. 3A depicts one variation of a radiation therapy system that may be used for image-guided radiation therapy based on partial images. The radiation therapy system (300) may comprise a gantry (302) rotatable about a patient area (304), one or more PET detectors (306) mounted on the gantry, a therapeutic radiation source (308) mounted on the gantry, and a dynamic multi-leaf collimator (310) disposed in the beam path of the therapeutic radiation source. In some variations, the radiation therapy system may comprise a first array of PET detectors (306a) and a second array of PET detectors (306b) disposed across from the first array, a linear accelerator (308) or linac, and a dynamic binary multi-leaf collimator (310). The system may further comprise a controller that is in communication with the gantry, PET detectors, linac, and MLC, where the controller has one or more memories that may store treatment plans, radiation-firing matrices, fluence maps, system instructions/commands, and a processor configured to execute the calculations and methods described herein. A patient disposed within the patient area may have been injected with a PET tracer that emits positrons, and the PET tracer may accumulate at particular regions of the patient (e.g., irradiation-target regions such as tumor regions). The annihilation of a positron with a nearby electron may result in the emission of two photons traveling in opposite directions to define a line. One or more acquired partial images or detected partial image data may comprise one or more positron annihilation emission paths (i.e., lines of response or LORs, emission paths). In some variations, the PET detectors may be time-of-flight PET detectors, which may help to identify the location of the positron annihilation event. A previously-calculated treatment plan P may be updated in accordance with the PET imaging data or partial PET images acquired by the PET detectors to update the fluence map such that the linac and MLC leaf configuration/beamlet selection account for tumor movement. The fluence map may be updated using imaging data or partial images as the patient is moved through the patient area (e.g., stepped or otherwise moved through the gantry bore). Optionally, radiation therapy system (300) may comprise a CT imaging system mounted on the same gantry as the therapeutic radiation source or mounted on a separate gantry. Additional details and examples of PET-based radiation therapy systems are described in U.S. Appl. No. U.S. application Ser. No. 15/814,222, filed Nov. 15, 2017 which is hereby incorporated by reference in its entirety.

Figure 3B:
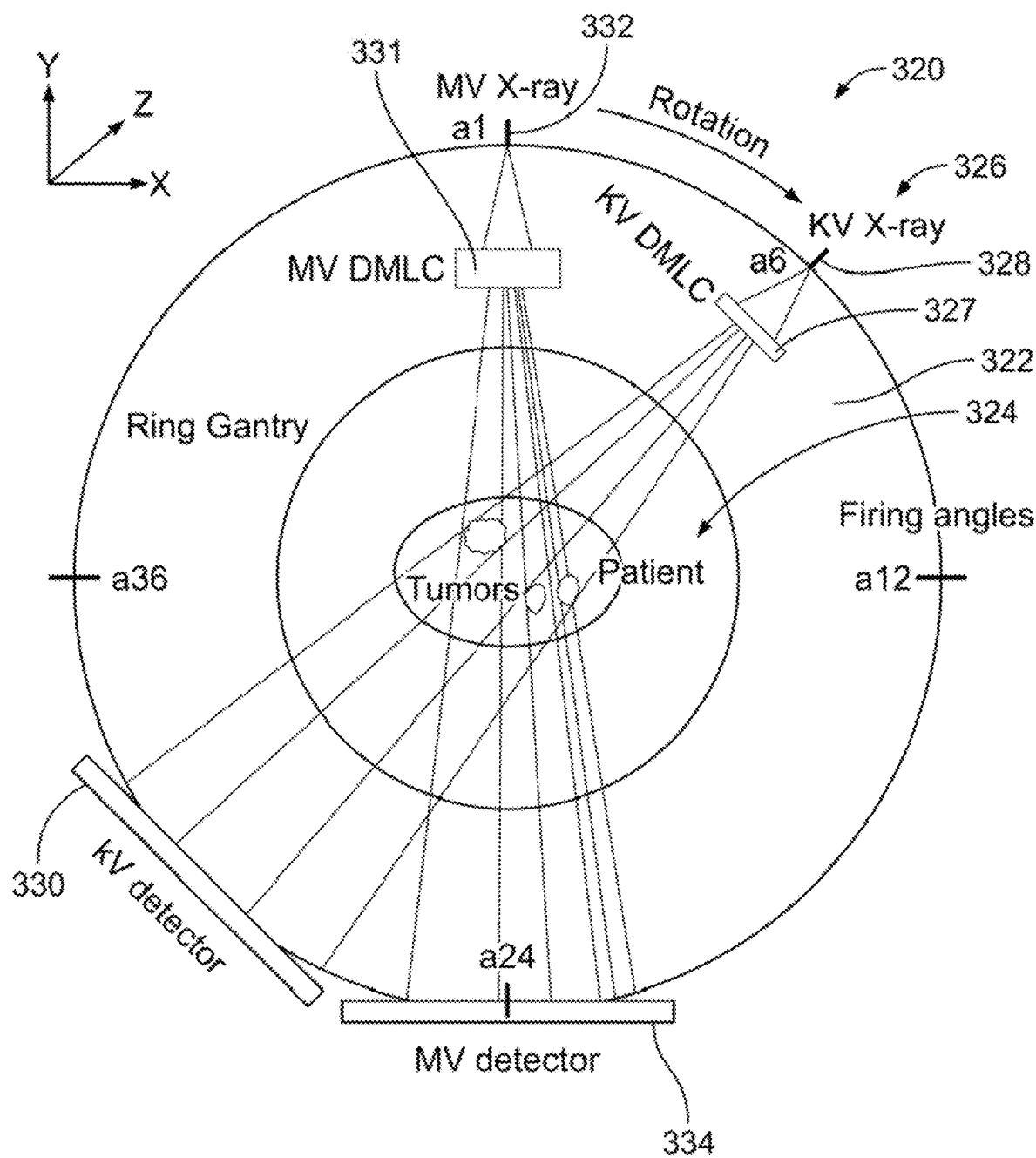
FIG. 3B depicts a cross-sectional view of another variation of a radiation therapy system that may be used with any of the methods described herein.

FIG. 3B depicts another one variation of a radiation therapy system that may be used for image-guided radiation therapy based on partial images. The radiation therapy system (320) may comprise a gantry (322) rotatable about a patient area (324), a kV imaging system (326) having a kV X-ray source (328) and a kV detector (330) mounted on the gantry, and a therapeutic radiation source (332) (e.g., MV X-ray source) and a MV detector (334) mounted on the gantry (322). The kV detector (330) may be located across the kV X-ray source (328) and the MV detector (334) may be located across the MV X-ray source (332). Optionally, the kV imaging system may comprise a dynamic MLC (327) over the kV X-ray source (328). The system may comprise a dynamic MLC (331) disposed over the MV X-ray source (332). Partial images or imaging data may comprise image data acquired by the kV detector after each kV X-ray source pulse. Examples of partial kV X-ray images may include X-ray projection image data, such as 2D projection data. A fluence map may be calculated by multiplying a treatment plan radiation-firing matrix P with the kV X-ray imaging data or partial kV X-ray images acquired by the kV detector so that radiation emission by the linac, as well as MLC leaf pattern/beamlet selection, may account for tumor movement. The fluence map may be updated using imaging data or partial images as the patient is moved through the patient area (e.g., stepped or otherwise moved through the gantry bore). Alternatively or additionally, partial MV X-ray images or data acquired by the MV detector may be used to update the fluence map and/or treatment plan. Additional details and examples of radiation therapy systems are described in PCT Appl. No. PCT/US2018/025252, filed Mar. 29, 2018, which is hereby incorporated by reference in its entirety.

Figure 3C:
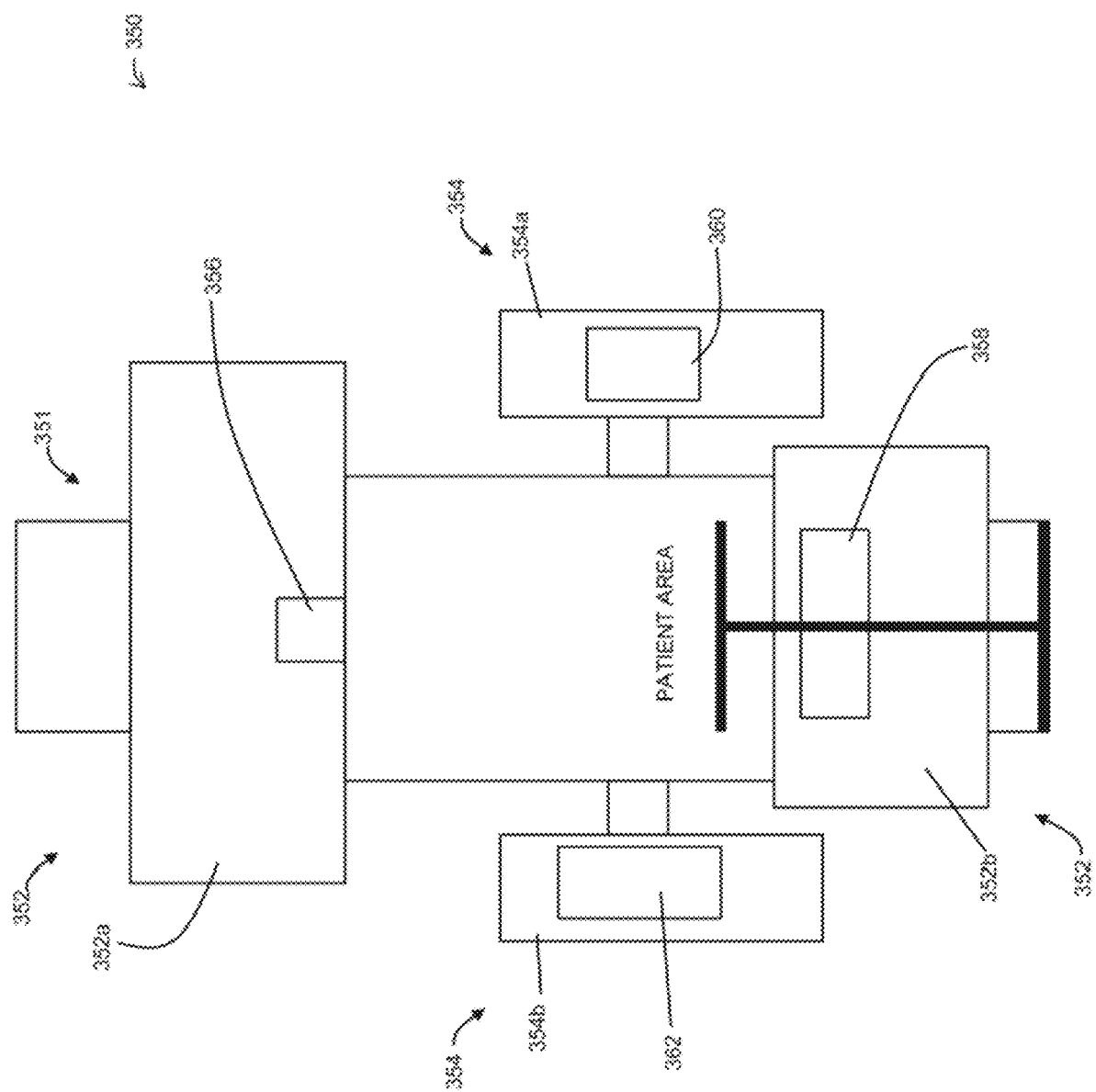
FIG. 3C depicts a schematic representation of another variation of a radiation therapy system that may be used with any of the methods described herein.

FIG. 3C depicts another one variation of a radiation therapy system (350) that may be used for image-guided radiation therapy based on partial images. Radiation therapy system (350) may comprise a gantry (351) comprising a first pair of arms (352) rotatable about a patient area and a second pair of arms (354) rotatable about the patient area, an imaging system comprising a kV radiation source (356) mounted on a first arm (352a) of the first pair of arms (152) and a kV detector (358) mounted on a second arm (352b) of the first pair of arms (352), and a therapeutic radiation system comprising an MV radiation source (360) mounted on a first arm (354a) of the second pair of arms (354) and an MV detector (362) mounted on a second arm (354b) of the second pair of arms (354). The first and second arms of the first pair of arms (352) may be located opposite each other (e.g., on opposite sides of the patient area, across from each other, and/or about 180 degrees from each other), such that the kV radiation source (356) and the kV detector (358) are located opposite each other (e.g., the kV detector is located in the beam path of the kV radiation source). The first and second arms of the second pair of arms (354) may be located opposite each other (e.g., on opposite sides of the patient area, across from each other, and/or about 180 degrees from each other), such that the MV radiation source (360) and the MV detector (362) are located opposite each other (e.g., the MV detector is located in the beam path of the MV radiation source). Partial images or imaging data may comprise image data acquired by the kV detector after each kV X-ray source pulse. Examples of partial kV X-ray images may include X-ray projection image data, such as 2D projection data. A fluence map may be calculated by multiplying a treatment plan radiation-firing matrix P with the kV X-ray imaging data or partial kV X-ray images acquired by the kV detector so that radiation emission by the linac, as well as MLC leaf pattern/beamlet selection, may account for tumor movement. The fluence map may be updated using imaging data or partial images as the patient is moved through the patient area (e.g., stepped or otherwise moved through the gantry bore). Alternatively or additionally, partial MV X-ray images or data acquired by the MV detector may be used to update the fluence map and/or treatment plan.

Controller

A system (e.g., a treatment planning system, radiation treatment system) that may be configured to update a treatment plan (e.g., fluence map, sinogram, and/or radiation-firing matrix) based on low SNR or partial images may comprise a controller in communication with the imaging system of the radiation therapy system and/or the therapeutic radiation source and/or the multi-leaf collimator and/or gantry. The controller may comprise one or more processors and one or more machine-readable memories in communication with the one or more processors. The controller may be connected to a radiation therapy system and/or other systems by wired or wireless communication channels. In some variations, the controller of a treatment planning system may be located in the same or different room as the patient. For example, the controller may be coupled to a patient platform or disposed on a trolley or medical cart adjacent to the patient and/or operator.

The controller may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks.

Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like.

Processor

In some embodiments, a processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), or the like. The processor may be configured to run and/or execute application processes and/or other modules, processes and/or functions associated with the system and/or a network associated therewith. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, or the like.

Memory

In some embodiments, memory may include a database and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory may store instructions to cause the processor to execute modules, processes and/or functions associated with the system, such as one or more treatment plans, full or high SNR images, partial or low SNR images, the calculation of fluence maps based on treatment plan and/or clinical goals, segmentation of fluence maps into radiation therapy system instructions (e.g., that may direct the operation of the gantry, therapeutic radiation source, multi-leaf collimator, and/or any other components of a radiation therapy system and/or diagnostic or treatment planning system), and image and/or data processing associated with treatment planning and/or delivery.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other embodiments described herein relate to a computer program product, which may include, for example, the instructions and/or computer code disclosed herein.

A user interface may serve as a communication interface between an operator or clinician and the treatment planning system. The user interface may comprise an input device and output device (e.g., touch screen and display) and be configured to receive input data and output data from one or more of the support arm, external magnet, sensor, delivery device, input device, output device, network, database, and server. Sensor data from one or more sensors may be received by user interface and output visually, audibly, and/or through haptic feedback by one or more output devices. As another example, operator control of an input device (e.g., joystick, keyboard, touch screen) may be received by user and then processed by processor and memory for user interface to output a control signal to one or more support arms, external magnets, intracavity devices, and delivery devices.

Some variations of a treatment planning system for generating fluence maps may comprise a display device that may allow an operator to view graphical and/or textual representations of fluence maps, and/or dose distributions, and/or regions of interest, and/or volumes of interest, and/or patient anatomical images, and/or patient data (e.g., physiological and/or biological), and the like. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

Communication

In some embodiments, a treatment planning system and/or radiation therapy system may be in communication with other computing devices via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some embodiments, the systems, apparatuses, and methods described herein may include a radiofrequency receiver, transmitter, and/or optical (e.g., infrared) receiver and transmitter to communicate with one or more devices and/or networks.

While various inventive variations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive variations described herein. It is, therefore, to be understood that the foregoing variations are presented by way of example only and that, within the scope of the appended claims and equivalents thereto, inventive variations may be practiced otherwise than as specifically described and claimed. Inventive variations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A method for evaluating treatment plan quality comprising:

powering on a radiation therapy system comprising a therapeutic radiation source, and a controller in communication with the therapeutic radiation source, wherein the controller comprises a processor and a memory with a treatment plan and positron emission activity data stored therein, and wherein the treatment plan comprises a radiation-firing matrix P and a planned fluence map, and the positron emission activity data comprises line-of-response (LOR) data;

calculating a radiation fluence based on the radiation-firing matrix P and LOR data using the controller;

emitting radiation using the therapeutic radiation source according to the calculated radiation fluence;

measuring the emitted radiation;

calculating a fluence map based on the measured radiation;

comparing the calculated fluence map and the planned fluence map; and generating a notification of the fluence map comparison.

2. The method of claim 1, wherein the radiation therapy system further comprises a treatment area and the method further comprises placing one or more radiographic films in the treatment area, and measuring the emitted radiation by analyzing the radiographic films.

3. The method of claim 1, wherein the radiation therapy system further comprises a radiation detector located across from the therapeutic radiation source, and measuring the emitted radiation comprises acquiring radiation data using the radiation detector data and transmitting the radiation data to the controller.

4. The method of claim 1, wherein positron emission activity data comprises diagnostic PET imaging data.

5. The method of claim 4, wherein the positron emission activity data comprises spatially filtered diagnostic PET imaging data.

6. The method of claim 5, wherein the radiation therapy system comprises an array of PET detectors having a detector field-of-view, and wherein the spatially filtered diagnostic PET imaging data has a field-of-view that corresponds to the detector field-of-view.

7. The method of claim 1, wherein the positron emission activity data comprises a plurality of synthetic lines-of-response (LORs) generated based on diagnostic PET imaging data acquired on a PET imaging system and machine parameters of the PET imaging system.

8. The method of claim 1, wherein comparing the calculated fluence map and the planned fluence map comprises calculating a fluence difference between the calculated fluence map and the planned fluence map and determining whether the calculated fluence difference meets or exceeds a pre-specified fluence difference threshold, and wherein the method further comprises adjusting the treatment plan if the calculated fluence difference exceeds the pre-specified fluence difference threshold.

9. The method of claim 1, wherein the treatment plan comprises a planned dose map, and the method further comprises calculating a dose map based on the measured radiation, calculating a dose difference between the calculated dose map and the planned dose map, and generating a notification of the calculated dose difference.

10. The method of claim 9, wherein generating a notification comprises calculating a distance to agreement (DTA) value of fluence isodoses and an absolute dose difference between the calculated dose map and the planned dose map for multiple time points, and determining whether a percentage of time points that are within a DTA value and within a specified absolute dose difference threshold is greater than a threshold percentage.

11. The method of claim 10, wherein the threshold percentage is about 95%, the DTA value is about 3 mm, and the specified absolute dose difference threshold is about 3% from a planned absolute dose.

12. The method of claim 9, further comprising determining whether the calculated dose difference meets or exceeds a pre-specified dose difference threshold.

13. A radiation therapy system comprising:
a rotatable gantry;
a therapeutic radiation source mounted on the gantry;
one or more imaging sensors mounted on the gantry configured to acquire a partial image $x_i$ of a target region; and
a controller in communication with the gantry, the therapeutic radiation source, and the one or more imaging sensors, the controller configured to calculate a radiation fluence to be delivered to the target region, wherein calculating a radiation fluence comprises multiplying a radiation-firing matrix P and the partial image $x_i$, wherein the radiation-firing matrix P is calculated based on a previously-acquired image X of the target region.

14. The system of claim 13, wherein the radiation-firing matrix P is a diagonal matrix of scalars s diag(s), such that $P \cdot x_i = s \lfloor x_i$, where $\lfloor$ is a point-wise product operation.

15. The system of claim 13, wherein calculating the radiation fluence comprises convolving the radiation-firing matrix P with the partial image $x_i$.

16. The system of claim 13, the radiation-firing matrix P is a Toeplitz matrix toep(f), such that $P \cdot x_i = f * x_i$, where * is a convolution operation and f is a fluence to be delivered to the target region according to a treatment plan.

17. The system of claim 13, wherein a signal-to-noise ratio (SNR) of the partial image $x_i$ is less than the SNR of the image X.

18. The system of claim 13, wherein the partial image $x_i$ comprises a reconstruction from a set of positron annihilation emission paths, X-ray projections, or sub-samples in k-space from a MRI imaging pulse sequence.

19. The system of claim 13, wherein the image X is a motion de-blurred image.

20. The system of claim 13, wherein the controller is further configured to select a projection angle α, calculate a projected fluence $f_\alpha$ of the calculated fluence at a radiation beam firing angle α and store the projected fluence $f_\alpha$ in a memory of the controller.

21. The system of claim 20, further comprising a multi-leaf collimator having an array of leaves disposed in a beam path of the therapeutic radiation source, and wherein the rotatable gantry is configured to move the therapeutic radiation source to the radiation beam firing angle α, and wherein the controller is further configured to segment the projected fluence $f_\alpha$ to collimator leaf position instructions, store the leaf position instructions in controller memory, and the position of each of the collimator leaves is adjustable according to the collimator leaf position instructions.

22. The system of claim 21, wherein calculating the projected fluence $f_\alpha$ comprises selecting a projection angle α, calculating a projection $x_{i,\alpha}$ of the partial image $x_i$ at the radiation beam firing angle α and storing the projected partial image $x_{i,\alpha}$ in controller memory, and multiplying a per angle radiation-firing matrix $P_\alpha$ with the projected partial image $x_{i,\alpha}$ ($P_\alpha\ x_{i,\alpha}$), wherein the per-angle radiation-firing matrix $P_\alpha$ comprises a set of radiation-firing matrices $P_{i,\alpha}$ for each projection angle α.

23. The system of claim 22, wherein the per-angle radiation-firing matrix $P_\alpha$ is a Toeplitz matrix $toep(p_\alpha)$ that implements a convolution operation $p_\alpha * x_i$.

24. The system of claim 22, wherein the per-angle radiation-firing matrix $P_\alpha$ is a diagonal matrix $diag(p_\alpha)$ that implements a pointwise multiplication operation $p_\alpha \cdot x_i$.

25. The system of claim 13, wherein the one or more imaging sensors comprises one or more PET detectors and the partial image $x_i$ is generated from a set of positron annihilation emission paths.

26. The system of claim 13, wherein the one or more imaging sensors comprises one or more X-ray detectors and the partial image $x_i$ is generated from a set of X-ray projections.

27. The system of claim 13, wherein the one or more imaging sensors comprises one or more MRI sensors and the partial image $x_i$ is generated from a set of sub-samples in k-space from a MRI imaging pulse sequence.

28. The system of claim 17, wherein the SNR of the partial image $x_i$ is about 40% less than the SNR of the image X.

29. The system of claim 22, wherein the gantry is configured to move the therapeutic radiation source to firing beam angle α and emit a radiation beam in accordance with the calculated fluence $f_\alpha$ within a specified time period after acquiring the partial image $x_i$.

30. The system of claim 29, wherein the specified time period is less than about 10 seconds.

31. The system of claim 30, wherein the specified time period is less than about 5 seconds.

32. The system of claim 31, wherein the specified time period is less than about 1 second.

33. The system of claim 13, wherein the gantry is rotatable at a speed of about 20 RPM or more.

34. The system of claim 22, wherein the controller is further configured to apply a linear contrast filter to the partial image $x_i$.

35. The system of claim 34, wherein any negative values of the filtered partial image $x_i$ are added to a subsequent filtered partial image $x_{i+1}$.

36. The system of claim 22, wherein the controller is further configured to calculate a real-time delivered dose estimate.

37. The system of claim 22, wherein the controller is further configured to apply a spatial filter to the partial image $x_i$.

38. The system of claim 13, wherein the previously-acquired image X is a first image and A is a known dose calculation matrix, and the controller is further configured to calculate an updated radiation-firing matrix $P_{prescan}$ by acquiring a second image $X_{prescan}$ using the one or more imaging sensors and iterating through matrix values for $P_{prescan}$ such that the following conditions are met:

$$A \cdot P \cdot X \approx A \cdot P_{prescan} \cdot X_{prescan}.$$

39. The system of claim 38, wherein the controller is further configured to calculate a dose matrix $D_{prescan}$ based on $X_{prescan}$, calculate a difference value between $D_p$ rescan with a dose matrix D that has been calculated based on image X, and if the difference value exceeds a pre-selected threshold, generate a notification that the pre-selected threshold has been exceeded.

* * * * *